(12) United States Patent
Garland et al.

(10) Patent No.: US 11,185,544 B2
(45) Date of Patent: Nov. 30, 2021

(54) FORMULATIONS OF 4-METHYL-5-(PYRAZIN-2-YL)-3H-L,2-DITHIOLE-3-THIONE, TASTE-MODIFIED FORMULATIONS, AND METHODS OF MAKING AND USING SAME

(71) Applicant: ST IP Holding AG, Zug (CH)

(72) Inventors: Anthony Chris Garland, Los Angeles, CA (US); Barbara-Jean Anne Bormann-Kennedy, Wellfleet, MA (US); Bomi Framroze, Menlo Park, CA (US); Bret Berner, Half Moon Bay, CA (US); Michael Edward Grass, Bend, OR (US); Casey Keith Jager, Bend, OR (US); Corey Jay Bloom, Bend, OR (US); Mark Joseph Kastantin, Bend, OR (US); Romain Bachelard, Le Bar-sur-loup (FR)

(73) Assignee: ST IP Holding AG, Zug (CH)

( * ) Notice: Subject to any disclaimer, the term of this patent is extended or adjusted under 35 U.S.C. 154(b) by 0 days.

(21) Appl. No.: 16/351,122

(22) Filed: Mar. 12, 2019

(65) Prior Publication Data

US 2019/0209557 A1 Jul. 11, 2019

Related U.S. Application Data

(63) Continuation of application No. PCT/IB2017/001231, filed on Sep. 12, 2017.

(60) Provisional application No. 62/412,701, filed on Oct. 25, 2016.

(51) Int. Cl.

| A61K 31/497 | (2006.01) |
|---|---|
| A61K 9/19 | (2006.01) |
| A61K 9/16 | (2006.01) |
| A61K 9/14 | (2006.01) |
| A61K 9/10 | (2006.01) |
| C07D 409/04 | (2006.01) |
| A61K 47/32 | (2006.01) |

(52) U.S. Cl.
CPC ............. *A61K 31/497* (2013.01); *A61K 9/10* (2013.01); *A61K 9/145* (2013.01); *A61K 9/146* (2013.01); *A61K 9/1635* (2013.01); *A61K 9/19* (2013.01); *A61K 47/32* (2013.01); *C07D 409/04* (2013.01); *C07B 2200/13* (2013.01)

(58) Field of Classification Search
CPC .......... A61K 31/497; A61K 9/19; A61K 9/16; A61K 9/14
See application file for complete search history.

(56) References Cited

U.S. PATENT DOCUMENTS

| 7,012,148 B2 | 3/2006 | Curphey |
|---|---|---|
| 7,067,116 B1 | 6/2006 | Bess et al. |
| 7,199,122 B2 | 4/2007 | Ruggeri et al. |
| 7,288,652 B2 | 10/2007 | Kim et al. |
| 7,452,884 B2 | 11/2008 | Ruggeri et al. |
| 7,648,712 B2 | 1/2010 | Bess et al. |
| 7,803,353 B2 | 9/2010 | Lee et al. |
| 7,959,958 B2 | 6/2011 | Furrer et al. |
| 8,142,806 B2 | 3/2012 | Gupta et al. |
| 8,461,136 B2 | 6/2013 | Fahl et al. |
| 8,481,762 B2 | 7/2013 | Commo |
| 8,664,261 B2 | 3/2014 | Furrer |
| 8,858,995 B2 | 10/2014 | Gupta et al. |
| 8,920,864 B2 | 12/2014 | Spence et al. |
| 9,308,192 B2 | 4/2016 | Coulombe et al. |
| 9,314,419 B2 | 4/2016 | Lin et al. |
| 9,370,504 B2 | 6/2016 | Kim et al. |
| 9,452,982 B2 | 9/2016 | Bell et al. |
| 9,839,638 B2 | 12/2017 | Fahl et al. |
| 9,974,740 B2 | 5/2018 | Spence et al. |
| 2005/0163855 A1* | 7/2005 | Cho ..................... C07D 409/04 424/486 |
| 2006/0106079 A1 | 5/2006 | Kim et al. |
| 2014/0343092 A1* | 11/2014 | Haydar ................ C07D 471/04 514/292 |
| 2015/0359739 A1 | 12/2015 | Bunick et al. |
| 2016/0206641 A1 | 7/2016 | Singh |

FOREIGN PATENT DOCUMENTS

| AU | 2003284758 A1 | 6/2004 |
|---|---|---|
| CA | 2718152 A1 | 9/2008 |
| CN | 100366619 C | 2/2008 |
| EP | 1474131 A1 | 11/2004 |
| EP | 1565460 A1 | 8/2005 |
| EP | 1696958 A1 | 9/2006 |
| EP | 1803468 A1 | 7/2007 |
| EP | 2810564 B1 | 6/2017 |
| JP | 2006511508 A | 4/2006 |
| JP | 2008-521812 A | 6/2008 |
| KR | 100491318 B1 | 5/2005 |

(Continued)

OTHER PUBLICATIONS

Liu, P. (2013) Nanocrystal formulation for poorly soluble drugs. Dissertationes bioscientiarum molecularium Universitatis Helsingiensis in Viikki, Dec. 2013, pp. 62 (Year:2013).

Kochar et al., "Oltipraz Provides Protection to Swiss Albino Mice Against Gamma Radiation", Pharmacologyonline, Universita Degli Studi Di Salerno, IT, vol. 2, Jan. 1, 2010, pp. 39-44.

International Preliminary Report on Patentability, International Application No. PCT/IB2017/001231 (published as WO 2018/047002), 12 pages (dated Mar. 12, 2019).

International Search Report and Written Opinion, International Application No. PCT/IB2017/001231 (published as WO 2018/047002), 16 pages (dated Jan. 31, 2018).

(Continued)

*Primary Examiner* — Zohreh A Fay
(74) *Attorney, Agent, or Firm* — Hoffmann & Baron, LLP

(57) ABSTRACT

This disclosure provides, among other things, compositions comprising quantities of oltipraz crystals, as well as method of making such compositions, and method of treating patients using such compositions. Taste-modified compositions also are provided.

23 Claims, 7 Drawing Sheets

(56) References Cited

FOREIGN PATENT DOCUMENTS

| | | |
|---|---|---|
| KR | 20180123796 A | 11/2018 |
| WO | WO 200185142 A1 | 11/2001 |
| WO | WO 2004048369 A1 | 6/2004 |
| WO | WO 2005070397 A1 | 8/2005 |
| WO | WO 2006/058022 A1 | 6/2006 |
| WO | WO 2008110585 A2 | 9/2008 |
| WO | WO 2012170676 A1 | 12/2012 |
| WO | WO 2013043553 A1 | 3/2013 |
| WO | WO 2014100403 A1 | 6/2014 |
| WO | WO 2016207914 A2 | 12/2016 |
| WO | WO 2017109599 A1 | 6/2017 |
| WO | WO 2017168263 A1 | 10/2017 |

International Preliminary Report on Patentability, International Application No. PCT/IB2017/001312 (published as WO 2018/047013), 12 pages (dated Mar. 12, 2019).
International Search Report and Written Opinion, International Application No. PCT/IB2017/001312 (published as WO 2018/047013), 16 pages (dated Jan. 31, 2018).
Office Action with English translation, Japanese Application No. 2019-535991, 14 pp. (dated Jul. 6, 2021).

\* cited by examiner

CHI-SQUARE ANALYSIS OF PERCENT OF ANIMAL DAYS WITH A MUCOSITIS SCORE ≥ 3

FORMULATIONS OF 4-METHYL-5-(PYRAZIN-2-YL)-3H-1,2-DITHIOLE-3-THIONE, TASTE-MODIFIED FORMULATIONS, AND METHODS OF MAKING AND USING SAME

CROSS REFERENCE TO RELATED APPLICATIONS

This application is a continuation of PCT/IB2017/001231, filed on Sep. 12, 2017, which claims the benefit of priority to Indian Application Nos. 201611031045 and 201611031046, both filed Sep. 12, 2016, and U.S. Provisional Application 62/412,701, filed Oct. 25, 2016. The entire contents of each priority application, including their specifications, claims and drawings, are expressly incorporated herein by reference.

FIELD

The disclosure herein relates to new pharmaceutical compositions comprising the compound 4-methyl-5-(pyrazin-2-yl)-3H-1,2-dithiole-3-thione (depicted in Formula I below), as well as methods of making and using such formulations. The compound, which is also known as oltipraz, has known uses in the medical field.

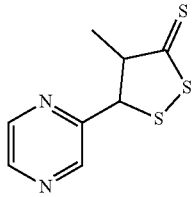

Formula I

BACKGROUND

Mucositis is the painful inflammation and ulceration of mucous membranes often caused by chemo-/radio-therapy for cancer. Mucositis typically occurs in the gastrointestinal (GI) tract. e.g. in the oral (e.g. buccal) cavity. Oral and gastrointestinal (GI) mucositis is a common, painful side-effect of patients undergoing treatments such as high-dose chemotherapy, hematopoietic stem cell transplantation and the like.

Lesions of mucositis are characterized by mucosal breakdown resulting in extensive, deep ulcerations. Among granulocytopenic cancer patients, the loss in mucosal integrity created by ulceration results in the generation of a portal of entry for indigenous oral bacteria that often leads to sepsis or bacteremia. Mucositis occurs to some degree in more than one third of patients receiving anti-neoplastic drug therapy. The frequency and severity are significantly greater among patients who are treated with induction therapy for leukemia or with many of the conditioning regimens for hematopoietic stem cell marrow transplant. Moderate to severe mucositis occurs in virtually all patients who receive radiation therapy for tumors of the head and neck and typically begins with cumulative exposures of 20 Gy and then worsens as total doses of 60 Gy or more are reached.

Clinically mucositis progresses through three stages:
1. Early, painful mucosal erythema, which can be palliated with local anesthetics or non-narcotic analgesics.
2. Painful ulceration with pseudomembrane formation. Pain is often of such intensity as to require parenteral narcotic analgesia.
3. Spontaneous healing, occurring about 2-4 weeks after cessation of anti-neoplastic therapy.

To date, therapy for mucositis is predominantly palliative and focused on pain control and maintenance of nutrition. For example, oral mucositis is in practice often addressed only by palliative measures such as improvements in oral hygiene, alone or in combination with analgesic therapy such as administration of lidocaine. Such approaches have typically low efficacy and are insufficient for addressing severe cases of mucositis. Even opioids are often insufficient to control mucositis pain. Various pharmaceutical therapies for mucositis have been proposed however to date there remains a clear need for improved treatments for mucositis. In this context, oltipraz (4-methyl-5-(pyrazin-2-yl)-3H-1,2-dithiole-3-thione) has been suggested as a potential candidate. See, e.g., Fahl et al. PCT/US2001/014464 (published as WO2001085142) and Prendergast PCT/EP2008/052969 (published as WO 2008/110585).

The properties of known forms of oltipraz render its use impractical as a treatment, however. Oltipraz is known to exist in crystalline form. To date, however, known crystalline oltipraz formulations, which are prepared by recrystallizing oltipraz (see, e.g., WO2016207914), comprise a mixture of oltipraz crystals of varying sizes up to millimeters in length along the longest axis, which crystals are highly insoluble in water and have poor bioavailability when administered topically or orally. Accordingly, there is a need for new formulations of oltipraz that have improved properties for treating conditions such as mucositis. There is also a need for new pharmaceutical compositions and dosage forms of oltipraz.

SUMMARY

The inventors have surprisingly found that the properties of crystalline oltipraz can be improved by formulating compositions in which crystal parameters including particle size are controlled. By controlling the crystal particle size and formulation, crystals of oltipraz are provided that have prolonged size-stability in aqueous suspension and improved aqueous solubility as compared to previously known forms of oltipraz such as recrystallized oltipraz prepared according to the process disclosed in WO2016207914. For example, the inventors have found that formulations comprising crystals of oltipraz that are of a controlled, much smaller size have beneficial properties such as excellent stability in the form of a dry composition and/or the ability to be readily re-suspended in aqueous compositions to form substantially homogeneous dispersions of oltipraz crystals that typically exhibit substantially improved solubility, size-stability and/or efficacy compared to other forms of oltipraz known in the art. Further, unlike recrystallized oltipraz, the formulations disclosed herein can increase the gene expression of glutathione peroxidase 4 (GPX4) and/or myeloperoxidase (MPO) in a human or non-human animal patient, as well as decrease the gene expression of Peroxiredoxin 2 (PRDX2) in a human or non-human animal patient. The new forms and compositions of oltipraz crystals have therapeutic uses for example in the treatment of mucositis, and in this regard, the new forms and compositions of oltipraz crystals exhibit improved beneficial properties compared to such recrystallized oltipraz.

This disclosure therefore provides crystals of 4-methyl-5-(pyrazin-2-yl)-3H-1,2-dithiole-3-thione having a MHD of from 30 to 2000 nm. As described in more detail below, the term 'MHD' is a measure of particle size and refers to the intensity averaged, mean hydrodynamic diameter (Z-average) as determined by the cumulants fitting of dynamic light scattering. The crystals have improved solubility in aqueous solution compared to previous crystal forms of oltipraz and when comprised in pharmaceutical compositions provide for increased therapeutic efficacy.

The disclosure also provides compositions comprising quantities of crystals of 4-methyl-5-(pyrazin-2-yl)-3H-1,2-dithiole-3-thione. In certain embodiments the crystals have an intensity averaged, mean hydrodynamic diameter (Z-average) as determined by dynamic light scattering (DLS) in a range of from 30 to 2000 nm. (For convenience, in this disclosure the dimension of "intensity averaged, mean hydrodynamic diameter (Z-average) as determined by the cumulants fitting of dynamic light scattering" data is abbreviated as "MHD" and the precise method by which DLS measurements can be made to determine the MHD are provided below.) Usually, the crystals have a MHD of from 30 to 1200 nm; more often from 100 to 700 nm and still more typically from 150 to 450 nm or from 400 nm to 700 nm or from 400 nm to 600 nm. In certain embodiments, the crystals have a MHD within a target range of from 30 to 100, 100 to 1200 nm, 150 to 600 nm, 150 to 450 nm, 400 nm to 700 nm, 400 nm to 600 nm or 450 to 550 nm.

The compositions typically comprise at least one stabilizing agent that stabilizes the crystals such that they retain a MHD within a target range of from 100 to 2000 nm if left in water at 25° C. for a period of from 1 to 24 hours, such as a period of 1 hour, 6 hours, or 24 hours. Usually, the stabilized crystals retain a MHD in a target range of 30 to 100, 100 to 1200 nm, 150 to 600 nm, 150 to 450 nm, 400 to 700 nm, 400 to 600 nm or 450 to 550 nm if left in water at 25° C. for a period of from about 1 to about 24 hours, such as about 6 hours. Usually, the stabilized crystals will retain a MHD in a target range of 30 to 100, 100 to 1200 nm, 150 to 600 nm, 150 to 450 nm, 400 to 700 nm, 400 to 600 nm, or 450 to 550 nm if left in water at 25° C. for a period of 1 hour, 6 hours, or 24 hours. Typically, the stabilizing agent is one or more of a polymer, a surfactant and/or a bulking agent. In certain embodiments, the crystals are stabilized by a combination of stabilizing agents such as a polymer and surfactant, which together act to stabilize the crystals.

This disclosure provides dry and liquid compositions comprising crystals as defined herein. The dry compositions can be mixed with water and/or another liquid to provide a liquid composition of such crystals. This disclosure also provides methods of making such dry and liquid suspensions. This disclosure also provides dry compositions, including, e.g., spray-dried or lyophilized compositions, prepared from aqueous compositions comprising the crystals and a bulking agent. This disclosure also provides pharmaceutical compositions comprising such crystals. This disclosure further provides pharmaceutical containers for preparing and administering a dose of a liquid pharmaceutical composition comprising crystals as described herein. This disclosure also provides methods of treating human and non-human animal patients with pharmaceutical compositions disclosed herein. Further provided are crystals as described herein and compositions comprising such crystals for use in the treatment of a patient such as a human or non-human animal. This disclosure also provides crystals as described herein and compositions comprising such crystals for use in the manufacture of a medicament for the treatment of a patient in need thereof, such as a human or non-human animal.

This disclosure also provides compositions comprising of the compound 4-methyl-5-(pyrazin-2-yl)-3H-1,2-dithiole-3-thione, including compositions described above, together with additives that modify and improve the taste of such compositions to make them palatable, even for patients with mucositis, including oral mucositis, including moderate to severe oral mucositis.

BRIEF DESCRIPTION OF THE FIGURES

FIG. 6 illustrates the effect of different bulking agents on the stability of the oltipraz crystals in an aqueous suspension.

DETAILED DESCRIPTION

Figure 1:
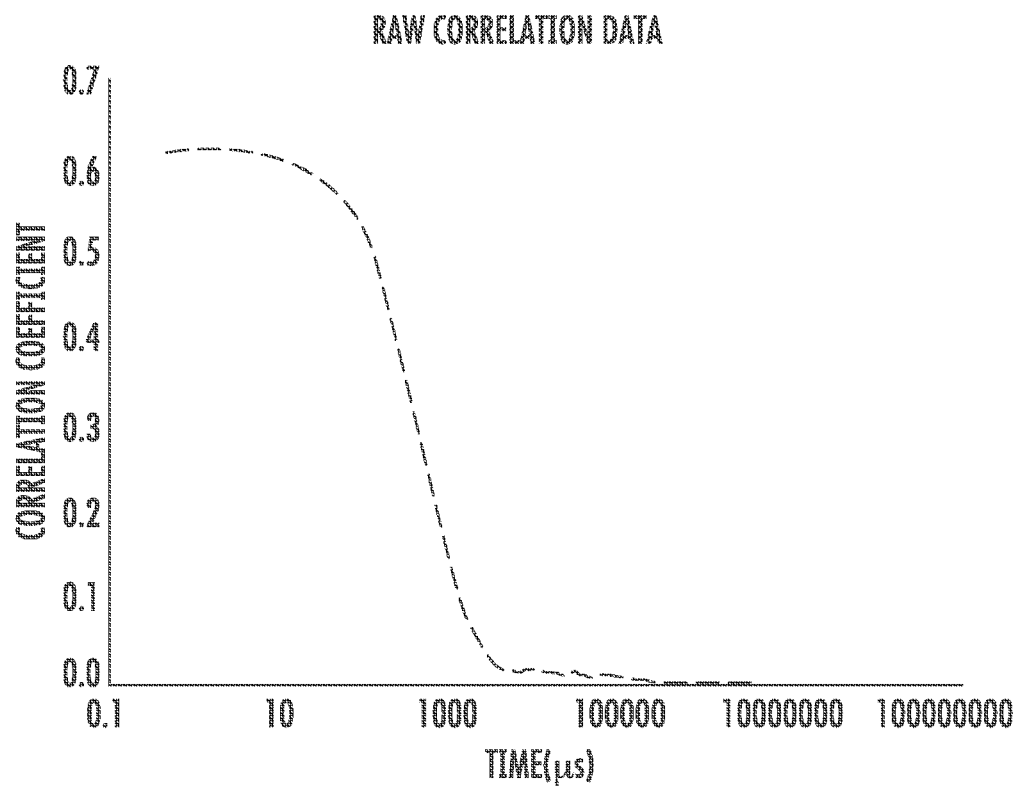
FIGS. 1 and 2 are respectively a correlogram and an intensity size distribution for a DLS analysis of a sample of suspended crystals. The relaxation time is 1180 microseconds. Z-ave is 403 nm, and the PdI is 0.364.

A. Overview of the compositions comprising crystals of 4-methyl-5-(pyrazin-2-yl)-3H-1,2-dithiole-3-thione The disclosure provides crystals of 4-methyl-5-(pyrazin-2-yl)-3H-1,2-dithiole-3-thione ("oltipraz") having a MHD of from 30 to 2000 nm. The disclosure also provides compositions comprising such crystals (i.e. compositions comprising a quantity of such crystals), and methods for the production of such crystals and compositions comprising them.

As noted above, the compositions and methods of this disclosure relate to crystals of 4-methyl-5-(pyrazin-2-yl)-3H-1,2-dithiole-3-thione having an MHD in the range of from 30 to 2000 nm, such as from 30 to 1200 nm, e.g. 100 to 600 nm, 400 to 700 nm, 400 to 600 nm, preferably 150 to 450 nm, 400 to 700 nm, 400 to 600 nm or 450 to 550 nm.

Certain embodiments of the compositions and methods described herein comprise a quantity of crystals of 4-methyl-5-(pyrazin-2-yl)-3H-1,2-dithiole-3-thione having an MHD in the range of from 30 to 100, 100 to 200 nm, with embodiments having MHD's within target ranges of from 30 to 100, 100 to 1200 nm, 150 to 600 nm, 150 to 450 nm, 400 to 700 nm, 400 to 600 nm or 450 to 550 nm. The MHD of the crystals may be measured in any number of ways known to skilled artisans, including dynamic light scattering as described herein. As mentioned above, the compound 4-methyl-5-(pyrazin-2-yl)-3H-1,2-dithiole-3-thione, also known as oltipraz, can be prepared in crystalline form. Embodiments of the crystal compositions provided herein, however, have been found to provide dry compositions of oltipraz crystals that are stable for extended periods, and which are able to be readily re-suspended in aqueous compositions to form substantially homogeneous dispersions of oltipraz crystals that exhibit substantially improved properties as compared to the previously available crystalline form.

The oltipraz crystals in the compositions described herein typically also exhibit substantially increased rate of dissolution and solubility in water, e.g., at 20° C., as compared to oltipraz crystals prepared from standard methods (e.g., ranging from 20 μm to 200 μm or greater). For example, the oltipraz crystals in the compositions of this disclosure typically have a solubility in water at 20° C. between 100 and about 250% that of crystals of oltipraz, prepared from recrystallization and having diameters of 20 to 200 μm. More typically, oltipraz crystals in the compositions of this disclosure have a solubility of from about 130 to about 220%, such as from about 160% to about 200% e.g. from about 170 to about 190% that of oltipraz crystals of 20 to 200 μm in diameter.

As discussed in Example 5 below, the solubility of oltipraz in water at 20° C. in certain embodiments of compositions disclosed herein is almost double that of the larger oltipraz crystals (e.g., a >80% increase). Solubility values of >3.5 μg/ml, >4.0 μg/ml, >4.5 g/ml, >5.0 μg/ml and >5.5 g/ml are all possible, including, e.g., about 5.1 μg/ml, about 5.2 μg/ml, about 5.3 μg/ml, about 5.4 μg/ml, about 5.5 μg/ml, about 5.6 μg/ml, and about 5.7 μg/ml. Hence, solubility values in water at 20° C. in the following exemplary ranges are possible: 3.5 μg/ml to 8.0 μg/ml, 3.5 μg/ml to 7.0 μg/ml, 3.5 μg/ml to 6.0 μg/ml, 3.5 μg/ml to 5.7 μg/ml, 4.0 μg/ml to 8.0 μg/ml, 4.0 μg/ml to 7.0 μg/ml, 4.0 μg/ml to 6.0 μg/ml, 4.0 μg/ml to 5.7 μg/ml, 4.5 μg/ml to 8.0 μg/ml, 4.5 μg/ml to 7.0 μg/ml, 4.5 μg/ml to 6.0 μg/ml, 4.5 μg/ml to 5.7 μg/ml, 5.0 μg/ml to 8.0 μg/ml, 5.0 μg/ml to 7.0 μg/ml, 5.0 μg/ml to 6.0 μg/ml, 5.0 μg/ml to 5.7 μg/ml, 5.5 μg/ml to 8.0 μg/ml, 5.5 μg/ml to 7.0 μg/ml, 5.5 μg/ml to 6.0 μg/ml, 5.5 μg/ml to 5.7 μg/ml, 6.0 μg/ml to 6.5 μg/ml, 6.0 μg/ml to 7.0 μg/ml, 6.0 μg/ml to 8.0 μg/ml, 6.5 μg/ml to 7.0 μg/ml, 6.5 μg/ml to 8.0 μg/ml, 7.0 μg/ml to 8.0 μg/ml, and greater than 8.0 μg/ml.

Typically, therefore, the oltipraz crystals in the compositions of this disclosure have a solubility in water at 20° C. of from about 3.5 to about 8 μg/ml, more typically from about 4 to about 7.5 μg/ml, such as from about 4.5 to about 7 μg/ml e.g. from about 5 to about 6.5 μg/ml such as from about 5.5 to about 6 μg/ml, e.g. about 5.7 μg/ml.

Liquid compositions of oltipraz have a strongly bitter flavor that can elicit aversion, revulsion, nausea, gagging and/or vomiting when administered to patients. As noted above, the oltipraz crystals in the compositions of this disclosure exhibit nearly twice the solubility of other crystalline oltipraz compositions. The dissolution rate, solubility, and bioavailability are thus substantially improved, but these changes also increase exposure of the oltipraz to the taste receptors, thereby rendering such composition substantially more unpalatable. Pharmaceutical compositions comprising crystalline compositions as described herein are thus substantially more unpalatable and difficult to flavor as compared with other crystalline oltipraz compositions. Moreover, as discussed below, patients who have oral mucositis typically have significantly altered sensations of taste that render them very sensitive to certain flavors, making the liquid oltipraz compositions not only unpalatable, but rendering such compositions with flavoring additives equally or even more unpalatable and more intolerable. This disclosure therefore provides liquid compositions comprising the crystalline compositions described above together with taste-modifying additives to provide pharmaceutical compositions that have greatly improved palatability and can be tolerated by many patients when taken orally, including patients with mucositis, including oral mucositis, including moderate to severe oral mucositis.

The crystals of this disclosure can be prepared by processing oltipraz into crystals having the desired size range using processes as described below. In some circumstances, once the desired size is attained, however, the crystals in aqueous or other liquid solution will tend to grow larger over time, e.g., by agglomerating and/or recrystallizing to form larger crystals. Hence, in instances where it is desired to prevent the crystals from growing larger for a period of time, at least one stabilizing agent may be added to the composition in order to help maintain the crystals in the desired size range in the liquid solution.

Typically, the stabilizing agent is a polymer, which may be used alone or in combination with one or more other stabilizing agents such as surfactants, to stabilize the individual crystals by inhibiting and/or preventing, for at least a period of time, the formation of larger crystals, e.g., through agglomeration, ripening (e.g. Ostwald ripening), and/or recrystallization. In certain embodiments, the polymer can be a polymer that comprises charged moieties. In other embodiments, the polymer may be neutral. Sometimes, one or more surfactants may be employed as stabilizing agents, either alone or together with a polymer. Various polymers and/or surface active molecules can have an affinity for the oltipraz crystal surface, e.g., such that they can coat, adsorb, adhere or otherwise associate with all or a portion of the crystals and thereby interfere with the crystals agglomerating, ripening, and/or recrystallizing to form larger crystals.

As noted above, the quantity of crystals in the liquid suspension then may be further treated to produce a dry composition, e.g., by mixing a bulking agent with a liquid composition of crystals and then removing the liquid from the composition to form a dry composition, e.g., by spray-drying or lyophilizing an aqueous composition. The bulking agent can also serve as a stabilizing agent, either alone or in combination with other stabilizing agents. When a bulking agent is used, the dry composition thus will comprise both the crystalline drug and the bulking agent, as well as any other stabilizing agents or other ingredients that are present in the liquid composition prior to the removal of the water and/or other liquid solvent. When the dry composition is then mixed with liquid (e.g., water), the drug crystals and other ingredients present in the dry composition will then be released into the liquid.

The term "dry composition" as used herein refers to a composition that substantially excludes water or other solvent. As used in this disclosure, the term "substantially" is intended to encompass both "wholly" and "largely but not wholly." Thus, a dry composition that substantially excludes water is a composition that wholly excludes water (and/or other solvent) or largely excludes water (and/or other solvent). That is, the dry composition either has no water or solvent, or at most only a small or residual amount of water or solvent such that the composition is not moist or wet.

B. Liquid Compositions Comprising Crystals in Suspension

Any suitable method can be used to produce the oltipraz crystals of this disclosure. For example, oltipraz crystals can be wet milled in the presence of at least one stabilizing agent that can help to stabilize the drug crystals to reduce or prevent the growth of crystals by agglomeration, ripening and/or recrystallization. The wet milling of oltipraz crystals in the presence of the stabilizing agent thus creates a liquid (e.g., aqueous) composition comprising the oltipraz crystals in suspension in the composition. Combinations of stabilizing agents may be added to the wet milling composition to facilitate stabilization of the crystals.

Alternatively, the oltipraz crystals may be made by other methods of producing nanocrystals, e.g., by antisolvent precipitation, supercritical fluid precipitation, printing techniques adapted from the semiconductor industry, or three dimensional printing or other known means of producing nanoparticles.

For example, a liquid composition comprising at least a portion of the crystals of this disclosure and optionally other additives, e.g., from a wet milling or antisolvent process, can be admixed with a bulking agent to form a liquid composition comprising the bulking agent and crystals in suspension. In certain embodiments, a liquid composition comprising at least a portion of the crystals and other additives, e.g., from a wet milling or antisolvent process, is then admixed with a bulking agent to form a liquid composition comprising the bulking agent and crystals in suspension. That liquid composition then may be processed to remove the liquid, e.g., by spray-drying or lyophilization in the case of aqueous solutions, and additional drying if necessary, to form a dry composition that substantially excludes water. Other processes known to persons skilled in the art also may be used to prepare dry compositions comprising the crystals. For example, the liquid composition can be sprayed onto sugar spheres or beads for drying. When dry, the sugar spheres or beads become a dissolvable carrier for the drug and other additives, e.g., the stabilizing agent(s) and/or bulking agent(s). The dry composition thus comprises the oltipraz crystals and any ingredients other than the liquid solvent (e.g., water) that were present in the liquid composition. The dry composition can be then later admixed with a liquid comprising water, at which time the bulking agent can facilitate release of the crystals to again form an aqueous composition comprising such crystals in suspension. Any additional nonvolatile ingredients present in the liquid composition prior to removal of water or other solvent will be carried along in the dry composition and also released into the re-suspended aqueous composition.

Depending on the amount of water and/or other liquid solvent used in the milling or other nanocrystal production process such as antisolvent precipitation, the oltipraz crystals can be present in an amount ranging from 2% or less to 40% or more by weight of the liquid composition prior to the addition of any bulking agent. Within that range are included the following ranges in percent by weight of 1-20%, 2 to 5%, 5 to 10%, 10 to 15%, 10 to 20%, 15 to 20%, 15 to 25%, 15 to 30%, 20 to 30%, 25 to 35%, 30 to 40%, or more than 40%. In some embodiments, the crystals can be between 6 and 11% by weight of the liquid composition, e.g., between 7 and 10%. In certain such embodiments, the concentration of the crystals in the liquid is about 1% to about 30% by weight, about 4% to about 15% by weight, about 5% to about 10% by weight, about 6% to about 10% by weight, about 6% to about 12% by weight, about 7% to about 10% by weight, about 8% to about 10% by weight, or about 8.6% by weight of the suspension. Accordingly, the liquid composition typically comprises between about 1 to about 40 wt %, such as from about 2 to about 20 wt %, e.g. from about 4 to about 15 wt %, typically from about 6 to about 12 wt % such as from about 7 to about 10 wt % e.g. about 8 to about 9 wt % such as about 8.6 wt % of oltipraz crystals, based on the weight of the liquid composition prior to the addition of any bulking agent.

Alternatively, the amount of crystals can be calculated as a percent of the components other than the water or other liquid solvent in the composition prior to addition of a bulking agent. As a percent of the non-solvent components, the crystals can be present in an amount ranging less than 10% up to more than 60% by weight of the non-solvent components prior to the addition of any bulking agent. Within that range are included the following ranges in percent by weight of 1 to 5%, 5 to 10%, 10 to 15%, 15 to 20%, 20 to 30%, 25 to 40%, 30 to 40%, 40 to 50%, 50 to 60%, 60 to 70%, and over 70%. In certain embodiments, the crystals comprise between 30 and 70%, e.g., between 50 and 65%, or between 55 and 60%, or about 57% by weight of the non-solvent components prior to addition of any bulking agent. Accordingly, the non-solvent components in the composition typically comprise from about 1 to about 70 wt % oltipraz crystals based on the overall weight of the non-solvent components in the composition; more typically the non-solvent components comprise from about 30 to about 65 wt % such as from about 50 to about 60 wt % e.g. from about 55 to about 58 wt % such as about 57 wt % of the composition based on the overall weight of the non-solvent components in the composition.

Once a bulking agent is added, the percentage by weight of the oltipraz crystals typically will decrease. Within the liquid composition before removal of water or other liquid solvent but after addition of the bulking agent, the crystals may comprise from 1% up to 10% or more of the liquid composition. Within such ranges are, e.g., 1 to 2%, 1 to 3%, 2 to 3%, 2 to 4%, 2 to 5%, 2 to 6%, 3 to 5%, 3 to 6%, 3 to 7%, 4 to 7%, 4 to 8%, 5 to 9% and 6 to 10%. In some embodiments, the crystals can comprise between 2 and 6% of the liquid suspension comprising the bulking agent, e.g., between 3 and 5%, or about 4%. In certain such embodiments, the concentration of the crystals in the liquid is about 0.1% to about 4% by weight, about 0.2% to about 3.5% by weight, about 0.5% to about 3.5% by weight, about 1% to about 3.5% by weight, about 1.5% to about 3% by weight, about 2% to about 3% by weight, or about 2.5% by weight of the formulation. Accordingly, the concentration of oltipraz crystals in the liquid is typically from about 0.1 to about 10 wt % (based on the weight of the liquid composition before removal of water or other liquid solvent but after addition of a bulking agent if present), more often from about 0.5 to about 8 wt % e.g. from about 1 to about 6 wt % such as from about 2 wt % to about 5 wt % such as from about 2.5 wt % to about 4 wt %.

Alternatively, the amount of the crystals can be calculated as a percent of the non-solvent (e.g., non-water) components following addition of a bulking agent. This percentage of oltipraz in the non-solvent components also may be referred to as the "drug loading" percentage because it represents the amount of the oltipraz crystals in the dry composition. As a percent of the non-solvent components, i.e., the solids, the oltipraz crystals can be present in an amount ranging from less than 2% up to 25% or more. Within that range are included the following ranges in percent by weight of 0.5 to 1%, 1% to 2%, 2 to 4%, 3 to 5%, 4 to 7%, 5 to 8%, 5 to 10%, 6 to 8%, 6 to 9%, 6 to 10%, 7 to 11%, 7 to 12%, 8 to 12%, 8 to 13%, 9 to 13%, 9 to 14%, 10 to 15%, 11 to 16%, 12 to 17%, 13 to 18%, 14 to 19%, 15 to 20% and 20 to 25%. Accordingly, the oltipraz crystals are typically from about 0.5 to about 25 wt % (based on the weight of the non-solvent components after addition of a bulking agent if present), more often from about 1 to about 25 wt % such as from about 5 to about 20 wt % e.g. from about 6 to about 19 wt %, such as from about 10 to about 18 wt % e.g. about 15 to about 17 wt % such as about 16 wt % (e.g. about 16.7 wt %). The crystals can comprise between about 5% and about 10% by weight of the non-solvent components, e.g., between about 6% and about 9%, such as about 7%. For example, in certain embodiments the crystals can comprise between 5 and 10% by weight of the non-solvent components, e.g., between 6 and 9%, or about 7%. In other embodiments the crystals comprise between 10 and 20% by weight of the powder, e.g., between 13 and 17%. e.g., about 15% by weight of the non-solvent components.

In some embodiments, a dry composition comprising a drug loading of about 15% will provide good results when reconstituted with water, i.e., the dry composition quickly forms a dispersion (e.g., less than a minute) with moderate or gentle shaking, with the crystals substantially retaining their MHD from prior to drying. Typically, a dry composition comprising a drug loading of about 20% or higher provides less desirable results when reconstituted with water, i.e., the dry composition slowly forms a dispersion (e.g., several minutes) with moderate or vigorous shaking, and the dispersion may comprise larger particles, e.g., up to 2 microns in size. In such cases, it is advantageous to reduce the drug loading to a lower level that provides the desired characteristics in terms of rapidly forming a dispersion of crystals that retain their original MHD. Without being bound by any particular theory, it is believed that as the concentration of oltipraz crystals within the dry composition approaches 20%, there is less of the other ingredients in the composition (e.g., stabilizing agents and/or bulking agents) to separate the individual crystals, which in turn leads to more interactions between the crystals, resulting in slower formation of a dispersion in an aqueous or other solvent environment and also the formation of larger particles, e.g., by agglomeration. Hence, compositions comprising drug loadings of 12 to 20% a contemplated, including loadings of 12 to 13%, 12 to 14%, 12 to 15%, 13 to 14%, 13 to 15%, 13 to 16%, 14 to 15%, 14 to 16%, 14 to 17% 15 to 16%, 15 to 17%, 15 to 18%, 16 to 17%, 16 to 18%, 16 to 19%, 17 to 18%, 17 to 19%, 17 to 20%, 18 to 19%, 18 to 20%, including drug loadings of about 12%, about 13%, about 14%, about 15%, about 16%, about 17%, about 18%, about 19% and about 20% are all contemplated. Accordingly, the dry composition typically has a drug loading of about 12 to about 20 wt % such as from about 14 to about 18 wt % e.g. from about 15 to about 17 wt % such as about 16 or about 16.7 wt %.

Stabilizing Agents

As mentioned above, liquid compositions comprising the oltipraz crystals of this disclosure typically also comprise one or more stabilizing agents to stabilize the crystals. In some circumstances, in the absence of at least one stabilizing agent (or a combination of agents that together act to stabilize), over time oltipraz crystals in liquid suspension can agglomerate, ripen, and/or recrystallize to form larger crystals. It is typically desirable to maintain the crystals in the size range that results from the wet milling, antisolvent precipitation or other crystal-production processes for a period of time, e.g., to permit storage of the materials prior to the next step in processing, or to allow testing or validation of crystal size or some other feature of a batch of oltipraz crystals. In such instances, at least one stabilizing agent may be provided to the liquid composition of crystals, e.g., during and/or after milling, or during and/or after antisolvent precipitation, in order to stabilize the crystals to thereby prevent and/or inhibit the milled crystals from agglomerating, recrystallizing and/or ripening to form larger crystals. Thus, any agent that either alone or in combination with another agent serves to stabilize the crystals to thereby prevent and/or inhibit the milled crystals from agglomerating, recrystallizing and/or ripening to form larger crystals, is deemed a stabilizing agent. If a combination of two or more agents is used to stabilize crystals, then each of the two or more co-stabilizers is deemed to be a stabilizing agent even though an individual agent within the combination may be unable to stabilize the crystals by itself, or unable to stabilize the crystals by itself for the desired length of time.

Alternatively, if the oltipraz crystals are to be quickly converted to a dry form, e.g., by mixing with a bulking agent and being spray-dried or lyophilized, a stabilizing agent may be unnecessary. This may be an acceptable alternative if the intended method of administration does not require the oltipraz crystals to later have stability upon resuspension in water, e.g., if the resuspension will occur immediately before administration of the dry composition, e.g., in pill or tablet form. Alternatively, a single agent such as copovidone or PVP-VA64 (polyvinylpyrrolidone vinyl acetate, a copolymer of 1-vinyl-2-pyrrolidone and vinyl acetate in a ratio of 6:4 by mass, commercially available e.g. from BASF as Product No. 95405-2-43), may be able to serve both as a stabilizing agent and as bulking agent, thereby rendering additional stabilizing agents unnecessary and providing a composition that will exhibit stability upon resuspension in water and/or other liquid.

Generally speaking, stabilizing agents are surface active agents that affect the surface of the crystals in some way. While not wishing to be bound to a particular theory by which a stabilizing agent can operate to stabilize the crystals, it is believed that the stabilization typically can take one of two forms. Steric stabilization can be accomplished by mixing the crystals with either an amphiphilic or water-soluble material that interacts with the crystal surface, which keeps crystal faces from interacting by providing a barrier between crystals. This is typically accomplished by addition of polymer, surfactant, or both. Alternatively, electrostatic stabilization can be accomplished by modifying the crystal surface with a charge through addition of a charged compound (polymer, surfactant, or other interacting charged molecule or ion). Because all or at least many of the crystals then carry the same charge, in theory they repel each other, thereby increasing the energy barrier required for two crystal faces to get close enough to fuse together.

Typically, the stabilizing agent maintains the size of the crystals in the liquid composition within a specified size range for a period of time following wet milling. Such a period can be on the order of hours, e.g., at least 1 hour, at least 6 hours, at least 12 hours, at least 24 hours, at least two days, at least three days, at least a week, at least two weeks, at least a month, at least two months, and at least six months, or longer.

Typically, the stabilizing agent comprises a polymer that is either neutral or capable of associating charged moieties with the individual milled oltipraz crystals, e.g., by coating the crystals, or adsorbing or otherwise associating with them. Such polymers thus may be neutral or may include moieties that provide either a positive or negative charge to the polymer, and in that way the charged moieties associated with the crystals may be able to repel other crystals having like charges on their surfaces. Nonionic, cationic or anionic polymers may be used as stabilizing agents, including especially pharmaceutically acceptable nonionic, cationic and anionic polymers. Combinations of such polymers also may be employed. Sometimes, the stabilizing agent may comprise a carbohydrate and/or protein, e.g., albumin.

The polymer may be an acrylate polymer comprised of a plurality of repeat units derived from identical or different monomers. Acrylate polymers comprising different types of repeat units are referred to herein as "copolymers". Exemplary repeat units of acrylate polymers include repeat units derived from methacrylate, alkyl acrylate (such as methyl acrylate or ethyl acrylate), hydroxyethyl methacrylate, ethylacrylate, butyl methacrylate, acrylonitrile, or alkyl cyanoacrylates. Typically, when the carboxylic acid functionality of acrylate is not protected as an ester, the acid can exist as a protonated carboxylic acid (—COOH) or as an anionic salt (e.g., —COONa).

The polymer also may be an acrylate- and alkenyl ether-based co-polymer (e.g., Carbopol® type polymers such as Carbopol 974P NF), polyvinylpyrrolidine (e.g., PVP K15 or K30), a cellulosic polymer such as a cationic hydroxyethyl cellulose (e.g., in the Polymer JR family), hydroxypropylcellulose (HPC e.g. HPC EF typically having a molecular weight of about 80 kDa), or hydroxypropyl methylcellulose (HPMC e.g. HMPC E3 typically having viscosity of about 3 cP at 2% in water), or hydroxypropyl methylcellulose acetate succinate, HPMCAS. The polymer also may be a copovidone (e.g., PVP-VA64), poly(ethylene oxide), or a poloxamer (e.g., a poly(propylene oxide) and poly(ethylene oxide) copolymer). The polymer also may be an acrylamide polymer. For example, the polymer may be comprised of repeat units derived from acrylamide.

The repeat units can be functionalized by adding groups that can change the permeability, hydrophobicity, or other properties of the formulation. For example, certain repeat units can be functionalized by tertiary amines or by quaternary amines, such as quaternary trialkylammonium substituents.

An acrylate polymer may be comprised of repeat units derived from a methacrylate monomer. In certain embodiments, the acrylate polymer comprises repeat units derived from an acrylate monomer and repeat units derived from a methacrylate monomer. Typically, the acrylate polymer comprises repeat units derived from ethyl acrylate and repeat units derived from methyl methacrylate. Typically, some of the ethyl acrylate monomeric units are functionalized on the ethyl group by a trimethylammonium chloride group. The acrylate polymer of the crystal may be poly(ethyl acrylate-co-methyl methacrylate-co-trimethylammonioethyl methacrylate chloride) 1:2:0.2. Poly(ethyl acrylate-co-methyl methacrylate-co-trimethylammonioethyl methacrylate chloride) 1:2:0.2 may be sold as EUDRAGIT® RL. Other polymethacrylate-based copolymers in the Eudragit family may be used, e.g., Eudragit S, L, E or RS.

Typically, the polymer is one or more of an acrylate- and alkenyl ether-based co-polymer, polyvinylpyrrolidone, hydroxypropylcellulose, hydroxypropyl methylcellulose, a copovidone such as PVP-VA64, and a polymethacrylate-based copolymer such as EUDRAGIT® RL. More often, the polymer is one or more of a copovidone such as PVP-VA64 and a polymethacrylate-based copolymer such as EUDRAGIT® RL.

Alternatively, or in addition to the above polymers, other surface active ingredients may be added to the liquid compositions that comprise the crystals for the purpose of helping to stabilize the crystals in suspension. In addition to helping stabilize the crystals such surfactants also may aid in the dispersion of crystals and/or other ingredients in a particular liquid composition. Indeed, such surfactants may be added solely for the purpose of aiding in the dispersion of crystals and/or other ingredients in the liquid compositions described herein that are prepared from the dry compositions described herein.

Surfactants suitable for use in the compositions described herein may be ionic or non-ionic. These include, but are not limited to: sodium isostearate, cetyl alcohol, polysorbates (Polysorbate 20, Polysorbate 40, Polysorbate 60, Polysorbate 80), steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, methylbenzethonium chloride, dicetyl phosphate, ceteth-10 phosphate (ceteth-10 is the polyethylene glycol ether of cetyl alcohol where n has an average value of 10; ceteth-10 phosphate is a mixture of phosphoric acid esters of ceteth-10), ceteth-20. Brij S 10 (polyethylene glycol octadecyl ether, average $M_n$~711), PEG-20 phytosterol, and Poloxamers (including, but not limited to, Poloxamer 188 $(HO(C_2H_4O)_a(CH(CH_3)CH_2O)_b(C_2H_4O)_aH$, average molecular weight 8400) and Poloxamer 407 $(HO(C_2H_4O)(CH(CH_3)CH_2O)_b(C_2H_4O)_aH$, wherein a is about 101 and b is about 56)). Poloxamers are nonionic triblock copolymers composed of a central hydrophobic chain of polyoxypropylene (poly(propylene oxide)) flanked by two hydrophilic chains of polyoxyethylene (poly(ethylene oxide)). Poloxamer surfactants, also sold under the trade name of Pluronic surfactants, thus may be employed, e.g., Pluronic F-68, which also is known as Poloxamer 188. The surfactants that may be used in the formulation may be non-ionic surfactants such as polyoxyethylene glycol alkyl ethers (e.g., octaethylene glycol monododecyl ether, pentaethylene glycol monododecyl ether, and polyethylene glycol alkyl ethers such as Brij® Detergents), polyoxypropylene glycol alkyl ethers, glucoside alkyl ethers (e.g., decyl glucoside, lauryl glucoside, or octyl glucoside), polyoxyethylene glycol alkylphenol ethers (e.g. Triton X-100, Nonoxyol-9), glycerol alkyl esters, polyoxyethylene glycol sorbitan alkyl esters (e.g., polysorbates), sorbitan alkyl esters, cocamides, and Poloxamers (mentioned above). In certain embodiments, the non-ionic surfactant may be polyoxyethylene (20) sorbitan monooleate (polysorbate 80). Polysorbate 80 is available under the tradename Tween 80.

Typically, the surfactant is one or more of poloxamers such as Pluronic F-68 (i.e., Poloxamer 188), polysorbates such as polysorbate 80 (Tween 80), povidone based polymers, lecithin, PEG-castor oil derivatives, TPGS, bile acids, tyloxapol, acacia, and sodium lauryl sulfate. More typically, the surfactant is polysorbate 80 (Tween 80).

As described in more detail below, appropriate combinations or mixtures of surfactants such as those above may also be used, either with or without out other stabilizing agents such as the polymers described above. For example, in certain embodiments the stabilizing agents can comprise a combination of a neutral polymer and a neutral surfactant, a cationic polymer and a neutral surfactant, or a neutral polymer and an anionic surfactant. As noted above, however, such stabilizing agents may be unnecessary when the bulking agent also acts as a stabilizing agent or when no stabilizing agent is desired.

When such stabilizing agents are employed, then depending on the amount of water and/or other solvent used in the milling process, the stabilizing agent(s) can be present in an amount ranging from less than 1 percent to 25% or more by weight of the liquid composition prior to the addition of any bulking agent. Within that range are included the following ranges in percent by weight of 0.1 to 1%, 1 to 3%, 3 to 7%, 5 to 10%, 5 to 15%, 5 to 20%, 10 to 15%, 10 to 20%, 10 to 25%, 15 to 20%, 15 to 25%, 7.5 to 25%, or more than 25%. In some embodiments, the stabilizing agent(s) can comprise between 2 and 10%, e.g., between 4 and 8% or about 6.4%. Accordingly, the amount of stabilizing agent(s) in the liquid composition prior to addition of any bulking agent is typically from about 0.1 to about 25 wt % such as from about 1 to about 20 wt % such as from about 2 to about 10 wt % e.g. from about 4 to about 8 wt % such as from about 5 to about 7 wt % e.g. about 6 wt % such as about 6.4 wt %.

Alternatively, the amount of stabilizing agent can be calculated as a percent of the non-solvent components prior to addition of a bulking agent. As a percent of the non-solvent components, the stabilizing agent can be present in an amount ranging from 10 percent or less to 75% or more by weight of the non-liquid components prior to the addition of any bulking agent. Within that range are included the following ranges in percent by weight of 0.1 to 10%, 10 to 20%, 20 to 30%, 30 to 40%, 40 to 50%, 50 to 60%, 60 to 75% or more. In some embodiments, the stabilizing agent can be between 30 and 55% by weight of the non-solvent components, e.g., between 35 and 50%, or between 40 and 45%, or about 42.7%. Accordingly, the amount of stabilizing agent(s) in the composition prior to addition of any bulking agent is typically from about 1 to about 75 wt %, such as from about 10 to about 60 wt % such as from about 20 to about 55 wt % e.g. from about 30 to about 50 wt % such as from about 40 to about 45 wt % e.g. about 42 wt % such as about 42.7 wt %, based on the weight of non-solvent components.

Once a bulking agent is added, the percentage by weight of the stabilizing agent(s) typically will decrease. Within the liquid composition before removal of water and/or other liquid solvent, following addition of a bulking agent the stabilizing agent(s) may comprise from less than 1% up to 30% or more of the liquid composition, again depending on the amount of water or other solvent in the composition prior to a water removal step. Within such ranges are, e.g., 0.5 to 1%, 1 to 2%, 1 to 3%, 2 to 3%, 2 to 4%, 2 to 5%, 3 to 6%, 3 to 7%, 4 to 7%, 4 to 8%, 5 to 9% and 6 to 10%, 10 to 15%, 15 to 20%, 20 to 25%, 25 to 30% and more than 30%. In some embodiments, the stabilizing agent(s) can comprise between 1 and 5% by weight of the liquid suspension comprising the bulking agent, e.g., about 2 to 4%, or about 3.1%. Accordingly, the amount of stabilizing agent(s) in the liquid composition (based on the weight of the liquid composition before removal of water or other liquid solvent but after addition of a bulking agent if present), is typically from about 0.1 to about 30 wt %, such as from about 1 to about 10 wt % such as from about 2 to about 5 wt % e.g. from about 3 to about 4 wt % such as about 3.1 wt %.

Alternatively, the amount of stabilizing agent(s) can be calculated as a percent of the non-solvent components following addition of a bulking agent. As a percent of the non-liquid components, the stabilizing agent(s) can be present in an amount ranging from less than 2% up to 20% or more. Within that range are included the following ranges in percent by weight of 2 to 4%, 3 to 5%, 4 to 7%, 5 to 8%, 5 to 10%, 6 to 8%, 6 to 9%, 6 to 10%, 7 to 11%, 7 to 12%, 8 to 12%, 8 to 13%, 9 to 13%, 9 to 14%, 10 to 15%, 11 to 16%, 12 to 17%, 13 to 18%, 14 to 19% and 15 to 20%, and more than 20%. For example, in certain embodiments the stabilizing agent can comprise between 5 and 15% by weight of the non-solvent components, e.g., between 9 and 13%, or about 11.2%. Such amounts will also correspond to the amounts of the stabilizing agent in the dry composition. Accordingly, the amount of stabilizing agent(s) in the composition (based on the weight of non-solvent components after addition of a bulking agent if present), is typically from about 2 to about 20 wt %, such as from about 4 to about 17 wt % such as from about 8 to about 15 wt % e.g. from about 10 to about 12 wt % such as about 11 wt % e.g. about 11.2 wt %.

Combinations of Stabilizing Agents

As noted above, combinations of stabilizing agents may be employed to assist in stabilizing the crystals in a liquid composition and/or assist in dispersing the crystals from a dry composition. For example, as noted above, in certain embodiments, nonionic surfactants may be combined with a cationic polymer or an anionic polymer. In other embodiments, an ionic surfactant (anionic or cationic) is combined with a neutral polymer. Other embodiments can combine a neutral polymer and nonionic surfactant.

Some exemplary combinations include, with or without an anti-foaming agent such as simethicone, (i) Eudragit RL in combination with Tween 80, Pluronic F-68 and/or sodium lauryl sulfate, (ii) Carbopol 974P NF RL in combination with Tween 80, Pluronic F-68 and/or sodium lauryl sulfate. (iii) PVP (K15 or K30) RL in combination with Tween 80, Pluronic F-68 and/or sodium lauryl sulfate, (iv) HPC EF RL in combination with Tween 80, Pluronic F-68 and/or sodium lauryl sulfate, and (v) HPMC E3 RL in combination with Tween 80, Pluronic F-68 and/or sodium lauryl sulfate. Some examples of such combinations are illustrated in Table 1 below.

TABLE 1

| Components | | Formulation Composition (mg/mL) | | | | | |
|---|---|---|---|---|---|---|---|
| Function | Name | 1 | 2 | 3 | 4 | 5 | 6 |
| API | Oltipraz | 50 | 50 | 50 | 50 | 50 | 50 |
| Stabilizing Agent (Polymer) | Eudragit RL | 25 | | | | | |
| | Carbopol 974P NF | | 5* | | | | |
| | PVP (K15 or K-30) | | | 25 | | | |
| | HPC EF | | | | | 25 | 25 |
| | HPMC E3 | | | | 25 | | |
| Stabilizing Agent (Surfactant) | Tween 80 | 12.5 | | | 12.5 | | |
| | Pluronic F68 | | 12.5 | 12.5 | | 12.5 | |
| | SLS | | | | | | 12.5 |
| Anti-foam | Simethicone | 0.5 | 0.5 | 0.5 | 0.5 | 0.5 | 0.5 |

*Added after milling

Among the various combinations. Eudragit RL in combination with Tween 80 or HPC EF in combination with Tween 80 have been found by the Inventors to provide acceptable results and typically to be particularly beneficial in terms of forming and keeping small crystals stable for a period of time. As discussed below, other combinations of the foregoing polymers and surfactants may be suitable depending on the particular composition and method of administration. The amounts of the individual components in such combinations are as set forth above for the individual components.

Other Surface Active Agents

As noted above, surface active agents, including those listed above, may be added to the liquid compositions described herein for purposes other than stabilizing oltipraz crystals, e.g., to aid in the dispersion of crystals upon resuspension with water and/or other liquid, or to serve other purposes beyond stabilizing the crystals, e.g., emulsifiers and anti-foam agents. For example, such ingredients can be added for the purpose of improving processes and/or compositions such as the processes for making the crystals or the properties of the composition comprising crystals.

In certain embodiments, e.g., an emulsifier may be added. Suitable emulsifiers include, but are not limited to, *glycine soja* protein, sodium lauroyl lactylate, polyglyceryl-4 diisostearate-polyhydroxystearate-sebacate, behentrimonium methosulfate-cetearyl alcohol, non-ionic emulsifiers like emulsifying wax, polyoxyethylene oleyl ether, PEG-40 stearate, carbomer, cetostearyl alcohol (cetearyl alcohol), ceteareth-12, ceteareth-20, ceteareth-25, ceteareth-30, ceteareth alcohol, Ceteth-20 (Ceteth-20 is the polyethylene glycol ether of cetyl alcohol where n has an average value of 20), oleic acid, oleyl alcohol, glyceryl stearate, PEG-75 stearate, PEG-100 stearate, and PEG-100 stearate, ceramide 2, ceramide 3, stearic acid, cholesterol, laureth-12, steareth-2, and steareth-20, or combinations/mixtures thereof, as well as cationic emulsifiers like stearamidopropyl dimethylamine and behentrimonium methosulfate, or combinations/mixtures thereof.

In certain embodiments, an anti-foam agent may be added. Anti-foam agents may be used to reduce the formation of foam, e.g., in the process of making the crystals. Anti-foam agents that may be used include, but are not limited to, oil-based anti-foam agents [e.g., a hydrophobic silica or a wax (e.g., paraffin, ester waxes, fatty alcohol waxes, ethylene bis(stearamide)) in mineral or vegetable oil], powder defoamers, water-based defoamers (e.g., long chain fatty alcohols, fatty acid soaps, or esters in a white oil or vegetable oil), silicone-based defoamers [hydrophobic silica in silicone oil], polyethylene glycol- or polypropylene glycol-based defoamers, or alkyl polyacrylates. In certain preferred embodiments, the anti-foam agent is a silicone-based anti-foam agent. In certain embodiments, the anti-foam agent is poly(dimethylsiloxane), or silicon dioxide (simethicone).

Depending on the amount of water and/or other liquid used in the milling process, prior to the addition of a bulking agent, such additional surface active ingredient(s) can be present in cumulative amounts ranging from less than 1 to more than 10% by weight of the liquid suspension. Within that range are included the following ranges in percent by weight, 0.1 to 1%, 1 to 3%, 1 to 4%, 1 to 5%, 2 to 5%, 2 to 6%, 3 to 6%, 3 to 7%, 4 to 7%, 4 to 8%, 5 to 8%, 5 to 9%, and 6 to 10%, and greater than 10%. For example, an anti-foam agent can be in an amount from about 0.01% to about 2% by weight of the liquid composition comprising the crystals, e.g. from about 0.01% to about 2%, from about 0.05% to about 1.5%, from about 0.1% to about 1%, from about 0.3% to about 0.9%, or from about 0.4% to about 0.8% by weight of the crystal. Typically, an anti-foam agent can be present in an amount from about 0.01% to about 2% by weight of the solid components (excluding bulking agents if present) in the liquid composition comprising the crystals, e.g. from about 0.01% to about 2%, such as from about 0.05% to about 1.5%, e.g. from about 0.1% to about 1%, such as from about 0.3% to about 0.9%, e.g. from about 0.4% to about 0.8% by weight of the crystal.

For example, a composition comprising oltipraz crystals of this disclosure may typically comprise a combination of solubilizing agents selected from (i) one or more of acrylate- and alkenyl ether-based co-polymers, polyvinylpyrrolidone, hydroxypropylcellulose, hydroxypropyl methylcellulose, a copovidone such as PVP-VA64, and a polymethacrylate-based copolymer such as EUDRAGIT® RL; and (ii) one or more of sodium lauryl sulfate, a poloxamer such as Pluronic F-68 and polysorbate 80. Another surface active ingredient may also be present such as an emulsifiers and/or an anti-foam agent. More typically the composition may comprise (i) one or more of a polymethacrylate-based copolymer such as Eudragit RL, an acrylate- and alkenyl ether-based co-polymer such as Carbopol 974P NF; a polyvinylpyrrolidone such as PVP (K15 or K-30); a hydroxypropylcellulose such as HPC EF and a hydroxypropyl methylcellulose such as HPMC E3; (ii) one or more of sodium lauryl sulfate, a poloxamer such as Pluronic F-68 and polysorbate 80; and optionally (iii) an antifoam agent such as poly(dimethylsiloxane) or silicon dioxide (simethicone). Still more typically the composition may comprise (i) one or more of a copovidone such as PVP-VA64 and a polymethacrylate-based copolymer such as EUDRAGIT® RL; (ii) polysorbate 80 (Tween 80); and optionally (iii) simethicone. In such compositions, the amount of component (i) is typically from about 5 to about 40 wt %, preferably from about 20 to about 35 wt % such as from about 25 to about 30 wt % based on the weight of solid components (excluding bulking agents) in the composition. The amount of component (ii) is typically from about 10 to about 20 wt %, preferably from about 12 to about 18 wt % such as from about 14 to about 15 wt % based on the weight of solid components (excluding bulking agents) in the composition. If present, the amount of component (iii) is typically from about 0.1 to about 1 wt %, preferably from about 0.3 to about 0.8 wt % such as from about 0.5 to about 0.7 wt % based on the weight of solid components (excluding bulking agents) in the composition.

Other Components

The liquid compositions described herein also can comprise liquids in addition to water. For example, the liquid may be an aqueous buffer solution. Pharmaceutically acceptable buffers include acetate (e.g., sodium acetate), sodium carbonate, citrate (e.g., sodium citrate), tartrate, glycylglycine, histidine, glycine, lysine, arginine, sodium dihydrogen phosphate, disodium hydrogen phosphate, sodium phosphate, and tris(hydroxymethyl)-aminomethane or mixtures thereof. Alternatively, the compositions described herein as aqueous compositions may be instead prepared in a liquid solvent other than one that contains water, e.g., a polar organic solvent, such as methanol and/or ethanol. If liquids other than water are used, then advantageously, the liquid is one in which oltipraz is not more than minimally soluble, e.g., not more than 0.35%, 0.1%, 0.05%, 0.01%, 0.005%, 0.001%, or 0.0008% by weight solvated oltipraz in solvent. Typically, therefore, if liquids other than water are used, then advantageously, the liquid is one in which oltipraz is not more than minimally soluble, e.g., the liquid does not support more than 0.35%, e.g. not more than 0.1%, such as not more than 0.05%, e.g. not more than 0.01%, such as not more than 0.005%, e.g. not more than 0.001% or 0.0008% by weight solvated oltipraz in solvent. Combinations of liquids also may be used, including combinations of water and other liquids such as one or more polar organic solvents. Hence, although it is contemplated that aqueous compositions can be used throughout this disclosure, it is also contemplated that the water component in any of the aqueous compositions described herein could be replaced in whole or in part by a liquid other than water. Where a solvent other than or in addition to water is used, the percentages given above for the stabilizing agents and other ingredients typically remain the same or substantially the same.

Liquid compositions described herein, e.g., aqueous or otherwise, may be useful for milling. Other liquid compositions described herein may be useful for spray-drying or lyophilization-based methods of generating the crystals in a dry composition. The total concentration of ingredients in such liquid formulations may be represented by the percentage by weight of combined solids in the formulation, wherein the combined solids are the non-solvent components, e.g., the crystals and any additives such as a stabilizing agent, surfactant, and/or a bulking agent that remain once the solvent is removed. The appropriate level of solids in a liquid composition as described herein can vary depending on the use of the composition. For example, the total solids in a composition that is undergoing wet milling may be higher or lower than the total solids in a composition that also comprises a bulking agent and is undergoing a process in which liquid is being removed, e.g., spray-drying or lyophilization. In certain embodiments, for example including compositions for milling and/or spray-drying or lyophilization, the concentration of the solids in the liquid described herein can be about 5% to about 35% or more by weight, including ranges of from 5 to 10%, 10 to 15%, 10% to 20%, 15 to 20%, 15 to 25%, 20 to 25%, 20 to 30%, 25 to 30%, 25 to 35%, or more than 35%. In some embodiments, the total solids can be about 12% to about 18% by weight, about 13% to about 18% by weight, about 14% to about 17% by weight, or about 16% by weight of the formulation. Typically, therefore, the total solids can be from about 12% to about 18% by weight, e.g. from about 13% to about 18% by weight, such as from about 14% to about 17% by weight, e.g. about 16% by weight of the formulation. Typically, in some liquid compositions for milling, the total solids can be from about 20 to 30% by weight, e.g., from about 22 to about 27% by weight, such as about 25% by weight. In some embodiments, e.g., in some liquid compositions for milling, the total solids can be from about 20 to 30% by weight, e.g., about 22 to 27% by weight, about 25% by weight. In some embodiments, e.g., spray-drying compositions, the total solids can be from about 25 to 30% by weight, e.g., about 28% by weight. Using the guidance provided herein, one of ordinary skill will be able to determine an acceptable level of solids for compositions described herein.

Crystal Sizes and Distribution, Such as Crystal Sizes and Distribution in Liquid Suspensions Due to the inherent variability of the wet milling or other crystal-forming process such as antisolvent precipitation, the individual crystals of oltipraz formed from such processes will typically vary in size, and thus a quantity of oltipraz crystals produced by such processes can typically be characterized by a distribution of crystals of varying sizes. When in an aqueous suspension, the quantity of crystals described herein generally will have a MHD of between 30 and 2000 nm. Generally speaking, larger crystals will tend to settle faster in aqueous compositions, and so quantities of smaller crystals, e.g., those having an MHD from 30 to 100 nm, or 100 to 600 nm, including from 40 to 80 nm, 40 to 60 nm, or from 150 to 450 nm, 400 to 700 nm, 400 to 600 nm, and 450 to 550 nm, often provide an advantage in terms of better suspension characteristics over time for an aqueous suspension of the crystals, e.g., the crystals will remain substantially completely suspended longer. Generally speaking, production of crystals by wet milling will have an MHD above 100 nm, although MHD values below 100 nm may be obtained with longer milling times and or different milling parameters. Methods such as antisolvent precipitation can produce crystal compositions having MHD values in ranges below 100 nm, e.g., 30-100 nm, 40-80 nm and 40-60 nm. Within the MHD range of 30 to 2000 nm are MHD ranges of from 30 to 100 nm, 40 to 80 nm, 40 to 60 nm, 100 to 250 nm, 100 to 1200 nm, 150 to 450 nm, 150 to 600 nm, 200 to 500 nm, 200 to 520, 200 to 600 nm, 300 to 600 nm, 300 to 700 nm, 300 to 800 nm, 400 to 600 nm, 400 to 700 nm, 800 nm, 500 to 750 nm, 750 to 1000 nm, 1000 to 1500 nm, and from 1500 to 2000 nm. Accordingly, the oltipraz crystals of this disclosure typically have an intensity averaged (Z-average) MHD of from 30 to 1200 nm, such as from 100 to 600 nm, e.g. from 150 to 450 nm, 400 to 700 nm, 400 to 600 nm or 450 to 550 nm, e.g., from about 300 to 400 nm such as around 350 to 390 nm or from 400 to 600 nm such as around 500 nm, as measured by Dynamic Light Scattering.

It also is noted that the MHD measurements discussed herein also may reflect the presence of any additional ingredients such as the stabilizing agent(s) to the extent that they are present in the composition with the crystals. As used herein, however, MHD measurements obtained for complete aqueous dispersions comprising crystals and one or more stabilizing agents, surfactants or other ingredients in the aqueous dispersion are deemed to be MHD measurements of the crystals themselves.

MHD can be determined by DLS using an appropriate instrument, e.g., a Malvern Zetasizer Nano-ZSP, using routine methods know to those skilled in the art. For example, the crystals can be put into an aqueous suspension with deionized water to a concentration of 0.01-0.1 mg (based on the weight of oltipraz) per mL prior to analysis. The result will be a transparent orange-red suspension. A backscatter (173°) detector can be used. The temperature should be set to 25° C. and samples equilibrated for 90 seconds prior to analysis. The duration, number of runs, attenuator setting, and focal position can be set automatically by the software. MHD values can be recorded with attenuator settings of 4-6 with mean count rates of 180-500 kcps.

All calculations of crystal size discussed herein can be performed in the Malvern Zetasizer software. As noted above, average crystal sizes discussed herein are intensity-averaged mean hydrodynamic radius (Z-average). The size is calculated from the mean decay time of the autocorrelation function and the Stokes-Einstein equation. The viscosity of water at 25° C. (0.8872 cP) was used. In cases where a crystal size distribution is given, the Malvern General Purpose (normal resolution) method is used, which uses non-negative least squares (NNLS) fitting of the decay curves. The functioning of the Malvern Zetasizer can be periodically checked using 100 nm polystyrene beads calibration standard. The relaxation time in the DLS experiment is between 600 and 1500 microseconds with the preferred relaxation time between 500 and 1300 microseconds.

The size calculation for the crystal sizes reported herein is based on a cumulant method using the equation: $\Gamma q2 = D = kBT/3\pi\eta d$ where D is the diffusion coefficient calculated from the measured decay rate (Γ), kBT/3πηd is the Stokes-Einstein equation, d is the particle diameter, and q is the scattering wave vector which is dependent on the specific instrument method parameters as listed above. The magnitude of the scattering wave vector is calculated according to the equation q=4 Pi (refractive index of solvent) Sin(theta/2)/wavelength. The expected delay time will change if a different instrument uses a different value of q. For calculations used herein, theta=173 deg, a refractive index of 1.333 for water is used, a laser wavelength of 633 nm yields a value for q=0.0264 nm^(−1).

As discussed above, the inherent variability of the wet milling process means that the size of individual crystals in any given quantity of crystals will vary and thus a quantity of crystals prepared according to this disclosure can be characterized by a distribution of crystals of varying sizes. One measure of the distribution of sizes is the polydispersity index (PdI) of the crystals in the quantity. The formula for determining PdI is:

$$PdI=(\sigma/d)^2$$

where σ is the standard deviation and d is the mean hydrodynamic diameter (Z-average) is less than 0.80, wherein PdI=(σ/d)², wherein σ is the standard deviation and d is the mean hydrodynamic diameter (Z-average). Lower values of PdI indicate a more uniform distribution of crystals in a given quantity of crystals. Typically, oltipraz crystals or quantities of such crystals in accordance with this disclosure have a PdI of less than 1, usually less than 0.8, often less than 0.6; for example between 0.10 and 0.60, e.g. between 0.10 and 0.45, such as between 0.1 and 0.35 e.g. 0.1 and 0.25. Certain embodiments of quantities of crystals in accordance with this disclosure can have a PdI of less than 1, less than 0.8, less than 0.6, e.g., between 0.10 and 0.60, and between 0.10 and 0.45, 0.1 and 0.35 and 0.1 and 0.25.

Typically, therefore, this disclosure provides oltipraz crystals having an intensity averaged (Z-average) MHD (as measured by Dynamic Light Scattering) of from 30 to 1200 nm wherein the PdI of the crystals is from 0.1 to 0.6. More typically this disclosure provides oltipraz crystals having an intensity averaged (Z-average) MHD of from about 100 to about 600 nm wherein the PdI of the crystals is from 0.1 to 0.45. Still more typically this disclosure provides oltipraz crystals having an intensity averaged (Z-average) MHD of from about 150 to about 450 nm, 400 to 700 nm, 400 to 600 nm, or 450 to 550 nm, wherein the PdI of the crystals is from 0.1 to 0.35.

Figure 2:
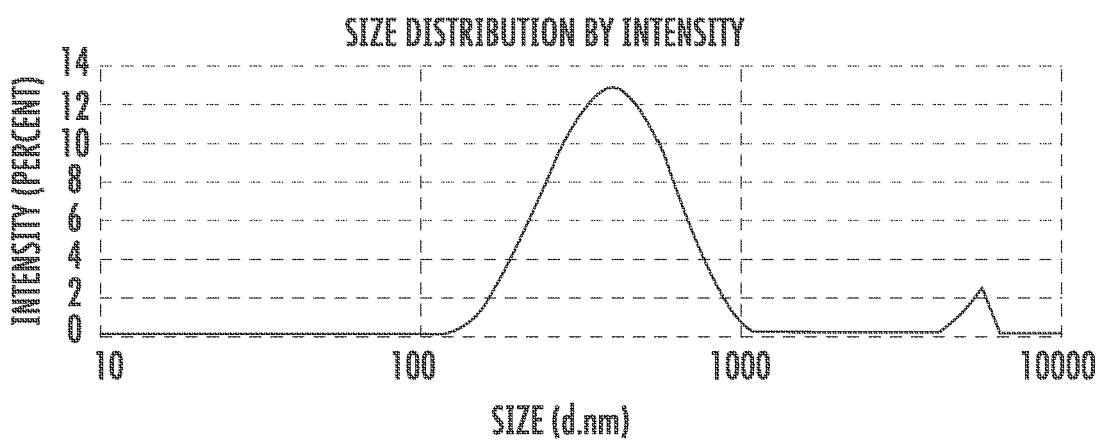
Figure 3A:
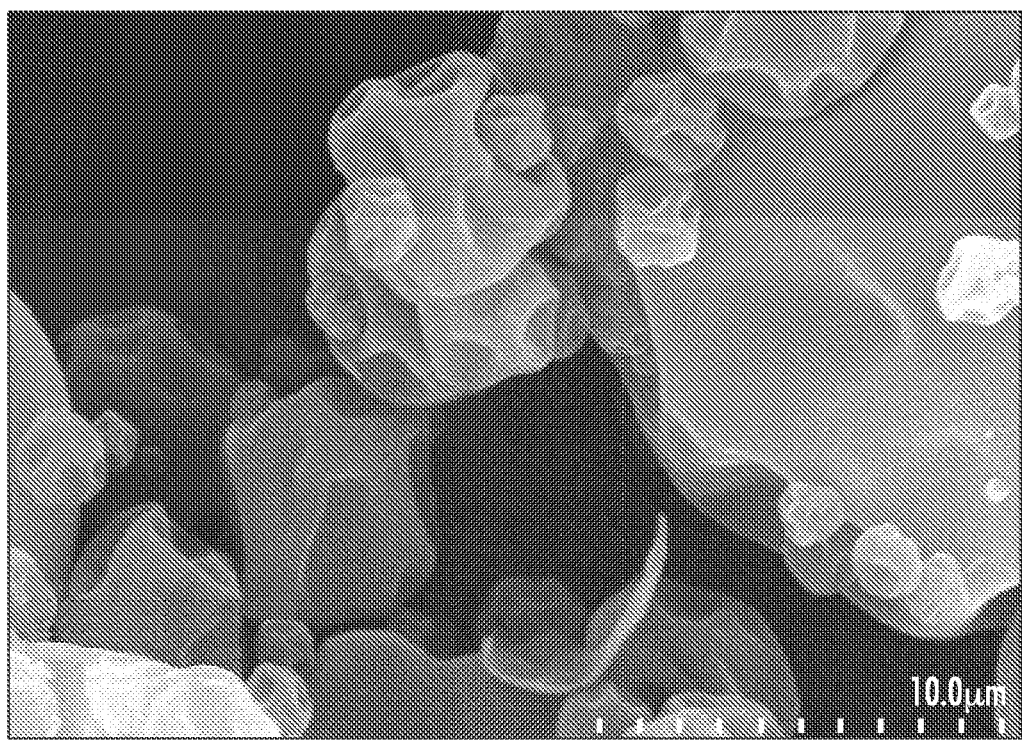
FIG. 3a is a scanning electron microscopy (SEM) image at 5000× magnification of a composition comprising oltipraz described in Example 2 prior to stability testing.
Figure 3B:
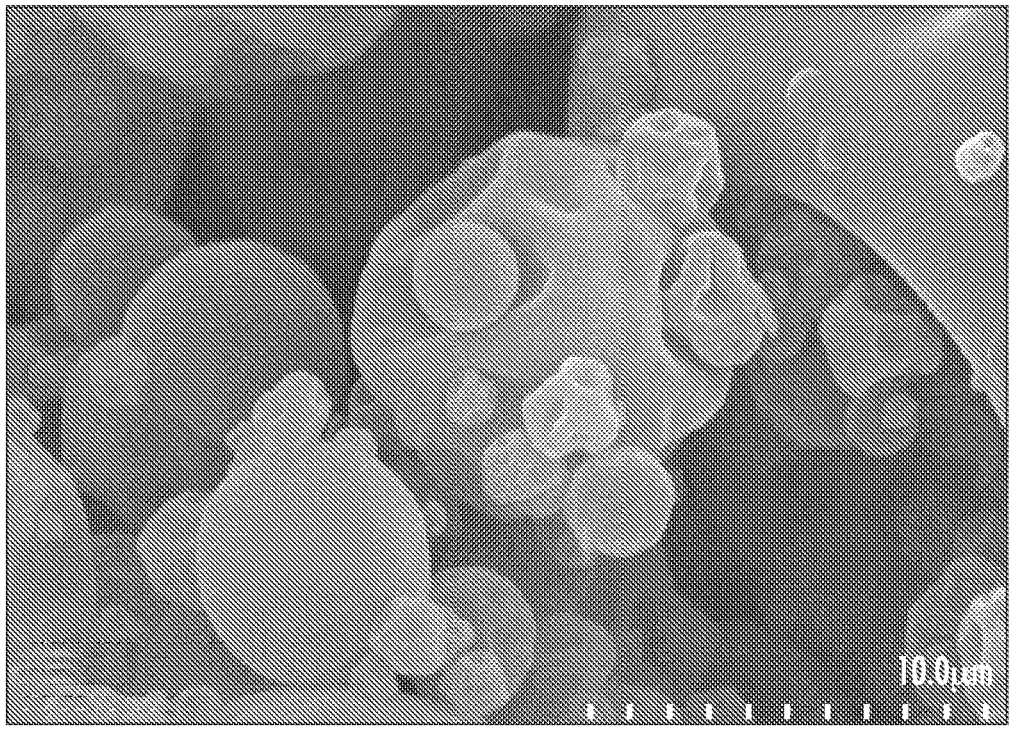
FIG. 3b is a SEM image at 5000× magnification of the dry composition described in Example 2 after stability testing for three months at 40° C. and 75% RH.
Figure 3C:
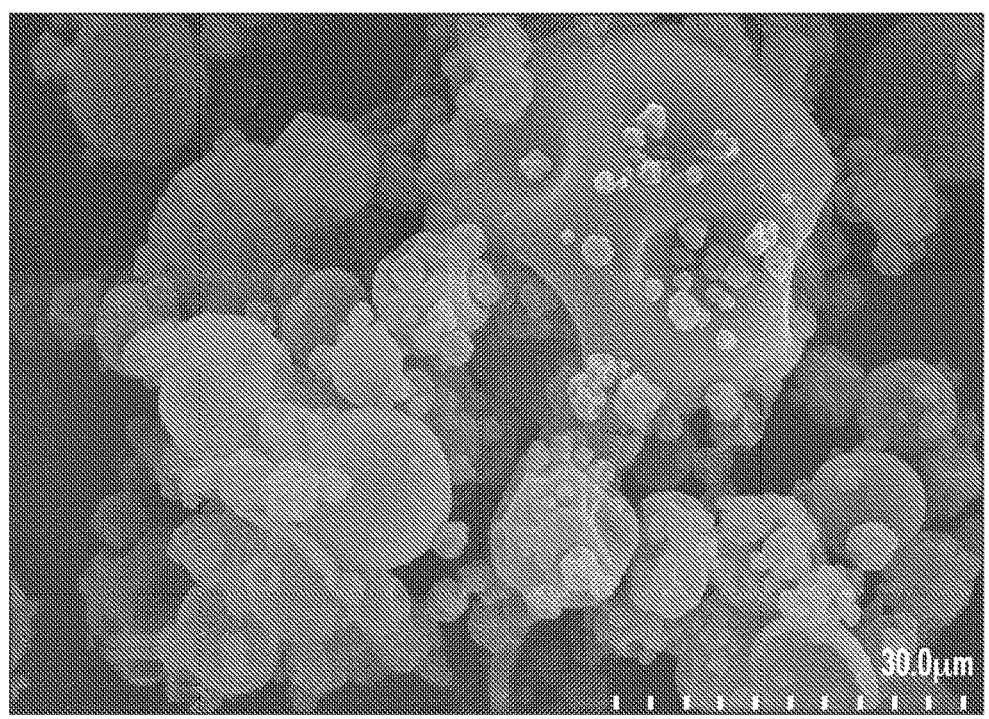
FIG. 3c is a SEM image at 1500× magnification of the dry composition described in Example 2 after stability testing for three months at 40° C. and 75% RH.

FIGS. 1 and 2 illustrate a correlogram and intensity size distribution for a DLS analysis of a sample of suspended crystals at 25° C. The relaxation time is 1180 microseconds, MHD is 403 nm, and the PdI is 0.364. It is noted that the x axis for both plots is logarithmic. The MHD and PdI are both calculated by the instrument based on the data obtained and are not determined visually from the figures.

C. Dry Compositions Comprising Crystals

As discussed above, the liquid compositions comprising crystals in suspension can be admixed with a bulking agent and then spray dried, lyophilized or otherwise processed to remove the water and/or other liquid solvent to form a dry composition. The resulting dry composition can comprise particles that largely comprise the bulking agent and thus can be much larger than the oltipraz crystals. For example, particles up to 200 microns (200,000 nm) or larger may be obtained. If desired, the size of the particles obtained from processes such as spray drying may be measured by scanning electron microscopy, laser diffraction or light microscopy. Dry compositions prepared according to this disclosure generally will be in the form of an orange-red powder, and can be prepared with no discolorations or large particles or chinks visible.

Bulking Agents

The presence of a bulking agent reduces the likelihood of crystal-crystal surface contact in a dry composition such as a spray-dried or lyophilized powder, as direct contact can make the crystals harder to re-suspend where the ultimate use of the composition is resuspension in a liquid composition. Bulking agents that are generally very soluble in water may be able to release the crystals as individual crystals upon resuspension. Accordingly, bulking agents that are very soluble in water are typically used in compositions of this disclosure. Those skilled in the art are capable of choosing appropriate bulking agents based on the particular composition and intended route of delivery. Furthermore, because the bulking agent can be such a large fraction of the overall dry composition product, its properties may affect the rate of resuspension in water as well as potentially influence the taste of the composition if administered orally, possibly significantly.

One factor that can be evaluated to determine if a particular bulking agent is appropriate for a particular embodiment includes whether the bulking agent does not alter the initial size of the crystals in suspension prior to removal of water, e.g., through spray dying or lyophilization. Where the intended use of the dry composition is resuspension with water or other liquid to make a liquid composition for oral or other form of administration, then advantageously, a bulking agent is typically chosen that (i) does not yield large particles of precipitate upon resuspension with water, (ii) does not yield a dry powder that dissolves too slowly upon mixing with water, and (iii) yields a dry powder that is relatively stable to handling and storage, e.g., is not hygroscopic such that handling of the dry composition becomes difficult. Surface active agents may be added to the formulation, either in the liquid composition or to the dry composition in order to enhance such properties in the dry composition. Such properties may be less important, however, if the dry composition is to be formulated into a pill, tablet, capsule, gel capsule or the like for oral administration. Where the intended use of the dry composition is oral administration such as in a pill, tablet or capsule, then the bulking agent also should be evaluated on its ability to provide the desired pharmacological profile following administration. If the smaller crystalline drug particles coated with a stabilizing agent are adsorbed onto the larger particles of the bulking agent during blending or granulation, such as roller compaction, fluid bed, or high shear, then a water soluble bulking agent such as mannitol, or insoluble agent such as microcrystalline cellulose, may act as a carrier for those particles and aid the rate of dissolution from a capsule or a tablet.

As noted above, in principle, a bulking agent also can act as a stabilizing agent. Examples of bulking agents include, but are by no means limited to, the group consisting of polyvinylpyrrolidones (e.g., PVP K30 and PVP-VA64), cellulosic polymers such as HPC, HPMC. HPMC E3. Trehalose, and Dextrans such as Dextran 10 or Dextran 40. Examples of bulking agents such as PVP-VA64 and HPC EF that provide acceptable results for certain embodiments of this disclosure are provided herein. Most typically the bulking agent is PVP-VA64. Sometimes it is preferable that the bulking agent is not Dextran 40. As noted above, appropriate bulking agents or combinations of bulking agents can be determined for a particular composition and route of delivery. Factors such as the intended route of administration of the crystals (e.g., whether the crystals are to be administered in a dry form such as a pill or capsule or resuspended with a liquid such as water), all may be considered in determining one or more acceptable bulking agents for a particular embodiment. Other factors such as the size and amounts of crystals, type and quantity of stabilizing agent used (if any), the surfactants and amounts thereof (if any) that are employed, the amount of bulking agent to be used, the total solids in the liquid composition, the liquids in the composition and any resuspension, and the process for removing water (and/or other liquid), also may be taken into account in determining acceptable bulking agents or combinations of bulking agents.

In some circumstances use of Dextran 10 may provide a dry composition that provides particle sizes that are too large upon resuspension in water. In other embodiments, HPMC may provide a composition that dissolves more slowly than desired upon resuspension with water. In some embodiments, Trehalose can provide a composition that is more hygroscopic than desired for routine handling. Special packaging or the addition of desiccant may be used to maintain the low water content of such hygroscopic pharmaceutical compositions during stability on the shelf. Accordingly, it is sometimes preferable that the bulking agent is not dextran 10 and/or is not HPMC and/or is not trehalose. In different embodiments however, e.g., with different stabilizing agents, surfactants, or for a different intended route of administration, such bulking agents can provide acceptable compositions.

Within the aqueous or liquid composition, depending on the amount of liquid used, the bulking agent(s) can comprise from about 1 to 40% by weight or more of the composition. Within such ranges are, e.g., 1 to 5%, 5 to 10%, 10 to 15%, 10 to 20%, 15 to 20%, 15 to 25%, 20 to 25%, 20 to 30%, 25 to 30%, 25 to 35%, 30 to 35%, 30 to 40%. Depending on the method chosen for removing water, the total solids in the composition may have to be maintained below a certain level to facilitate processing to a dry composition, e.g., in certain embodiments, below 30%, or about 28%, and thus the amount of bulking agent(s) used may be limited by such considerations. In certain embodiments, therefore, the bulking agent can comprise between 15% and 25%, e.g., about 20 or 21%. Accordingly, the bulking agent(s) typically comprise from about 1 to about 40 wt % of the liquid composition, such as from about 10 to about 30 wt % e.g. from about 15 to about 25 wt % such as from about 20 to about 21 wt %.

Alternatively, as with the other ingredients, the amount of bulking agent can be calculated as a percent of the solids, i.e., the non-solvent components. As a percent of the solids, the bulking agent(s) can be present in amounts by weight ranging from less than 40% up to 98% or more, e.g., 40 to 50%, 50 to 60%, 55 to 65%, 60 to 70%, 60 to 75%, 60 to 80%, 65 to 75%, 65 to 80%, 70 to 80%, 75 to 85%, 75 to 90%, 80 to 90%, 80 to 95%, 85 to 95%, 90 to 98%, and greater than 98% by weight. In certain embodiments, the bulking agent(s) can comprise between 65 and 80% by weight of the total solids, e.g., between about 70 and 78%. e.g., about 74% by weight of the total solids. Accordingly, the bulking agent(s) typically comprise from about 40 to about 90 wt % of the non-solvent (ie solid) composition, such as from about 65 to about 80 wt % e.g. from about 70 about 78 wt % such as from about 73 to about 75 wt %. Such amounts will also correspond to the amounts of the bulking agent(s) in the dry composition.

The disclosure therefore provides crystals of oltipraz having a MHD of from about 30 to about 2000 nm as measured by dynamic light scattering, wherein the crystals typically have a solubility in water at 20° C. of from about 3.5 to about 8 µg/ml. More typically this disclosure provides crystals of oltipraz having a MHD of from about 100 to about 800 nm as measured by dynamic light scattering, wherein the crystals typically have a solubility in water at 20° C. of from about 4.5 to about 7 µg/ml. Still more typically this disclosure provides crystals of oltipraz having a MHD of from 150 to about 450 nm, 400 to 700 nm, 400 to 600 nm, or 450 to 550 nm, as measured by dynamic light scattering, wherein the crystals typically have a solubility in water at 20° C. of from about 5 to about 6.5 µg/ml The disclosure also provides a liquid composition comprising oltipraz crystals according to this disclosure, wherein the composition does not comprise a bulking agent, and wherein:
  the composition comprises between about 1 to about 40 wt % of oltipraz crystals, based on the weight of the liquid composition;
  the non-solvent components in the composition typically comprise from about 1 to about 70 wt % oltipraz crystals; and
  the composition comprises (i) from about 5 to about 40 wt % (based on the weight of solid components in the composition) of one or more of acrylate- and alkenyl ether-based co-polymers, polyvinylpyrrolidone, hydroxypropylcellulose, hydroxypropyl methylcellulose, a copovidone such as PVP-VA64, and a polymethacrylate-based copolymer such as EUDRAGIT® RL; and/or (ii) from about 10 to about 20 wt % % (based on the weight of solid components in the composition) of one or more of sodium lauryl sulfate, a poloxamer such as Pluronic F-68 and polysorbate 80.

This disclosure also provides a liquid composition comprising oltipraz crystals according to this disclosure, wherein the composition does not comprise a bulking agent, and wherein
  the composition comprises between about 4 to about 15 wt % of oltipraz crystals, based on the weight of the liquid composition;
  the non-solvent components in the composition typically comprise from about 50 to about 60 wt % oltipraz crystals;
  the composition comprises (i) from about 20 to about 35 wt % (based on the weight of solid components in the composition) of one or more of a polymethacrylate-based copolymer such as Eudragit RL, an acrylate- and alkenyl ether-based co-polymer such as Carbopol 974P NF; a polyvinylpyrrolidone such as PVP (K15 or K-30); a hydroxypropylcellulose such as HPC EF and a hydroxypropyl methylcellulose such as HPMC E3; and/or (ii) from about 12 to about 18 wt % % (based on the weight of solid components in the composition) of one or more of sodium lauryl sulfate, a poloxamer such as Pluronic F-68 and polysorbate 80;
  the liquid solvent is water or an aqueous buffer solution; and
  the composition optionally comprises from 0.1 to 1 wt % of poly(dimethylsiloxane) or silicon dioxide (simethicone) based on the non-solvent components in the composition.

This disclosure also provides a liquid composition comprising oltipraz crystals according to this disclosure, wherein the composition does not comprise a bulking agent, and wherein the composition comprises between about 7 to about 10 wt % of oltipraz crystals, based on the weight of the liquid composition;

the non-solvent components in the composition typically comprise from about 55 to about 58 wt % oltipraz crystals;

the composition comprises (i) from about 25 to about 30 wt % (based on the weight of solid components in the composition) of one or more of a copovidone such as PVP-VA64 and a polymethacrylate-based copolymer such as EUDRAGIT® RL; and/or (ii) from about 14 to about 15 wt % % (based on the weight of solid components in the composition) of polysorbate 80 (Tween 80);

the liquid solvent is water, and the composition optionally comprises 0.1 to 1 wt % simethicone based on the non-solvent components in the composition.

The liquid composition comprising oltipraz crystals but not comprising a bulking agent is typically suitable for milling.

The disclosure also provides a liquid composition comprising oltipraz crystals according to this disclosure and a bulking agent, wherein The concentration of oltipraz crystals in the liquid is from about 0.1 to about 10 wt % based on the weight of the liquid composition;

the non-solvent components in the composition typically comprise from about 0.5 to about 25 wt % oltipraz crystals;

the composition comprises (i) from about 5 to about 40 wt % (based on the weight of solid components excluding bulking agents in the composition) of one or more of acrylate- and alkenyl ether-based co-polymers, polyvinylpyrrolidone, hydroxypropylcellulose, hydroxypropyl methylcellulose, a copovidone such as PVP-VA64, and a polymethacrylate-based copolymer such as EUDRAGIT® RL; and/or (ii) from about 10 to about 20 wt % % (based on the weight of solid components excluding bulking agents in the composition) of one or more of sodium lauryl sulfate, a poloxamer such as Pluronic F-68 and polysorbate 80; and the composition comprises from about 1 to about 40 wt % (based on the overall weight of the composition) of a bulking agent selected from polyvinylpyrrolidones (e.g., PVP K30 and PVP-VA64), cellulosic polymers such as HPC. HPMC. HPMC E3, Trehalose, Dextrans (such as Dextran 10 or Dextran 40), PVP-VA64 and HPC EF.

This disclosure also provides a liquid composition comprising oltipraz crystals according to this disclosure and a bulking agent, wherein The concentration of oltipraz crystals in the liquid is from about 1 to about 6 wt % based on the weight of the liquid composition;

the non-solvent components in the composition typically comprise from about 5 to about 20 wt % oltipraz crystals;

the composition comprises (i) from about 20 to about 35 wt % (based on the weight of solid components excluding bulking agents in the composition) of one or more of a polymethacrylate-based copolymer such as Eudragit RL, an acrylate- and alkenyl ether-based co-polymer such as Carbopol 974P NF; a polyvinylpyrrolidone such as PVP (K15 or K-30); a hydroxypropylcellulose such as HPC EF and a hydroxypropyl methylcellulose such as HPMC E3; and/or (ii) from about 12 to about 18 wt % % (based on the weight of solid components excluding bulking agents in the composition) of one or more of sodium lauryl sulfate, a poloxamer such as Pluronic F-68 and polysorbate 80;

the composition comprises from about 10 to about 30 wt % (based on the overall weight of the composition) of a bulking agent selected from PVP-VA64 and HPC EF;

the liquid solvent is water or an aqueous buffer solution; and the composition optionally comprises from 0.1 to 1 wt % of poly(dimethylsiloxane) or silicon dioxide (simethicone) based on the non-solvent components (excluding the bulking agent) in the composition.

This disclosure also provides a liquid composition comprising oltipraz crystals according to this disclosure and a bulking agent, wherein The concentration of oltipraz crystals in the liquid is from about 2 to about 5 wt % based on the weight of the liquid composition;

the non-solvent components in the composition typically comprise from about 10 to about 18 wt % oltipraz crystals;

the composition comprises (i) from about 25 to about 30 wt % (based on the weight of solid components excluding bulking agents in the composition) of one or more of a copovidone such as PVP-VA64 and a polymethacrylate-based copolymer such as EUDRAGIT® RL; and/or (ii) from about 14 to about 15 wt % % (based on the weight of solid components excluding bulking agents in the composition) of polysorbate 80 (Tween 80);

the composition comprises from about 15 to about 25 wt % (based on the overall weight of the composition) of a bulking agent which is PVP-VA64;

the liquid solvent is water; and the composition optionally comprises 0.1 to 1 wt % simethicone based on the non-solvent components (excluding the bulking agent) in the composition.

The liquid composition comprising oltipraz crystals according to this disclosure and a bulking agent is typically suitable for drying e.g. spray-drying.

The disclosure also provides a dry composition comprising oltipraz crystals according to this disclosure and a bulking agent, wherein:

The percentage of oltipraz in the composition (i.e. the drug loading) is from about 12 to about 20 wt %;

the composition comprises (i) from about 5 to about 40 wt % (based on the weight of solid components excluding bulking agents in the composition) of one or more of acrylate- and alkenyl ether-based co-polymers, polyvinylpyrrolidone, hydroxypropylcellulose, hydroxypropyl methylcellulose, a copovidone such as PVP-VA64, and a polymethacrylate-based copolymer such as EUDRAGIT® RL; and/or (ii) from about 10 to about 20 wt % % (based on the weight of solid components excluding bulking agents in the composition) of one or more of sodium lauryl sulfate, a poloxamer such as Pluronic F-68 and polysorbate 80; and the composition comprises from about 40 to about 90 wt % (based on the overall weight of the composition) of a bulking agent selected from polyvinylpyrrolidones (e.g., PVP K30 and PVP-VA64), cellulosic polymers such as HPC, HPMC, HPMC E3, Trehalose, Dextrans (such as Dextran 10 or Dextran 40), PVP-VA64 and HPC EF.

This disclosure also provides a dry composition comprising oltipraz crystals according to this disclosure and a bulking agent, wherein:

The percentage of oltipraz in the composition (i.e. the drug loading) is from about 14 to about 18 wt %;

the composition comprises (i) from about 20 to about 35 wt % (based on the weight of solid components excluding bulking agents in the composition) of one or more of a polymethacrylate-based copolymer such as Eudragit RL, an acrylate- and alkenyl ether-based co-polymer such as Carbopol 974P NF; a polyvinylpyrrolidone such as PVP (K15 or K-30); a hydroxypropylcellulose such as HPC EF and a hydroxypropyl methylcellulose such as HPMC E3; and/or (ii) from about 12 to about 18 wt % % (based on the weight of solid components excluding bulking agents in the composition) of one or more of sodium lauryl sulfate, a poloxamer such as Pluronic F-68 and polysorbate 80;

the composition comprises from about 65 to about 80 wt % (based on the overall weight of the composition) of a bulking agent selected from PVP-VA64 and HPC EF; and the composition optionally comprises from 0.1 to 1 wt % of poly(dimethylsiloxane) or silicon dioxide (simethicone) based on the weight of solid components excluding bulking agents in the composition This disclosure provides a dry composition comprising oltipraz crystals according to this disclosure and a bulking agent, wherein:

The percentage of oltipraz in the composition (i.e. the drug loading) is from about 15 to about 17 wt %;

the composition comprises (i) from about 25 to about 30 wt % (based on the weight of solid components excluding bulking agents in the composition) of one or more of a copovidone such as PVP-VA64 and a polymethacrylate-based copolymer such as EUDRAGIT® RL; and/or (ii) from about 14 to about 15 wt % % (based on the weight of solid components excluding bulking agents in the composition) of polysorbate 80 (Tween 80); and the composition comprises from about 70 to about 78 wt % (based on the overall weight of the composition) of a bulking agent which is PVP-VA64; and the composition optionally comprises 0.1 to 1 wt % simethicone based on the weight of solid components excluding bulking agents in the composition The dry composition described above can be suspended in liquid to form a liquid suspension; typically the weight ratio of the solid:liquid is from about 1:10 to 1:200 such as from about 1:20 to 1:150 e.g. 1:30 to 1:100. Typically one or more taste-enhancing or taste-masking agent may also be included in the suspension; for example one or more taste-enhancing agents selected from a natural mint or menthol flavor; a fruit flavor such as a sweet berry flavor, a sweetener, and a cooling/freshening agent such as a Physcool® flavor described herein may be included, optionally together with a component such as a preservative.

The oltipraz crystals in the liquid compositions described above typically retain a MHD of from 30 to 1200 nm for at least 1 hour; more typically the oltipraz crystals retain a MHD of from 100 to 800 nm for at least 6 hours; still more typically the oltipraz crystals retain a MHD of from 150 to 450 nm, 400 to 700 nm, 400 to 600 nm, or 450 to 550 nm for at least 24 hours.

The oltipraz crystals in the solid compositions described above typically have a solubility in water at 20° C. of from about 3.5 to about 8 μg/ml, more typically from about 4.5 to about 7 μg/ml, still more typically from about 5 to about 6.5 μg/ml.

D. Methods of Making Compositions Comprising Crystals

Methods of making compositions described herein typically provide advantages due to their scalability. The methods described herein can be used for large, commercial-scale production (e.g., kilogram quantities), of compositions comprising the oltipraz crystals. Moreover, certain embodiments of the methods described herein can provide compositions comprising crystals of oltipraz with a bulking agent made from aqueous composition using water-removal methods such as spray-drying or lyophilization. Hence, such embodiments do not generate a large amount of organic solvent waste.

Wet Milling

Oltipraz may be synthesized or may be obtained from commercial vendors, e.g. Sigma-Aldrich® and Santa Cruz Biotechnology®, Inc. Methods for synthesizing oltipraz (4-Methyl-5-(2-pyrazinyl)-1,2-dithiole-3-thione) have been described in the art. (See e.g. U.S. Pat. No. 4,110,450).

Wet milling of the oltipraz can be carried out by known processes. For example, the oltipraz can first be suspended in water to form an aqueous composition. A different liquid may be used in addition to, or in place of water. The oltipraz suspension can be milled in a temperature controlled grinding chamber (such as a Dyno-mill, model KDL) using a grinding media such as 0.5 mm yttrium-stabilized zirconium oxide spheres. The total grinding time is chosen so as to provide a target MHD as measured by DLS, as described above. The time for grinding varies with the type of mill, and whether it is recirculating. While a Dyno-mill may be suitable for smaller batches, other larger mills, such as Netzsch mills, can adapt the process to much larger scales of batches of crystals with the same target MHD. As discussed above, one or more stabilizing agents and/or surfactants may be added to the wet-milling composition. Where at least one stabilizing agent is provided, the crystals may be stable in the liquid composition for a period of time. That is, the MHD of the crystals can remain within a target range for a period of time, e.g., at least 1 hour, 6 hours, 12 hours, 24 hours, 48 hours and 72 hours. The weight percent of oltipraz in the liquid milling composition can vary from 1% up to 20% percent or more (excluding the weight of the milling media). Within such range are the following sub-ranges, i.e., 1 to 5%, 5 to 10%, 5 to 15%, 10 to 15%, 10 to 20%, and more than 20%. In certain embodiments, prior to the addition of bulking agent, the loading of oltipraz during milling is between about 5 and 10% by weight of the aqueous composition, or about 8.6%. In other embodiments, prior to the addition of bulking agent the loading of oltipraz and other non-aqueous components such as the stabilizing agent(s) during milling may be between 13 and 17%, e.g., about 15%, which represents a high loading of solids for wet milling.

During milling, the temperature can be less than 40° C., but above 2° C. to avoid the composition approaching the freezing point. Generally speaking, however, colder is better to minimize both chemical degradation (to avoid drug-degradent impurities) and to lower the solubility of the compound so the milled crystals do not grow due to a dissolution/recrystallization mechanism. Using such conditions can minimize drug-degradent impurities relative to 4-methyl-5-(pyrazin-2-yl)-3H-1,2-dithiole-3-thione in the aqueous composition to less than 1%, e.g. less than 0.5%, e.g. less than 0.1%, and minimize the drug-degradent impurities to less than 2% such as less than 1% or less than 0.5% relative to the 4-methyl-5-(pyrazin-2-yl)-3H-1,2-dithiole-3-thione in the aqueous suspension. Typically, such conditions can minimize drug-degradent impurities relative to 4-methyl-5-(pyrazin-2-yl)-3H-1,2-dithiole-3-thione in the aqueous composition to less than 1%, less than 0.5%, or less than 0.1%, and minimize the drug-degradent impurities to less than 2%, less than 1% or less than 0.5% relative to the 4-methyl-5-(pyrazin-2-yl)-3H-1,2-dithiole-3-thione in the aqueous suspension. In certain embodiments, the temperature may be maintained at about 10° C. The liquid compositions prepared from milling may be used to prepare additional compositions. e.g., pharmaceutical compositions. Alternatively, where a dry composition of the crystals is desired, the liquid compositions may be subjected to further processing as discussed below to effect removal of the water and/or other solvent liquid.

Other Crystal-Formation Processes

As noted above, oltipraz crystals may be made by methods other than milling. For example, crystals of oltipraz may be prepared by antisolvent precipitation, supercritical fluid precipitation or other known means of producing compositions comprising particles having an MHD in the size ranges described herein. Stabilizing agents may be added as in the wet milling process and removal of liquids may still be necessary.

Liquid Removal

Once the target MHD of the oltipraz crystals is reached, all or a portion of the suspension then may be mixed with one or more bulking agents as described above. The resulting mixture may be further diluted as desired to achieve the desired target solids content prior to further processing to remove the water and/or other liquid from the composition. The final suspension may be stirred prior to the step of removing the liquid.

Where the liquid of the composition is water, known processes such as spray drying or lyophilization may be used to remove the water from the composition. An exemplary spray-drying process is provided below in Example 1. The resulting composition then may be further processed as desired. The powder is preferably stable for a period of time, e.g., at least one month, at least two months, at least three months, or at least six months, one year, two years, or more than two years. Stability of the powder may be measured at room temperature (e.g., 70° F. or 21° C.) or at a temperature below room temperature (e.g., 5° C.) or at a higher temperature and relative humidity, e.g., 40° C., and 75% RH. Stability of the powder may be measured according to a number of means, including purity, potency, or ability to re-suspend and remain substantially re-suspended in a liquid composition (see Example 4).

When milling and spray drying are employed in combination, the following parameters may need to be considered and adjusted to achieve acceptable or optimal results.

Throughput:

This can be an important process consideration as it can dictate how high the solids loading will be during the wet milling step and liquid removal. That is, the higher the desired throughput, the higher the solids loading required during milling and spray-drying. A high solids loading in the milling step is about 15%, although higher amounts such as about 20% may be achieved. Further, one can mill at a high solids loading (e.g., 15 wt %) and not dilute the aqueous composition with water (i.e., avoid a washing step to recover more product) at any point. Then this high solids-loaded composition can be fed into spray drying and sprayed at a high solids loading, e.g., about 28% solids. The desire to push throughput can be dictated by the fact that the spraying is done out of water where the high dew point of water relative to organic solvents at similar vapor composition limits the rate at which one can spray dry.

Nozzle and drying Gas Flow Rate:

In certain embodiments, spray drying such solutions at high throughput can be facilitated by using a two-fluid nozzle for atomization and adjusting the atomization gas flow rate to get the desired particle size distribution. By maintaining a sufficient drying gas flow rate, the process can be relatively insensitive to fluctuations in solution/suspension flow rate. If the atomization gas rate is too low, however, then particle size can become very sensitive to suspension flow fluctuations. Running in the more robust regime can be important because the highly viscous spray suspension can be difficult to run at the necessary flow rate without significant fluctuations.

Time:

Total residence time of the oltipraz crystals in the grinding environment is a parameter for milling. For a given set of milling conditions, e.g., oltipraz loading, the wet-milling machinery and milling media used, milling temperature, and target particle size are among the parameters that will dictate the total residence time for milling. Compositions of crystals having smaller MHD values typically will require longer milling times, and one of ordinary skill will be able to determine the milling time necessary for a desired MHD through routine experimentation.

Milling Machinery and Parameters:

For a given target crystal size, one of ordinary skill can find a combination of wet-milling machinery and wet-milling media that can achieve the target crystal size. For example, a target range of MHD between 150 and 600 nm, e.g., 150 to 450 nm, can be achieved with either DynoMill or LabRAM milling machinery. For such MHD ranges, a combination of a rotor speed for the DynoMill of about 3000 rpm and 0.5 mm grinding spheres can be used. For LabRAM, acceleration of 50 g and using a combination of 0.2 mm and 0.6 mm grinding spheres can provide acceptable results. The two systems will require different times however.

As noted above, in other embodiments, the crystals may be made by precipitation, antisolvent precipitation, super critical liquid precipitation, fluid bed granulation, wet-impregnation, evaporation (e.g., rotary evaporation, vacuum drying) and other methods known to persons of ordinary skill in the art.

E. Pharmaceutical Compositions

Dry Compositions

The crystals described herein may be used to formulate various kinds of pharmaceutical preparations. The preparations typically comprise a dry composition as described above. Practically speaking, pharmaceutical compositions comprising the dry composition can comprise any amount of the oltipraz crystals. The amount of the composition will depend on the desired dosage of the oltipraz and the concentration of the oltipraz in the dry composition. In certain embodiments, for example, the dry composition comprises a single dose of up to 5000 mg, e.g., 100 to 500 mg, 500 to 1000 mg, 1000 to 1500 mg, and 1500 to 2000 mg, 2000 to 2500 mg, 2500 mg to 3000 mg, 3000 mg to 4000 mg and 4000 mg to 5000 mg. The dose may thus be from 100 to 5000 mg such as from 500 to 4000 mg, such as from 1000 to 3000 mg e.g. from 1500 to 2000 mg. Single dosage amounts over 5000 mg also may be employed. Within such ranges are exemplary amounts of up to 600 mg of a dry composition as described above, up to 500 mg of a dry pharmaceutical composition, up to 400 mg of a dry pharmaceutical composition, up to 350 mg of a dry composition, or up to 300 mg of a dry composition as described herein. Exemplary amounts within such ranges also include 250 mg, 300 mg, 350, mg, 400 mg, 450 mg, 500 mg, 550 mg, 600 mg, 650 mg, 700 mg, 750 mg, 800 mg, 850 mg, 900 mg, 950 mg and 1000 mg, 1100 mg, 1200 mg, 1300 mg, 1400 mg, 1500 mg, 1600 mg, 1700 mg, 1800 mg, 1900 mg and 2000 mg. As described above, such dry pharmaceutical compositions can comprise from 5% to over 25% of oltipraz crystals. For example, if the dry composition comprises 5% oltipraz crystals, then the foregoing dosages comprise up to 250 mg of oltipraz. If the dry composition comprises 15% oltipraz crystals, then the foregoing dosages comprise up to 750 mg of oltipraz, and if the dry composition comprises 25% oltipraz crystals, then the foregoing dosages comprise up to 1250 mg of oltipraz.

Dry pharmaceutical compositions also may tend to be fairly electrostatic and so including a small amount of one or more pharmaceutically acceptable lubricants, e.g., magnesium stearate or silica oxide, can assist in the process of metering out quantities of the dry composition. Other processing techniques such as granulation, for example, roller compaction, high shear or fluid bed, may also be used to produce larger particles with binders or other pharmaceutical excipients that are more easily processed and still have rapid dissolution and greater solubility.

Liquid Compositions

In certain embodiments, the dry composition may be re-suspended in water and/or other liquid for oral administration as a liquid composition in a weight:weight ratio, of 1 part of dry composition and an amount of water of from less than 10 parts of water (or other liquid) up to 200 parts or more of water (or other liquid). Within such ranges include, e.g., 1-10, 10-20, 20-30, 30-40, 40-50, 50-60, 60-7, 70-80, 80-90, 90-100, 100-125, 125-150, 150-175, 175-200, or more than 200 parts of water (or other liquid) per part of dry composition. The ratio of dry composition to liquid can therefore be from 1:10 to 1:200 such as from 1:20 to 1:150 e.g. 1:30 to 1:100 such as 1:40 to 1:70 e.g. about 1:50 to 1:60. As noted above, where the composition is prepared using at least one stabilizing agent, the MHD of the crystals in the composition may remain within the target range for a period of time, e.g., at least 1 hour, at least 3 hours, at least 6 hours, at least 12 hours or at least 24 hours, or longer. Further, depending on the combinations of stabilizing agent (s), if any, and bulking agent (if any) and crystal size, the re-suspended composition also may readily dissolve, e.g., with vigorous shaking for less than 15 minutes, less than 10 minutes, less than 5 minutes, less than three minutes, less than 2 minutes less than one minute, or less than 30 seconds, and also may remain substantially homogeneously suspended for a period of time, e.g., for at least 1 hour, at least 3 hours, at least 6 hours, at least 12 hours, or at least 24 hours. A suspension of oltipraz crystals may be deemed to be substantially homogeneous if the concentration of oltipraz in a test sample taken from the top of the liquid composition after a defined period of time (e.g., less than 1 minute, 1 minute, 2 minutes, 5 minutes, 10 minutes, or 15 minutes) comprises a desired minimum target percentage of the original concentration, e.g., at least 85%, 90%, 95% or 98% of the concentration of oltipraz in a sample taken from the liquid composition immediately after the composition is resuspended to form a substantially homogeneous composition.

Formulations of the pharmaceutical compositions for oral administration also may be presented as a mouthwash, or a carbonated liquid, or an oral spray or aerosol, or an oral ointment, gel, or cream.

In certain embodiments, liquids suitable for formulating oltipraz compositions for oral administration, e.g., buccal administration, may include water; saline; buffer solutions (e.g., Krebs-Ringer Bicarbonate (KRB), citrate buffers, bicarbonate buffers, or phosphate buffers); organic solvents such as alcohols (specifically, ethanol) glycols (such as propylene glycol, poly(ethylene glycol), butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, dimethiconol, dimethicone, and dimethicone copolyol; hydrocarbon-based materials such as petrolatum and squalane: polysaccharide-based materials such as cellulose, methylcellulose, and functionalized cellulose derivatives such as hydroxypropyl methylcellulose, and other vehicles and vehicle components that are suitable for administration to the oral cavity, as well as mixtures of buccal vehicle components as identified above or otherwise known to the art.

In other embodiments, the oral formulations may be emulsions or suspensions. For example, the formulation may be comprised of METHOCEL™ and a buffer solution. METHOCEL™ refers to polymers of methylcellulose or hydroxypropylmethyl cellulose. METHOCEL™ polymers vary in their degree of methoxy- and/or hydroxypropyl-substitution on the cellulose polymeric backbone. The formulations may alternatively comprise cellulose polymers such as methylcellulose, ethylcellulose, ethylmethyl cellulose, hydroxyethyl cellulose, hydroxypropyl cellulose, hydroxyethyl methylcellulose, hydroxypropyl methylcellulose, ethylhydroxyethyl cellulose, or carboxymethylcellulose. The METHOCEL™ may be present in buffer in an amount from about 0.02 wt % to about 2 wt %. For example, the METHOCEL™ may be present in the buffer in an amount from about 0.1 wt % to about 0.5 wt %. METHOCEL™ can be about 0.25 wt % in buffer. The METHOCEL™ can be characterized by its degree of (e.g., percentage of monomeric units having) methoxy and/or hydroxypropyl substitution. The formulation can also include viscosity modifiers such as a Poloxamer and alginate. Exemplary buffer solutions useful in oral formulations (e.g., buccal formulations) include Krebs-Ringer Bicarbonate (KRB) buffer, citrate buffers, bicarbonate buffers, or phosphate buffers. In other embodiments, the liquid may be water or saline. Typically, the concentration of the crystals in the liquid is from about 0.004% to about 0.4%, such as from about 0.010% to about 0.040%, e.g. about 0.012% by weight of the liquid formulation. In certain embodiments, the concentration of the crystals in the liquid is about 0.004% to about 0.4%, 0.010% to about 0.040%, or 0.012% by weight of the liquid formulation. The concentration may also be represented by the percentage by weight of the crystals in the liquid formulation. Typically, the crystals are present in an amount of from about 0.026% to about 2.6%, e.g. from about 0.04% to about 0.4%, such as about 0.078% by weight of the formulation. In certain such embodiments, the crystals are present in about 0.026% to about 2.6%, 0.04% to about 0.4%, or about 0.078% by weight of the formulation. Other polymeric thickeners such as PVP or PVP/VA 64 may also be used.

Liquid dosage forms useful for oral administration include pharmaceutically acceptable emulsions, microemulsions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required crystal size in the case of dispersions, and by the use of surfactants.

Compositions for oral administration may include additional components, such as coloring agents, flavoring agents, fragrances, antimicrobial agents, or sweetening agents as further described.

Alternative embodiments of pharmaceutical compositions suitable for oral administration include compositions in the form of capsules (including sprinkle capsules and gelatin capsules), sachets, stickpacks, pills, tablets, lozenges (using a flavored basis, usually sucrose and acacia or tragacanth), lyophile, powders, granules, implantable compositions, or as a solution or a suspension in an aqueous or non-aqueous liquid, including, e.g., compositions suitable for injection or infusion, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a composition comprising a quantity of crystals as described herein as the active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), a composition comprising a quantity of the oltipraz crystals, e.g., a dry composition as described above, can be mixed with one or more pharmaceutically acceptable carriers, such as sodium citrate or dicalcium phosphate, and/or any of the following: (1) fillers or extenders, such as starches, microcrystalline cellulose, maltodextrins, lactose, sucrose, glucose, mannitol, and/or silicic acid: (2) binders, such as, for example, hydroxypropyl cellulose, hydroxypropylmethyl cellulose, carboxymethylcellulose, alginates, gelatin, polyvinyl pyrrolidone, sucrose and/or acacia; (3) humectants, such as glycerol; (4) disintegrating agents, such as sodium carboxymethylcellulose, sodium starch glycolate, crospovidone, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, sodium stearyl fumarate, silica oxide, solid polyethylene glycols, sodium lauryl sulfate, and mixtures thereof, (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin, PVP, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner.

Examples of embedding compositions that can be used include polymeric substances and waxes. The active ingredient can also be in micro-encapsulated form, if appropriate, with one or more of the above-described excipients.

The composition may further include components adapted to improve the stability or effectiveness of the applied formulation. Suitable preservatives include, but are not limited to: ureas, such as imidazolidinyl urea and diazolidinyl urea; chlorphenesin; methylisothiazolinone; phenoxyethanol; sodium methyl paraben, methylparaben, ethylparaben, and propylparaben; ethylhexyl glycerin; potassium sorbate; sodium benzoate; sorbic acid; benzoic acid; caprylyl glycol; formaldehyde; phytosphingosine; citric acid; sodium citrate; zinc citrate; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; piroctone olamine; *Vitis vinifera* seed oil; and alcoholic agents, for example, chlorobutanol, dichlorobenzyl alcohol, phenylethyl alcohol, and benzyl alcohol. Preservatives may be present in an amount of from about 0.05 to about 5 mg/mL such as from about 0.1 to about 1 mg/mL e.g. about 0.5 mg/mL.

Suitable antioxidants include, but are not limited to, ascorbic acid and its esters, sodium bisulfite, butylated hydroxytoluene, butylated hydroxyanisole, tocopherols (such as α-tocopherol), tocopheryl acetate, superoxide dismutase, oxidoreductases, *Arabidopsis thaliana* extract, chrysin, black raspberry seed oil, raspberry seed oil, pomegranate seed oil, cranberry seed oil, sodium ascorbate/ascorbic acid, ascorbyl palmitate, propyl gallate, and chelating agents like EDTA (e.g., disodium EDTA), citric acid, and sodium citrate.

In addition, combinations or mixtures of preservatives or anti-oxidants may also be used.

Suitable buffer salts also may be added. Examples include, but are not limited to sodium citrate, citric acid, sodium phosphate monobasic, sodium phosphate dibasic, sodium phosphate tribasic, potassium phosphate monobasic, potassium phosphate dibasic, and potassium phosphate tribasic.

Suitable viscosity adjusting agents (i.e., thickening and thinning agents or viscosity modifying agents) also may be added and include, but are not limited to, protective colloids or non-ionic gums such as hydroxyethylcellulose, xanthan gum, and *sclerotium* gum, as well as magnesium aluminum silicate, silica, microcrystalline wax, beeswax, paraffin, and cetyl palmitate. Cross-polymers of acrylates/$C_{10-30}$ alkyl acrylate are also considered. In addition, appropriate combinations or mixtures of these viscosity adjusters may be utilized.

Additional constituents include, but are not limited to: epithelium protectants, adsorbents, anti-oxidants, coating agents, coloring agents, demulcents, emollients, moisturizers, sustained release materials, solubilizing agents, epithelium-penetration agents, soothing agents, vitamins, anti-irritants, absorbents, anti-caking agents, anti-static agents, astringents (e.g., witch hazel, alcohol, and herbal extracts such as chamomile extract), binders/excipients, buffering agents, chelating agents, film forming agents, conditioning agents, opacifying agents, lipids, immunomodulators, sweeteners, flavoring agents, perfuming agents, antimicrobial agents and pH adjusters (e.g., citric acid, sodium hydroxide, and sodium phosphate).

For example, lipids normally found in healthy epithelium (or their functional equivalents) may be incorporated into emulsions. In certain embodiments, the lipid is selected from the group consisting of ceramides, cholesterol, and free fatty acids. Examples of lipids include, but are not limited to, ceramide 1, ceramide 2, ceramide 3, ceramide 4, ceramide 5, ceramide 6, hydroxypropyl bispalmitamide MEA, and hydroxypropyl bislauramide MEA, and combinations thereof.

Examples of peptides that interact with protein structures of the dermal-epidermal junction include palmitoyl dipeptide-5 diaminobutyloyl hydroxythreonine, palmitoyl tripeptide-5, acetyl octapeptide-3, pentapeptide-3, palmitoyl dipeptide-5 diaminohydroxybutyrate, dipeptide diaminobutyroyl benzylamide diacetate, palmitoyl tetrapeptide-7, palmitoyl oligopeptide, and palmitoyl dipeptide-6 diaminohydroxybutyrate.

Examples of epithelium soothing agents include, but are not limited to algae extract, mugwort extract, stearyl glycyrrhetinate, bisabolol, allantoin, aloe, avocado oil, green tea extract, hops extract, chamomile extract, colloidal oatmeal, calamine, cucumber extract, and combinations thereof.

Examples of vitamins include, but are not limited to, vitamins A, B, B5, D, E, K, and combinations thereof. Vitamin analogues are also contemplated; for example, the vitamin D analogues calcipotriene or calcipotriol.

Suitable fragrances, flavors, sweetening agents, and colors may be used in the compositions described herein. Examples of sweetening agents include sucrose or saccharin; Examples of flavoring agents include peppermint, methyl salicylate, or orange flavoring. Further examples of fragrances, flavors, and colors suitable for use in buccal products are known in the art.

Taste Modifying Additives

As noted above, oltipraz is an extremely bitter compound that can elicit aversion, revulsion, nausea, gagging and/or vomiting when administered in liquid form. Accordingly, in this disclosure flavoring additives or taste masking additives are typically used to make the liquid oltipraz compositions described above more palatable. Flavoring additives are additives that impart a particular flavor. Taste-masking additives are additives that tend to cover part of the taste of another component in the mixture, either with or without imparting a taste of their own. For example, in certain embodiments, taste-masking additives are used to suppress the bitterness of the oltipraz composition and thereby allow other flavors to emerge.

Because oltipraz is so bitter, flavoring and/or masking the taste of liquid oltipraz compositions to achieve a composition that is sufficiently palatable to be administered orally can be difficult, especially when the composition is to be orally administered (i.e. is for oral administration) to patients who have oral mucositis from undergoing radiation for cancers of the mouth and/or neck. Such patients often have sores on the inside of their mouth, and the radiation and/or mucositis can significantly affect their sensations of taste, especially as their radiation treatments progress and/or as their mucositis becomes worse. For example, by the second or third radiation treatment (and/or second or third week of radiation treatment), patients can start to become extremely sensitive to intense flavors such as mint or sweetness. That is, concentrations of mint or sweetness that are normally tolerable or even pleasant to a person who does not have mucositis and/or who has not undergone radiation treatments become intolerable for patients who have oral mucositis and/or who have undergone radiation treatments in the head and/or neck region. Hence, for compositions of this disclosure, additives that provide flavor and/or mask the bitterness of the oltipraz are typically added in order to provide a liquid composition that is sufficiently palatable to ensure patient compliance with the prescribed protocol.

Typically, the liquid oltipraz compositions of this disclosure include at least one additive that provides an immediate, rapid onset of flavor or other sensation such as cooling to suppress or mask the initial bitterness of the liquid oltipraz compositions. Often, the additive that provides this initial impact and suppression of bitterness is a natural mint flavor, which can impart an immediate cooling effect that substantially reduces the sensation of bitterness. The mint may be provided by a natural mint flavoring, e.g., peppermint oil, spearmint oil, or wintergreen, and/or an artificial mint flavoring. Alternatively, a menthol flavoring may be used to provide an initial burst of flavor or an immediate cooling effect cooling that can suppress the bitterness of the oltipraz. Both mint and menthol flavors may be employed.

Depending on the amount of oltipraz in the liquid composition, when mint flavoring is used, the mint flavor may be in concentrations of from 0.00001 to 0.1 percent by weight. In certain embodiments, the concentration of the mint is kept extremely low, allowing use by patients who have become very sensitive to mint. The concentration of the mint flavoring is typically from about 0.0005 to about 0.005 wt %, such as from about 0.0007 to about 0.003 wt % e.g. from about 0.0009 to about 0.001 wt %. For example, within the foregoing range are ranges from 0.0005 to 0.005, 0.0007 to 0.003, and about 0.0009 percent by weight. For example, in an embodiment, 0.0001 mL of mint (supplied by Mane Inc. as M30862, and having a density of 0.900) in 10 mL of water can provide an acceptable amount of mint for a composition comprising 50 mg of a dry, oltipraz-containing composition as described herein. (See Example 9 below.)

The mint and/or menthol flavor or sensation is relatively short-lived, thus, in certain embodiments the composition comprises a flavoring additive or additives that can suppress the bitterness after the sensation of the mint diminishes. For example, such flavoring can be provided by a sweet berry flavor, which may be comprised of a single, sweet berry flavoring additive, or a combination of ingredients that combine to provide both the berry and the desired sweetness. Alternatively, or in addition to the berry flavor, one or more fruit flavor additives can be employed.

The berry flavoring may be selected from any known berry flavor, e.g., barberry, Oregon-grape, mayapple, strawberry tree, strawberry, bearberry, bilberry, blueberry, cranberry, crowberry, coffee berries, gooseberry, currant, aubergine/eggplant, tomato, goji berries, elderberry, Indian gooseberry, Garcinia gummi-gutta, Garcinia mangostana, Garcinia indica, sapodilla, sapotaceae, grape, *Vitis vinifera*, honeysuckle berries, persimmon, pumpkin, cucumber, watermelon, grape, cherry and raspberry. Fruit flavoring also may be used, e.g., apple, banana, pineapple and citrus fruits such as lemon, lime, orange, flavoring. The berry flavoring agent(s) may be added in an amount that provides a suitable taste profile, and different agents will be added in different amounts, depending on the amount of the other flavoring additives and taste-masking agents that are used. The additive is typically selected from a flavor of one or more berries that naturally have a red and/or orange color so as to more closely align with or match the orange-red color of the oltipraz crystals, e.g., raspberry, strawberry, blackberry and/or blueberry. Such fruit flavoring is also available as a mixture, e.g., Forest Fruit M60056 sold by Mane Inc., which includes flavors of raspberry, blackberry and blueberry. Alternatively, a fruit flavor of a yellow fruit, e.g., banana, or an exotic fruit, e.g., kiwi, mango, star fruit, *papaya*, dragon fruit, coconut, or guava, or may be a mixture of fruit flavors such as tutti frutti. The concentration of the berry and/or fruit flavoring can vary from 0.01 to 1 percent by weight or more. Typically, the concentration of the berry and/or fruit flavoring is from about 0.05 to about 0.5%, such as from about 0.1 to about 0.4%, e.g. from about 0.2 to about 0.3%, such as about 0.24 percent by weight. Within that range are ranges 0.05 to 0.5%, 0.1 to 0.4%, 0.2 to 0.3%, and about 0.24 percent by weight. For example, 0.024 mL of Forest Fruit M60056 (density=1.043 g/mL) in 10 mL of water can provide an acceptable amount of berry flavoring for a composition comprising 50 mg of a dry, oltipraz-containing composition as described herein, provided that additional sweetening agent is added. (See the discussion below and also Example 9.) A sweetness mitigating additive, e.g., a citrus flavoring additive can be included to mitigate the sweetness of the sweet berry flavor.

Compositions can also comprise one or more citrus flavoring additives, e.g., orange, lemon, lime, and grapefruit. The citrus flavor can be combined with at least one organic acid, e.g., ascorbic acid, citric acid, tartaric acid, malic acid, lactic acid, and/or oxalic acid to improve the perception of the citrus flavor. The citrus flavor, and optionally the organic acid, may be added in an amount that provides a suitable taste profile, and different agents will be added in different amounts, depending on the other flavors and sweeteners in the composition. However, it is typically desirable to avoid addition of organic acids, e.g., for patients with sores in their mouths or whose mouths are otherwise sensitive to an organic acid.

Alternatively, or in addition to the berry and/or fruit flavor, one or more "brown note" flavors may be provided, e.g., caramel, vanilla and chocolate. Such flavors tend to be alkaline and thus may be better tolerated by patients who have sensitive mouths and/or sores in their mouths.

In circumstances where the berry and/or fruit and/or brown note flavoring is insufficiently sweet for the desired flavoring effect, at least one sweetening agent is typically added to help increase the sweetness of the composition and/or potentiate the berry, fruit and/or brown note flavor. Pharmaceutically acceptable sweeteners include sugars, including monosaccharides, disaccharides, and oligosaccharides, alcohols, and high-potency sweeteners. Examples of such high-potency sweeteners include aspartame, saccharin, neotame, acesulfame potassium, xylitol, sorbitol, mannitol, sucrose, fructose, glucose, maltose, lactose, xylose, and/or sucralose. The sweetening agent(s) may be added in an amount that provides a suitable taste profile, and different sweeting agents will be added in different amounts. High potency sweeteners like sucralose, aspartame and/or acesulfame potassium likely will be used in lower concentrations than natural sweeteners. Combinations of aspartame and acesulfame potassium may be used to provide a taste profile more closely aligned with the taste profile of natural sugar. Sucralose may be used generally where sweetness is desired.

As noted above, patients undergoing radiation treatment can start to become extremely sensitive to sweetness, especially as their radiation treatments progress and/or as their mucositis becomes worse. Typically, the amount of sweetener required to achieve an acceptable taste for such individuals is less than the amount that would be typically be required to achieve an acceptable taste for individuals who are not undergoing such treatment. For example, sucralose may be used in concentrations of 0.001 mg/mL of liquid composition up to 10 mg/mL. Typically, the concentration of sucralose is from about 0.001 to about 0.01 mg/mL, such as from about 0.01 to about 0.1 mg/mL, e.g. from about 0.1 to about 1.5 mg/mL, such as about 0.5 to about 1 mg/mL, e.g. about 0.8 mg/mL. Within such ranges are ranges of 0.001 to 0.01, 0.01 to 0.1, 0.1 to 1.5 mg/mL, 0.5 to 1 mg/mL, and about 0.8 mg/mL. For example, 8 mg of sucralose in 10 mL of water can provide an acceptable sweetening for a composition comprising 50 mg of a dry, oltipraz-containing composition as described herein. (See Example 9).

When berry, fruit and/or brown note flavoring are employed, either with or without the sweetener, the composition optionally can comprise at least one agent that provides an extended or longer lasting flavor that masks the bitterness and/or provides a sensation of cooling or freshness after the effect of the berry flavoring (with or without sweetener) diminishes. Such an extended effect of cooling or freshness can be provided with or without a mint taste. For example, the Physcool® family of flavors from by Mane Inc. can provide an extended sensation of coolness without mint taste, and can serve to help reduced the perceived bitterness, including any bitter aftertaste, of the oltipraz composition. Such agents may be added in an amount that provides a suitable taste profile, and different agents will be added in different amounts, depending on the other ingredients in the composition. In compositions comprising one or more of the Physcool® flavors, the amount can be adjusted so as to provide an extended refreshing or coolness sensation. Too much Physcool® flavoring, however, can yield a sensation that is overbearing to the point of being unpleasant. As noted above, patients undergoing radiation treatment can start to become extremely sensitive to different flavors and so the amount of additive to achieve an extended sensation of freshness or cooling may be less than the amount that would be required to achieve an acceptable taste for individuals who are not undergoing such treatment. For example, when a Physcool® flavoring is used, the Physcool® flavoring may be added in an amount of from 0.001 to 0.1 percent by weight. The amount of Physcool® flavoring is typically from about 0.01 to about 0.05%, such as about 0.025 percent by weight. Within that range are ranges 0.01 to 0.05%, and about 0.025 percent by weight. For example, 0.0025 mL of Physcool® Synergy M0059829 (density=1.032) supplied by Mane Inc. in 10 mL of water can provide an acceptable amount of extended sensation of cooling or freshness for a composition comprising 50 mg of a dry, oltipraz-containing composition as described herein. (See Example 9).

Additionally, dyes or coloring may be added to alter the color of the liquid from the natural orange color imparted by the oltipraz crystals, e.g., to more closely align the color with the flavoring that is added. For example, if red berry flavors are employed as discussed above, then red dyes or coloring may be added to make the composition appear redder to more closely align with the flavors.

The above flavoring additives may be added to any of the oltipraz compositions described herein to provide pharmaceutical compositions that may be used in any of the processes described herein for treating patients. Typically the compositions will be liquid and comprise water, but may comprise a non-aqueous solvent instead of, or in addition to, water.

One or more additional agents that are generally recognized as safe for administration to humans and can be co-administered together with the oltipraz composition, or co-administered separately as part of a dosing regimen with the oltipraz composition, include N acetylcysteine and/or other antioxidants. BHT, pantothenic acid (vitamin B5) or other agents that enhance glutathione synthesis, glutathione, e.g., for topical administration, Medihoney (for topical administration), curcumin (for topical administration) or other NF-kappaB inhibitors, Mesalamine and/or other anti-inflammatory agents, e.g., for oral or rectal administration compositions, and superoxide dismutase or other compounds that prevent damage from reactive $O_2^-$ (superoxide).

Devices for Oral Administration

In certain embodiments, liquid formulations for oral administration may be prepared and administered using a device that facilitates administration of a single dose of the pharmaceutical composition. Such devices, which are known in the art, can include a cavity or reservoir where a dry composition and a liquid such as water and/or a non-aqueous solvent may be mixed and then administered to the patient via an opening in the device. Typically, such devices comprise a compartment, separate from the cavity, where a dry powder can reside. At the time of administration, the powder is released from the compartment into the cavity or reservoir, and in some embodiments, by breaking a barrier that separates the compartment from the cavity or reservoir. Thereafter, the powder may be mixed, typically by shaking, with a liquid in the cavity that may have been added earlier or at the time. The cavity is of sufficient size to hold both the dry pharmaceutical composition and a quantity of liquid comprising an amount of water and/or non-aqueous solvent sufficient to permit mixing of the dry pharmaceutical composition to form a liquid composition. The liquid may be added to the container at the time of packaging to create a self-contained product comprising both dry composition and liquid that may be mixed together at the time of administration. Alternatively, the container can contain only a dry pharmaceutical composition and the liquid is then added prior to administration. The liquid may contain flavoring additives as discussed below. Alternatively, the powder and the liquid can be sealed in 2 form-fill-and-seal pouches, either side by side or one on top of the other and separated by a rupturable seal. The person administering the drug would then rupture the seal and mix the contents back and forth between the 2 compartments until dissolved.

Once the composition is substantially homogeneous (e.g., from the shaking), it is then administered to the patient via an opening in the device created, e.g., by uncoupling a portion of the device to expose the cavity containing the liquid mixture. For example, a portion of the device, e.g., the top, can be removed by unscrewing a threaded portion from another threaded portion of the container to expose the cavity containing the liquid mixture, which then may be administered to the patient or by the patient. Examples of such devices are provided in U.S. Pat. No. 6,148,996, U.S. application 20080202949, and U.S. Pat. No. 3,156,369. Such single-use devices can be employed for orally administering liquid compositions described herein, especially for prophylaxis or treatment of oral mucositis or its symptoms as described below.

The disclosure thus also provides a kit comprising (i) oltipraz crystals or a composition comprising oltipraz crystals as described herein and (ii) a device for oral administration of such crystals or compositions. The kit optionally further contains instructions for use.

Compositions for Topical Administration

In some embodiments, the formulations may be suitable for topical administration, and may include any of the constituents outlined below.

Suitable moisturizers for use in the formulations include, but are not limited to, lactic acid and other hydroxy acids and their salts, glycerol, propylene glycol, butylene glycol, sodium PCA, sodium hyaluronate, Carbowax 200, Carbowax 400, and Carbowax 800.

Suitable humectants include, but are not limited to, panthenol, cetyl palmitate, glycerol (glycerin). PPG-15 stearyl ether, lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, *Theobroma grandiflorum* seed butter, sunflower seed oil, ceramides (e.g., ceramide 2 or ceramide 3), hydroxypropyl bispalmitamide MEA, hydroxypropyl bislauramide MEA, hydroxypropyl bisisostearamide MEA, 1,3-bis(N-2-(hydroxyethyl) stearoylamino)-2-hydroxy propane, bis-hydroxyethyl tocopheryl-succinoylamido hydroxypropane, urea, aloe, allantoin, glycyrrhetinic acid, safflower oil, oleyl alcohol, oleic acid, stearic acid, dicaprylate/dicaprate, diethyl sebacate, isostearyl alcohol, pentylene glycol, isononyl isononanoate, polyquaternium-10 (quaternized hydroxyethyl cellulose), *camellia* oleifera leaf extract, phytosteryl canola glycerides, shea butter, caprylic/capric triglycerides, punica granatum sterols, ethylhexyl stearate, betaine, behenyl alcohol (docosanol), stearyl alcohol (1-octadecanol), *laminaria ochroleuca* extract, behenic acid, caproyl sphingosine, caproyl phytosphingosine, dimethicone-divinyldimethicone-silsesquioxane crosspolymer, potassium lactate, sodium hyaluronate crosspolymer, hydrolyzed hyaluronic acid, sodium butyroyl-formoyl hyaluronate, polyglutamic acid, tetradecyl aminobutyroylvalylaminobutyric urea trifluoroacetate, *micrococcus* lysate, hydrolyzed rice bran protein. *glycine soja* protein, and 1.3 bis(N-2-(hydroxyethyl)palmitoylamino)-2-hydroxypropane.

The topical compositions also may be delivered transdermally via a patch that is applied over the skin, and such patches are well known in the art.

Persons of skill in the art will recognize other topical delivery compositions and vehicles that may be used.

Compositions for Recta/Colonic Delivery

In certain embodiments, the pharmaceutical compositions can be formulated for rectal administration to provide colon-specific delivery using known methods and compositions. Generally speaking, delivery of pharmaceutical composition via rectal administration route can be achieved by using suppositories, enemas, ointments, creams or foams. Suppositories are among the most common rectal dosage forms, and bases are generally fatty in nature, but water-soluble or water-miscible bases can also be utilized. In order to achieve a desirable bioavailability the active ingredient should come in contact with the rectal or colonic mucosa.

Suitable excipients for preparing compositions for rectal administration such as, but not limited to, vehicle, preservatives, surfactants, emulsifiers, mineral oils, propellants, thickening agents, lubricants, preservatives, pH adjusting agents, chelating agents, emollients and/or humectants, permeation enhancers, suspension-forming agents or mucoadhesive agents or combinations thereof. The vehicle may include an aqueous, non-aqueous or a hydro-alcoholic vehicle. Suitable aqueous vehicles which are compatible with the rectal and colonic mucosa, may comprise water soluble alkanols selected from, but not limited to, ethanol, polyalcohols such as a propylene glycol, glycerol, polyethyleneglycol, polypropylene glycol, propylene glycol glyceryl esters and combinations thereof. Non-aqueous vehicles which may be employed in pharmaceutical rectal foam compositions, including but not limited to vegetable oils, such as olive oil; injectable organic esters, such as ethyl oleate and combinations thereof.

Suitable surfactants that may be employed in pharmaceutical compositions for rectal administration, e.g. anionic surfactants, non-ionic surfactants, cationic surfactants, and amphoteric (zwitterionic) surfactants. Anionic surfactants may include, but are not limited to, ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinate, disodium lauryl sulfosuccinate, diammonium lauryl sulfosuccinate, tetrasodium N-(1,2-dicarboxyethyl)-N-octadecylsulfosuccinate, diamyl ester of sodium sulfosuccinic acid, dihexyl ester of sodium sulfosuccinic acid, dioctyl esters of sodium sulfosuccinic acid, docusate sodium, and combinations thereof.

Nonionic surfactants may include, but are not limited to, polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethylene oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof.

Amphoteric surfactants may include, but are not limited to, sodium N-dodecyl-beta-alanine, sodium N-lauryl-beta-iminodipropionate, myristoamphoacetate, lauryl betaine, lauryl sulfobetaine, sodium 3-dodecyl-aminopropionate, sodium 3-dodecylaminopropane sulfonate, sodium lauroamphoacetate, cocodimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, oleamidopropyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and combinations thereof.

Cationic surfactants may include, but are not limited to, behenyl trimethyl ammonium chloride, bis(acyloxyethyl) hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowediimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, lautrimonium chloride, methyl-1-oleyl amide ethyl-2-oleyl imidazolinium methyl sulfate, picolin benzyl ammonium chloride, polyquatemium, stearalkonium chloride, stearyl dimethylbenzyl ammonium chloride, stearyl trimethyl ammonium chloride, trimethylglycine, and combinations thereof.

Suitable thickening agents or viscosity modifying agents which may be employed in the pharmaceutical composition for rectal administration include, but are not limited to, carboxymethyl cellulose, polyoxyethylene-polyoxypropylene copolymers, xanthan gum, agar, guar gum, hydroxyethyl cellulose, hydroxypropyl cellulose, methyl cellulose and combinations thereof.

Alternatively, colonic absorption can be accomplished through oral administration of compositions designed to release the active oltipraz in the colon. Such compositions can be in an oral dosage form. e.g., a pill or capsule, that provides delayed release until the dosage form is in the colon Compositions and Devices for Inhalation Administration In other embodiments, oltipraz-containing compositions may be delivered via the respiratory tract by providing the composition in inhalable form, e.g., in an inhaler device, either in dry powder form or in a liquid carrier. For example, inhalable compositions can comprise the active ingredient in dry powder compositions provided in dry powder inhalers. See, e.g., WO2014177519 and US20140065219. Alternatively, inhalable compositions can comprise the active ingredient in a liquid carrier such as ethanol. See, e.g., EP2536412 A2.

The disclosure thus also provides a kit comprising (i) oltipraz crystals or a composition comprising oltipraz crystals as described herein and (ii) a device for administering such crystals or compositions by inhalation. The kit optionally further contains instructions for Use.

F. Methods of Treating

In certain embodiments, the pharmaceutical compositions may be used for treating a human or non-human animal patient in need. The patient typically will be a human patient, although the pharmaceutical compositions of this disclosure can be used for treating non-human animals, e.g., for veterinary uses. The compositions of this disclosure may be used for preventing or treating a wide variety of diseases and conditions, including diseases and conditions for which treatment with oltipraz is known. Examples of such diseases and conditions include mucositis, HIV, cancers, hepatitis (including HBV and HCV), keratin-based skin diseases, including skin blistering and epidermolysis bullosa simplex and related diseases, inflammatory disorder or disease (including endothelial dysfunction and cardiovascular disease), sepsis, contrast-induced nephropathy, diabetes, obesity. PCOS, steatosis, hyperlipidemia, and hypertension, chronic kidney disease, pulmonary fibrosis, hypoxic conditions, chemical-induced lung injury, respiratory distress disorder, anon gap acidosis, nephritis, lupus, interstitial lung disease, graft dysfunction, hepatitis, acute kidney injury, noise-induced hearing injuries, poison ingestion, retinopathy, neurotoxicity, cancer-induced injury such as ototoxicity, respiratory infections, autism, conditions involving vasospasm, and conditions considered treatable by provision of n-acetylcysteine, injectable reduced glutathione, or a known intracellular glutathione enhancing agent.

Typically, the composition is provided to the patient in an effective amount. The term "effective amount" is used herein to refer to an amount of the therapeutic composition sufficient to produce a significant biological response (e.g., a significant decrease in inflammation). Actual dosage levels of the oltipraz in a therapeutic composition can be varied so as to administer an amount that is effective to achieve the desired therapeutic response for a particular subject and/or application. Of course, the effective amount in any particular case will depend upon a variety of factors including formulation, route of administration, combination with other drugs or treatments, severity of the condition being treated, and the physical condition and prior medical history of the subject being treated.

As used herein, the term "subject" includes both human and animal subjects, and thus veterinary therapeutic uses are provided in accordance with this disclosure. The terms "treatment" or "treating" relate to any treatment of a condition of interest (e.g., mucositis, an inflammatory disorder or a cancer), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

The compositions are suitable for treating patients who are suffering from mucositis. e.g., in the oral cavity (including in the buccal cavity), in the alimentary canal, in the colon and/or rectum, and/or on the skin. Such patients, e.g., may be undergoing chemotherapy and/or radiation therapy. e.g., radiation treatment in the head and neck area, or to another area of the body. Such compositions may be used to accomplish one, more than one, or all of the following beneficial effects on human or non-human animal patients, i.e., (i) prophylactically prevent or delay the onset of mucositis, including oral mucositis (e.g., inflammation of the mucosa), (ii) treat existing mucositis, including oral mucositis (iii) alleviate symptoms associated with mucositis, including oral mucositis (iv) reduce or lessen the severity of existing mucositis, including oral mucositis (v) hasten the cure or healing of mucositis, including oral mucositis (vi) reduce the incidence and/or duration of mucositis, including oral mucositis, e.g., mild, moderate and severe oral mucositis, (vii) prophylactically prevent or delay the onset of weight loss by a patient with oral mucositis, (viii) lessen the amount of weight loss experienced by a patient with oral mucositis, and/or (ix) increase the ability of a patient with oral mucositis to take food by mouth. Such compositions also may be used for the prevention and/or treatment of patients with dysphagia (difficulty swallowing), e.g., cancer patients, or to delay the onset of dysphagia or lessen the severity of dysphagia. e.g., in cancer patients. Such compositions also may be used for the prevention and/or treatment of patients with xerostomia (the subjective feeling of oral dryness), or to delay the onset of xerostomia, lessen the severity of xerostomia, and/or reduce the incidence of moderate-to-severe xerostomia. In certain embodiments, the single-use devices described above may be used for administration of liquid compositions for accomplishing one, more than one, or all of the above relating to oral mucositis, dysphagia and xerostomia. Advantageously, formulations are also non-irritating, well-tolerated, palatable (if orally administered), non-cytotoxic, weakly or non-sensitizing, non-sensitizing.

Certain embodiments herein provide methods for treating mucositis, comprising administering to a patient in need thereof a therapeutically effective amount of a composition as described herein. The disclosure also provides a composition as described herein for use in the treatment of mucositis. The disclosure also provides the use of a composition as described herein in the manufacture of a medicament for the treatment of mucositis. The administration of the formulation to a patient may be an oral administration, including buccal administration.

The methods of administration described herein can represent a treatment regimen of a predetermined duration, e.g., 1 month, 2 months, 3 months, 4 months, 5 months, 6 months, or longer. Compositions according to this disclosure can be applied or administered once daily, twice daily, three times daily, or as needed. In situations where the patient is undergoing chemotherapy and or radiation therapy, the dosage may be administered prior to a treatment. e.g., within 1 hour, within 3 hours, within 6 hours, within 12 hours, within 24 hours, or more than 24 hours before the treatment. Additionally, or alternatively, the dosage may be administered after a treatment, e.g., within 1 hour, within 3 hours, within 6 hours, within 12 hours, within 24 hours after the treatment, or more than 24 hours after the treatment.

Where liquid compositions are administered, the composition may be administered orally or parenterally, e.g., by subcutaneous, intramuscular, intrasternal, or intravenous injection. Where oral administration is employed, the liquid composition simply may be swallowed, or it may be administered by a "swish and swallow" regimen or a "swish and spit" regimen. By administering the composition orally in a liquid form to a patient with oral mucositis, the compositions may provide a therapeutic dosage of oltipraz at the site of administration, which can provide a therapeutic benefit in terms of the mucositis as described above, i.e., it may prophylactically prevent the onset of mucositis, treat existing mucositis, alleviate symptoms associated with mucositis (e.g., inflammation of the mucosa), reduce or lessen the severity of existing mucositis, and/or hasten the cure or healing of mucositis. In such cases, liquid compositions comprising an ingredient with a negative charge, e.g., a cationic surfactant or polymer such as Eudragit RL, may provide a further advantage by virtue of providing an adherence or association with the mucosa of the mouth, which tends to have a positive charge. The physical and chemical properties of embodiments of the compositions described herein can impart characteristics to the formulation such as stability, delivery of the active agent to the mucosal membrane, and ease of administration.

As noted above, oltipraz compositions as described herein may be co-administered with other therapeutic agents, either together or separately as part of a therapeutic regimen. Such agents include N acetylcysteine and/or other antioxidants, pantothenic acid (vitamin B5) or other agents that enhance glutathione synthesis, glutathione, e.g., for topical administration, Medihoney (for topical administration), curcumin (for topical administration) or other NF-kappaB inhibitors. Mesalamine and/or other anti-inflammatory agents, e.g., for oral or rectal administration compositions, and superoxide dismutase or other compounds that prevent damage from reactive $O_2$ (superoxide).

EXAMPLES

Certain embodiments of this disclosure are further illustrated by the following examples, which should not be construed as limiting in any way.

Example 1: Method for Manufacturing an Oltipraz Composition

A pharmaceutical composition comprising oltipraz, stabilizing agents polysorbate 80 and Eudragit RL, and a bulking polymer, polyvinylpyrrolidone vinylacetate (PVP-VA64), was manufactured by the following steps.

In an appropriate sized container with agitator, formulation components were added in the following order: stabilizing polymer, purified water, polysorbate 80, then oltipraz. The mixture was stirred to create a homogeneous suspension vehicle. The composition of the suspension vehicle prior to milling is shown in Table 2. The suspension vehicle was milled in a temperature controlled grinding chamber (such as a Dyno-mill, model KDL) with 0.5 mm yttrium-stabilized zirconium oxide spheres as a grinding media. A list of additional mill parameters is shown in Table 3. Total milling time of the suspension was 270 minutes, determined based on a target mean residence time of 7 minutes in the grinding chamber (see Equation 1). The MHD of the crystals/particles in the milled suspension was measured by dynamic light scattering (DLS) performed as described above and was 330 nm.

The milled suspension was transferred to a new, appropriate sized solution tank, bulking polymer PVP-VA64 was added, and then additional purified water to dilute the suspension to 28% total solids. The final suspension composition shown in Table 4 was then stirred for at least 30 minutes. The suspension was spray dried with a Niro PSD-1 spray dryer using parameters shown in Table 5. Spray dried powder was collected in a cyclone.

TABLE 2

Composition of Suspension Vehicle

| Component | Function | Composition (weight percent of suspension) |
|---|---|---|
| Eudragit RL | Stabilizing agent | 4.3 |
| Polysorbate 80 | Stabilizing agent | 2.1 |
| Oltipraz | Active | 8.6 |
| Water, USP Purified | Solvent | 85.0 |

TABLE 3

Parameters Used with the Dyno-mill KDL

| Parameter | Value |
|---|---|
| Chamber size | 0.6 L |
| Agitator Paddles | 64 mm |
| Gap size | 0.2 mm |
| Rotor Speed | Approximately 3000 rpm (belt position 3) |
| Mill mode | Continuous |
| Grinding media volume | 2000 g |
| Suspension Temperature (Reservoir) | 2.0-40.0° C. |
| Suspension Temperature (Mill outlet) | 2.0-40.0° C. |
| Suspension Flow Rate | 500 mL/min |
| Mill Run Time | 270-300 minutes |

Example calculation for total required milling time of suspension vehicle.

$$\frac{\text{Working chamber volume}}{F} * \text{total mill time} = 7 \text{ minutes}$$

$$\text{where } F = \frac{\text{total suspension mass}}{\text{suspension density}}$$

Working chamber volume was defined as the empty chamber volume minus the volume of the grinding media.

TABLE 4

Composition or Spray Suspension

| Component | Function | Composition (% of suspension) |
|---|---|---|
| Milled Suspension (from Table 1) | — | 48.7 |
| PVP-VA 64 | Bulking polymer | 20.7 |
| Water, USP Purified | Solvent | 30.6 |

TABLE 5

Spray Drying Process Conditions on a PSD-1 Scale Spray Dryer

| Process Condition | Value |
|---|---|
| Atomizer | Spray Systems 2-fluid 2850/120 |
| Atomization gas pressure (psig) | 20 |
| Drying-gas inlet temperature (° C.) | 105 |
| Drying-gas outlet temperature (° C.) | 50 |
| Solution flow rate (g/min) | 35 |
| Drying-gas flow rate (g/min) | 1850 |

The spray dried powder was analyzed to confirm the powder re-suspended in water within 2 minutes, and the resulting oltipraz milled crystal size was similar to the original crystal size achieved during the milling step. Two tests were performed: first, the powder was re-suspended in water at an oltipraz concentration of 5 mg/mL and the time to uniform suspension by visual observation was recorded. Second, the resulting crystal size of the suspension was measured by DLS. The spray dried powder re-suspended in water with vigorous shaking within 2 minutes, and the resulting suspension crystal size was 370 nm which was similar to the original milled suspension crystal size.

Example 2: Stability Testing of an Oltipraz Composition

Samples of a lot of a dry oltipraz composition similar to that prepared in Example 1 were subjected to stability testing for three months at 5° C., 25° C., and 60% relative humidity (RH), and 40° C., and 75% RH. The samples (10 g) were contained inside an LDPE (low density polyethylene) pouch, which was subsequently placed inside of a foil bag. Desiccant (1 g) was put in the foil bag, and then the foil bag was hermetically heat sealed. Results were as follows:

- Powder is still same intense orange.
- Flowability was poor due to static, as expected. There is no clumping at any condition.
- Re-suspension was performed at 5 mg/mL. It was very fast in that the powder re-suspended fully in less than 15 sec of shaking.
- DLS performed immediately after re-suspension showed particle size of re-suspended crystals remained less than 600 nm (see Table 6 below).
- At 3-month time point, 24 hour stability of suspension was tested. After initial test, suspension was left on counter 24 hours. Minor settling occurred during that time, but a 15 second shake re-suspended all. DLS showed particle size had not changed.
- Potency results were as expected, within error.
- Glass transition temperature and crystalline melt temperature of the spray dried crystals were unchanged at 3-months.

TABLE 6

Z-Average Particle Size (nm) by Intensity of Oltipraz Crystal Suspension in Water (average of n = 2)

| Condition | t = 0 | 1 Month | 3 Month | 3 Month + 1 day suspended |
|---|---|---|---|---|
| 5° C. | 370 | 422 | 377 | 299 |
| 25° C. and 60% RH | 370 | 412 | 325 | 302 |
| 40° C. and 75% RH | 370 | 393 | 324 | 314 |

FIG. 3*a* is a SEM image at 5000× magnification of the dry composition comprising oltipraz at t=0. FIG. 3*b* is a SEM image at 5000× magnification of the dry composition after stability testing for three months at 40° C., and 75% RH. FIG. 3*c* is a SEM image at 1500× magnification of the dry composition after stability testing for three months at 40° C., and 75% RH. As can be seen from the figures, particle morphology did not change over time under the test conditions. The particles are still raisin-like to spherical particles with no evidence of crystal growth or particle fusing.

Example 3: Study for the Assessment of Oltipraz Composition for the Treatment of Oral Mucositis Induced by Acute Radiation in Hamsters Twenty-four (24) male Syrian Golden Hamsters were used in the study. Mucositis was induced by giving an acute radiation dose of 40 Gy directed to the left buccal cheek pouch on Day 0. Mucositis was evaluated clinically starting on Day 6, and continuing on alternate days until Day 28. Placebo, recrystallized (neat) oltipraz, or a formulated oltipraz composition (described below) at a concentration of 5 mg/mL (based on the amount of crystals in the suspension) was administered by topical application of 0.2 mL directed to the left cheek pouch, twice daily (BID; 1 mg/dose; 2 mg/day) from Days −3 (first dose prior to irradiation) to Day 28.

The formulated oltipraz composition was prepared generally according to the process described in Example 1 and contained 16.7% wt/wt of nanomilled oltipraz crystals (MHD<350 nm) that has been formulated with Eudragit RL, Tween 80 and PVP-VA64 and spray-dried The neat oltipraz was recrystallized oltipraz prepared according to the process disclosed in WO2016207914.

Results and Conclusions

- There were no animal deaths at any time during this study.
- There were no significant differences in overall mean percent weight change between the placebo control group and the treatment groups from Day −3 to 28, although animals dosed with the formulated oltipraz composition gained substantially more weight and at a significantly faster rate than the animals that were administered neat oltipraz (FIG. 4A), indicating a biological difference in the level of activity.

The maximum mean mucositis score observed in the placebo group was 3.13±0.09 and occurred on Day 16. Animals dosed with neat oltipraz (Group 2) experienced peak mean mucositis score on Day 16 at 3.25±0.11. Animals dosed with the formulated oltipraz composition (Group 3) experienced peak mean mucositis score of 2.63±0.13 and first occurred on Day 14.

Mucositis Scoring

Mucositis was scored visually by comparison to a validated photographic scale, ranging from 0 for normal, to 5 for severe ulceration (clinical scoring). In descriptive terms, this scale is defined as described in Table 7 below:

TABLE 7

| Score | Description |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray color due to pseudomembrane. Cumulative size of ulcers should equal less than or equal to ¼ of the pouch. Severe erythema and vasodilation. |
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth). |

Figure 4A:
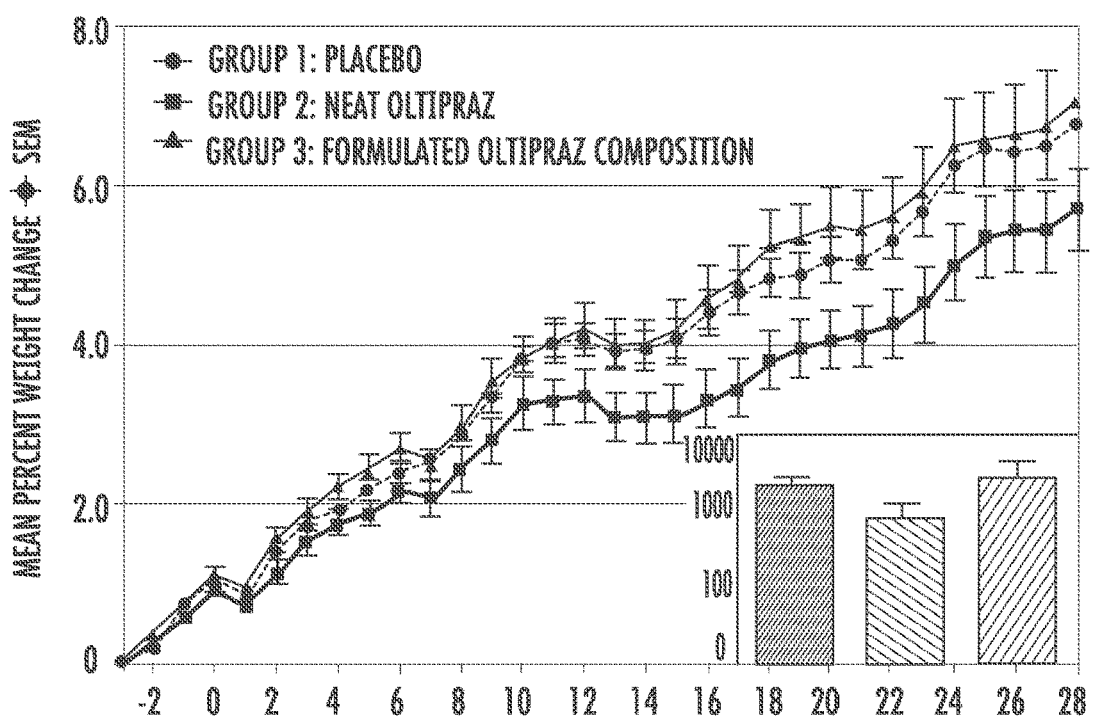
FIG. 4A is a graph of the mean percentage of weight change in the oral mucositis assessment described in Example 3.
Figure 4B:
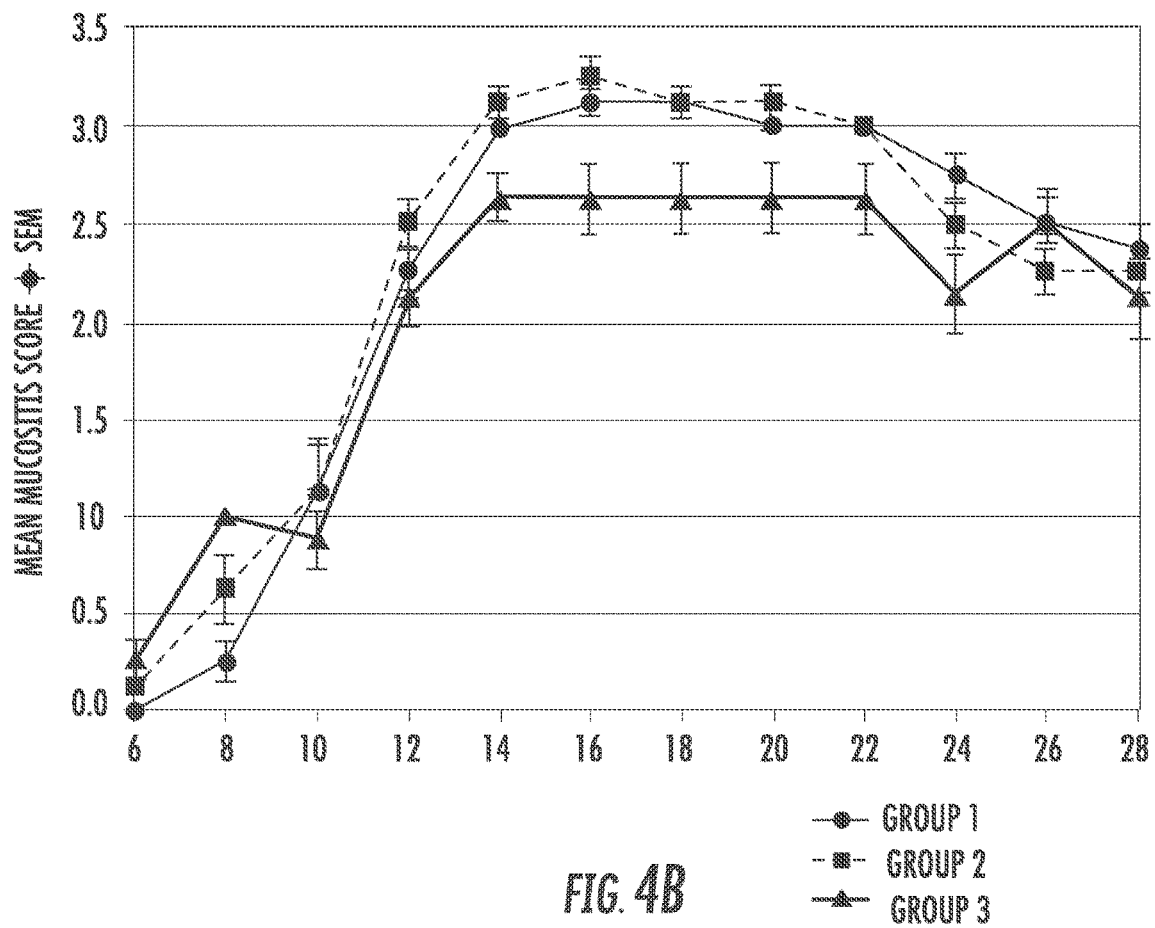
FIG. 4B is a graph of the mean daily mucositis scores in the oral mucositis assessment described in Example 3.

Mean daily blind mucositis scores are shown in FIG. 4B. Animals administered Placebo (Group 1) and animals administered neat oltipraz tracked closely together. The maximum mean mucositis score observed in the vehicle group was 3.13±0.09 and occurred on Day 16. Animals dosed with neat oltipraz (Group 2) experienced peak mean mucositis score on Day 16 at 3.25±0.11. In contrast, animals administered the formulated oltipraz composition (Group 3) displayed a substantially and observably reduced mucositis compared to animals administered Placebo (Group 1) or neat oltipraz (Group 2). Supporting this observation, animals receiving the formulated oltipraz composition (Group 3) displayed a peak mean mucositis score of only 2.63±0.13 on Day 16.

Over the course of the study, the percentage of animal days with an ulcerative mucositis (score of ≥3) in the placebo Group was 58.33%. In contrast, the percentage of animal-days with a score of ≥3 was dramatically lower for animals in administered the formulated oltipraz composition (43.75%; p=0.006).

Weight Change

The mean daily percent body weight change data are shown in FIG. 4A for animals in all groups. All animals gained weight steadily over the course of the study (Days −3 to 28), however, animals administered neat oltipraz (Group 2) gained weight at a slower rate than those administered placebo (Group 1) or those administered formulated oltipraz composition (Group 3), suggesting that administration of neat oltipraz may negatively impact weight gain. There were no significant differences in cumulative mean percent weight change between groups in comparing the area under the body weight versus time curve (AUC) analysis followed by evaluation with one-way ANOVA and Holm-Sidak's multiple comparisons test (inset), although as shown in FIG. 4A, the overall percentage weight change for the animals administered neat oltipraz (Group 2) was substantially less than rate than those administered placebo (Group 1) and lower still as compared against those administered formulated oltipraz composition (Group 3). The percentage rate of weight change for animals administered neat oltipraz was substantially less than the rate for those administered placebo or formulated oltipraz.

Duration of Ulcerative Mucositis

A mucositis score of 3 or greater indicates ulcerative mucositis, a clinically significant threshold. To quantify the clinical significance of differences observed between the control and treatment groups animal-days with mucositis scores ≥3 and <3 were compared between groups using chi-square analysis. The results of this analysis are shown in Table 8 and FIG. 5 for the entire study duration (through Day 28). Over the course of the study (Table 8, FIG. 5), the percentage of animal days with a score of ≥3 in the vehicle Group was 58.33%. The percentage of days with a score of ≥3 was dramatically and statistically lower for animals in Group 3 in comparison to the vehicle Group (Group 1; p<0.01).

Table 8 below provides a chi-square analysis of percent of animal days with a mucositis score ≥3. To examine the levels of clinically significant mucositis, as defined by presentation with open ulcers (score ≥3), the total number of days in which an animal exhibited an elevated score was summed and expressed as a percentage of the total number of days scored for each group. Statistical significance of observed differences was calculated using chi-squared analysis.

TABLE 8

Chi-Square Analysis of Percent of Animal Days with a Mucositis Score ≥ 3

| Treatment | Days ≥ 3 | Days < 3 | Total Animal Days | % Days ≥ 3 | Chi Sq vs. Vehicle | P Value |
|---|---|---|---|---|---|---|
| Group 1: Placebo | 112 | 80 | 192 | 58.33% | — | — |
| Group 2: Neat oltipraz | 104 | 88 | 192 | 54.17% | 0.519 | 0.471 |
| Group 3: Formulated oltipraz composition | 84 | 108 | 192 | 43.75% | 7.597 | 0.006 |

Figure 5:
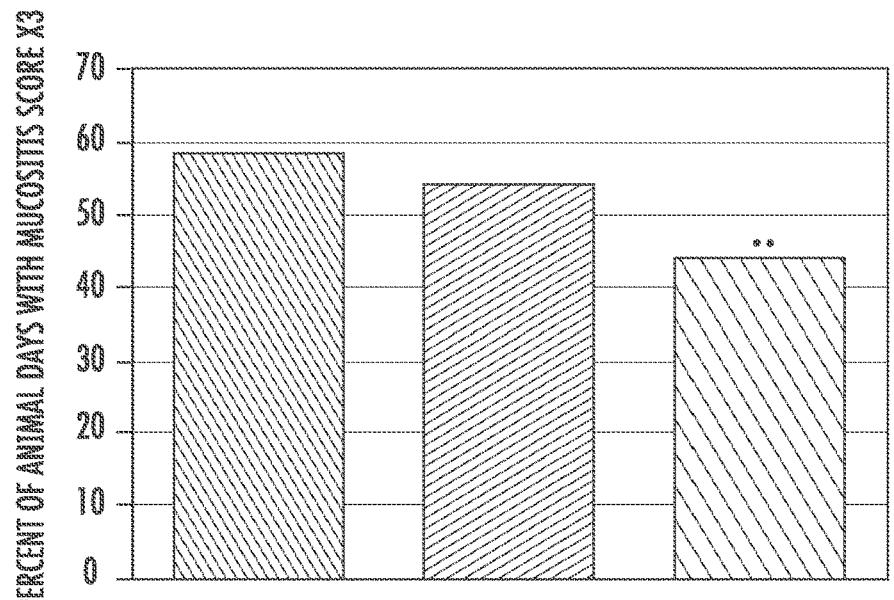
FIG. 5 is a graph of the chi-square analysis of the percent of animal days with a mucositis score ≥3 in the oral mucositis assessment described in Example 3.

FIG. 5 provides a graph of the percent of animal days with mucositis scores ≥3 for the entire study duration. To examine the levels of clinically significant mucositis, as defined by presentation with open ulcers (a score of ≥3), the total number of days in which an animal exhibited an elevated score was summed and expressed as a percentage of the total number of days scored for the entire study duration (Day 6-28). Statistical significance was evaluated using the Chi-square test in comparison to Vehicle Control; The statistical significance for the Group 3 results (**) was p<0.01.

Mucositis Severity

An analysis of the severity of mucositis was performed using the Mann-Whitney rank sum analysis to compare the visual mucositis scores for Groups 2 and 3 to the vehicle control group (Group 1) on each day of the analysis. The results of this analysis are shown in Table 9 below. In this analysis, 2 consecutive days of significant reduction in the mucositis score are generally required before it is regarded as clinically meaningful. Animals dosed with the formulated oltipraz composition (Group 3) demonstrated four instances of significant improvement in mucositis scores compared to the vehicle control group including a stretch of four consecutive days of statistically significant improvement (Days 14-18) compared to animals administered Placebo (Group 1).

To examine the levels of clinically significant mucositis, as defined by presentation with open ulcers (score >3), the percentage of animals from each treatment group that exhibited an open ulcer on each day of the study was determined. "y" denotes an increase in comparison to vehicle Group, "z" denotes decrease (improvement). The results show an improvement in the ulceration scores for the formulated oltipraz composition as compared to either the neat oltipraz or placebo. The results of day 26 appears to have been due to one animal flare from day 24 and the result of day 28 is likely due to the difference in a single animal score.

Conclusions

There were no animal deaths at any time during this study.

There were no significant differences in overall mean percent weight change between the placebo control group and the treatment groups from Day −3 to 28, although as shown in FIG. 4A, the overall percentage weight change for the animals administered neat oltipraz (Group 2) was substantially less than rate than those administered placebo (Group 1) and lower still as

TABLE 9

Comparison of Daily Mucositis Scores.

| Group | Rank Sum Analysis by Day | | | | | | | | | | | |
|---|---|---|---|---|---|---|---|---|---|---|---|---|
| | 6 | 8 | 10 | 12 | 14 | 16 | 18 | 20 | 22 | 24 | 26 | 28 |
| Placebo vs. Neat Oltipraz | 0.4839 | 0.1539 | 0.9181 | 0.2734 | 0.4839 | 0.6539 | 1.0 | 0.4839 | 1.0 | 0.2734 | 0.2734 | 0.7043 |
| Placebo vs. Formulated Oltipraz Composition | 0.1012 | <0.0001 x, y | 0.6774 | 0.7430 | 0.0177 x, z | 0.0321 x, z | 0.0321 x, z | 0.1012 | 0.1012 | 0.0242 x, z | 0.7224 | 0.4320 |

The significance of group differences observed in daily mucositis scores was determined using the Mann-Whitney rank sum test. This nonparametric statistic is appropriate for the visual mucositis scoring scale. The p-values for each calculation are shown. "x" denotes significant difference in mucositis scores. "y" denotes increase in comparison to vehicle Group (improvement), "z" denotes decrease.

Percent of Animals with Ulcerative Mucositis by Day

The percentage of animals in each group with ulcerative mucositis at each day of evaluation is shown in Table 10. This evaluation was intended to clarify which days of treatment had its maximal impact on the course of ulcerative mucositis. Fewer animals displayed ulcerative mucositis when administered the formulated oltipraz composition (Group 3) over ten consecutive day (Days 14-24) in comparison to the animals receiving Placebo (Group 1).

compared against those administered formulated oltipraz composition (Group 3).

The maximum mean mucositis score observed in the placebo group was 3.13±0.09 and occurred on Day 16. Animals dosed with neat oltipraz (Group 2) experienced peak mean mucositis score on Day 16 at 3.25±0.11. Animals dosed with the formulated oltipraz composition (Group 3) experienced peak mean mucositis score of 2.63±0.13 and first occurred on Day 14.

Over the course of the study, the percentage of animal days with an ulcerative mucositis (score of ≥3) in the placebo Group was 58.33%. In contrast, the percentage of animal-days with a score of ≥3 was dramatically lower for animals administered the formulated oltipraz composition (43.75%; p=0.006)

TABLE 10

Percent of Animals with Ulceration by Day with Mucositis Score ≥ 3.

| Group | Percent Ulceration by Day (Score ≥ 3) | | | | | | | | | | | |
|---|---|---|---|---|---|---|---|---|---|---|---|---|
| | 6 | 8 | 10 | 12 | 14 | 16 | 18 | 20 | 22 | 24 | 26 | 28 |
| Group 1: Placebo | 0.0 | 0.0 | 12.5 | 25.0 | 100.0 | 100.0 | 100.0 | 100.0 | 100.0 | 75.0 | 50.0 | 37.5 |
| Group 2: Neat Oltipraz | 0.0 | 0.0 | 0.0 z | 50.0 y | 100.0 | 100.0 | 100.0 | 100.0 | 100.0 | 50.0 z | 25.0 z | 25.0 z |
| Group 3: Formulated Oltipraz Composition | 0.0 | 0.0 | 0.0 z | 25.0 | 62.5 z | 75.0 z | 75.0 z | 75.0 z | 75.0 z | 37.5 z | 62.5 z | 37.5 y |

Example 4: Qualitative Visual Assessment of Oltipraz Compositions

As noted above, the stability of the oltipraz crystals in an aqueous suspension can be assessed in 3 ways. First, they can be assessed by DLS to determine whether there is an increase in the MHD. Second, the potency (and thus the stability) of the suspension can be can be determined by sampling the top of the suspension, making sure not to mix any precipitate back into the suspension. The concentration of drug in the suspension should not decrease by a predetermined amount in a given period, e.g., by more than a predetermined amount e.g., 1%, 2%, 5%, 10%, 15% or 20% in a period selected from 1 minute, 5 minutes, 15 minutes, 30 minutes, 45 minutes, 1 hour, 2 hours, 6 hours, 12 hours and 24 hours.

Figure 6:
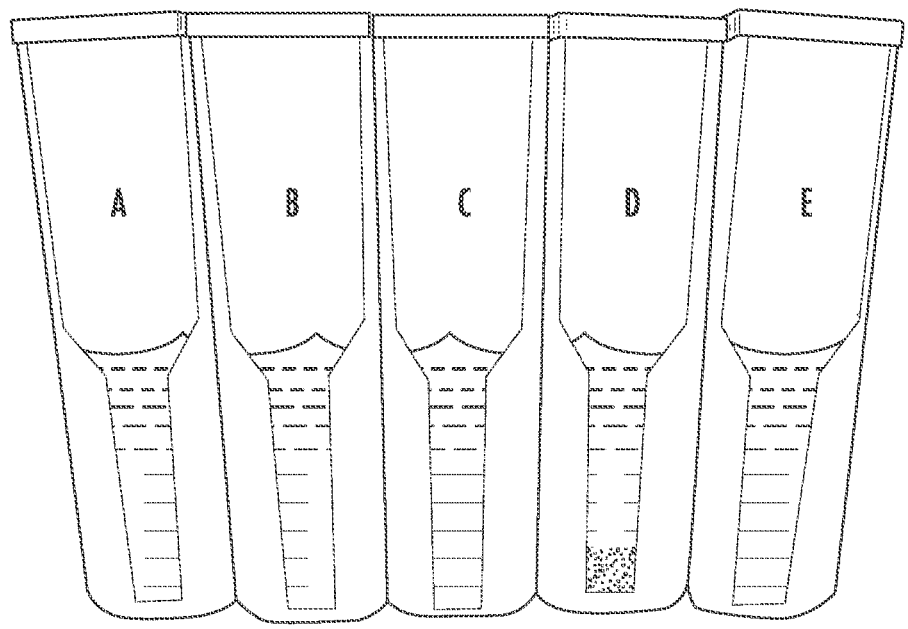
FIG. 6 is an illustration of the five aqueous suspensions described in Example 4 comprising formulated oltipraz compositions.

The third way is by a qualitative visual assessment. With a substantially stable suspension, after 24 hours of the suspension sitting un-agitated at ambient temperature (e.g., 25° C.), only a minimal amount of solids will form at the bottom of the container and the remaining suspension should not qualitatively change in either color or appearance. Suspensions that are not stable for predetermined periods will exhibit significant settling, a shift to more reddish color of the suspension, or a change in the opacity of the suspension. FIG. 6 illustrates a comparison of various suspensions prepared from spray dried compositions comprising oltipraz crystals prepared generally according to the method described in Example 1. The spray dried compositions were diluted in preparation for analysis by DLS and then allowed to stand without agitation. As can be seen, Sample D, which was prepared using Dextran 40 as the bulking agent, evidenced significant settling and an increase in the transparency of the suspension, indicating that this particular composition was not stable for a prolonged period. The compositions of the five samples is shown in Table 11 below:

TABLE 11

| Component | Sample A | Sample B | Sample C | Sample D | Sample E |
|---|---|---|---|---|---|
| ST-617 API | 14.8% | 14.8% | 14.8% | 14.8% | 14.8% |
| Eudragit RL | 7.5% | 7.5% | 7.5% | 7.5% | 7.5% |
| Tween 80 | 3.6% | 3.6% | 3.6% | 3.6% | 3.6% |
| PVP VA64 | 74.0% | | | | |
| Kollidon 30 | | 74.0% | | | |
| Geismar Trehalose | | | 74.0% | | |
| Dextran 40 | | | | 74.0% | |
| HPMC-E3 | | | | | 74.0% |

Example 5: Solubility Analysis of Oltipraz Compositions

The solubility of oltipraz crystals in a spray-dried composition prepared generally according to the method described in Example 1 was measured and compared against the solubility of neat crystalline oltipraz prepared according to the process disclosed in WO2016207914. The MHD of the oltipraz crystals in the spray-dried composition was 369.5 nm, with a polydispersity of 0.324 as measured by DLS after reconstituting the powder in water. The crystals in the neat crystalline oltipraz ranged in size from 20 µm to 200 µm. The solubility was determined at 20° C. both in water and in standard 2% simulated intestinal fluid (Fisher Scientific, USA. Catalog No. 7109-16). The results are reported in Table 12 below.

TABLE 12

| Sample Condition | Measured Solubility µg/mL (mean n = 2) |
|---|---|
| Neat oltipraz in water | 3.1 |
| Solubility of active ingredient (oltipraz crystals) in spray-dried composition in water | 5.7 |
| Neat oltipraz in 2% simulated intestinal fluid | 15.8 |
| Solubility of active ingredient (oltipraz crystals) in spray-dried composition in 2% simulated intestinal fluid | 22.6 |

As can be seen, the solubility of the oltipraz crystals in water almost doubled as compared to the neat oltipraz crystals, showing an increase of 83%. The increase in the simulated intestinal fluid was greater than 40%, i.e., approximately 43%.

Example 6: Lyophilization of Oltipraz Compositions

An 87.5 mg sample containing 50 mg of oltipraz crystals that were nano-milled to less than 300 nm particle size, 25 mg of Eudrogit and 12.5 mg of Tween80 was added to a 5 ml aqueous solution containing 495 mg of PVP-VA64. The sample was frozen with dry ice and subjected to standard lyophilization (freeze drying) on a Labconco lyophilizer at $10 \times 10(-4)$ mbar vacuum for 4 hours. The resultant powder was compared to powder that was formed by spray drying the same suspension and was found to have substantially the same bulk density and physical characteristics as the sample prepared in Example 1.

Example 7: MTT Cell Viability and Intracellular ROS Assays Using HGEPp Cells

Accumulation of reactive oxygen species (ROS) coupled with an increase in oxidative stress is implicated in the pathogenesis of many diseases. Free radicals and other reactive species are constantly generated in vivo and cause oxidative damage to biomolecules, a process held in check by multiple antioxidant and repair systems. Recrystallized oltipraz (prepared according to the process disclosed in WO2016207914) and a formulated oltipraz composition prepared generally according to the process described in Example 1 were tested to determine their effect on protecting primary human gingival epithelial cells (HGEPp) cells from oxidative damage induced by hydrogen peroxide (H2O2). Both treatments showed a statistically significant decrease in intracellular Reactive Oxygen Species concentrations in HGEPp cells at 95% confidence level. The formulated oltipraz composition showed a higher protective effect compared to the recrystallized oltipraz at an 80% confidence level. The data showed a numerical increase in the level of protective activity for the formulated oltipraz compositions as compared to the recrystallized oltipraz. The data did reveal a statistically significant decrease in intracellular ROS (P<0.2) for the formulated oltipraz composition as compared to the recrystallized oltipraz.

Objectives 1. measure the effect of recrystallized oltipraz, formulated oltipraz composition and control powder on cell proliferation within HGEPp cells treated with H2O2, using the TACS MTT Cell Viability Assay Kit
2. measure the effect of recrystallized oltipraz amd formulated oltipraz on hydroxyl, peroxyl and other reactive oxygen species within HGEPp cells, using Cell Biolabs' OxiSelect™ Intracellular ROS Assay Kit. This assay employs the cell-permeable fluorogenic probe 2',7'-dichlorodihydrofluorescein diacetate (DCFH-DA) which diffuses into cells and is deacetylated by cellular esterases to a nonfluorescent DCFH which is then rapidly oxidized to highly fluorescent 2',7'-dichlorodihydrofluorescein (DCF) by ROS.

Materials

Recrystallized oltipraz prepared by Supportive Therapeutics LLC (Appearance: Red Powder (98.6% HPLC purity)

Formulated oltipraz crystals (Supportive Therapeutics LLC), prepared as described above in Example 1. The MHD of the crystals, as measured by dynamic light scattering (DLS), was about 300 nm. (Appearance: Red Powder)

Control Powder (Supportive Therapeutics LLC) prepared as described above in Example 1, but with no oltipraz crystals (Appearance: Red Powder)

HGEPp cells were purchased from CellnTec Advanced Cell Systems AG

TACS MTT Cell Viability Kit was purchased from Trevigen Inc., USA

OxiSelect™ Intracellular ROS Assay Kit was purchased from Cell Biolabs Inc USA.

Methods

Cell Culture

Pooled primary HGEPps were propagated in CnT-Prime epithelial culture medium provided by CellnTec on 100 mm petri dishes coated with 30 mg/ml Type I rat tail collagen (BD Biosciences) diluted in Dulbecco's phosphate-buffered saline (DPBS). This cell type was chosen since the formulated oltipraz compositions described herein have the potential to serve as a treatment for oral mucositis in a suspension formulation, thereby putting such compositions in close contact with HGEPp cells. The cells were harvested when they reached 70-90% confluency as observed by light microscopy. For routine cultivation, the medium was changed every 3 days. For both the cell viability and ROS assays, the cells from passages 3-7 were seeded at 5×0 3, 2.5×10 4, 5×0 4 cells/cm 2 density to grow cell monolayers in 24-well flat-bottomed tissue culture plates and acclimated overnight at 37° C.

Preparation of Dosing Solutions
1. Recrystallized oltipraz was received as a powder from Supportive Therapeutics and a 100 mM DMSO stock was prepared. Further dilutions were prepared in DMSO from the 100 mM DMSO stock and each DMSO dilution was then added into 10 mL of Dulbecco's phosphate-buffered saline to arrive at final concentrations of 10, 50, and 100 µM.
2. The Normal (Control) group contained saline with the same percentage of DMSO as the treated group.
3. All dosing solutions contained 0.3% of DMSO which is well below the maximum tolerated DMSO percent of 0.8% for HGEPp cells.
4. Formulated oltipraz crystals and control powder were received as a powder and a 500 mM DMSO stock solution was prepared for each powder.
5. 5× dilutions were prepared in DMSO from the 500 mM DMSO stock and each DMSO dilution was then added into 10 mL of Dulbecco's phosphate-buffered saline to arrive at final concentrations of 10, 50, and 100 µM of formulated oltipraz composition and control powder.

Cell Survival Assay (TACS MTT Kit)
1. Plate cell concentration was selected to be 6.25×10 5/ml to yield an OD absorbance within the linear portion of the control curve.
2. Once the HGEPp cells were cultured and ready on the microplate, the media was removed from all the wells and discarded. The cells were washed gently with DPBS 2-3 times and the last wash removed and discarded.
3. Added 10 ul of MT reagent to each well.
4. Incubated the plate for 6 hours at 37° C. Viewed the cells to confirm the appearance of intracellular precipitate using an inverted microscope.
5. Added 100 ul of Detergent Reagent to all wells, including the control wells taking care not to shake the plates
6. Left the plate covered in the dark at room temperature overnight.
7. Removed the plate cover and measured the absorbance of the wells, including the blanks at 570 nm.
8. Determined the average values from triplicate readings after subtracting the average value for the blanks.

Oxidative Stress Measurement ROS Assay (OxiSelect Kit)
1. Prepared and mixed all reagents thoroughly before use. (Kit instruction)
2. Once the HGEPp cells were cultured and ready on a microplate, the media was removed from all the wells and discarded. Washed the cells gently with DPBS 2-3 times. Removed the last wash and discarded it.
3. Added 100 µL of 1×DCFH-DA/media solution to the cells. Incubated at 37° C. for 60 minutes. Removed and discarded the solution.
4. Treated the DCFH-DA loaded cells with recrystallized oltipraz, formulated oltipraz composition and control powder at the targeted concentrations and with saline/DMSO control.
5. Fluorescence was read on a Fluorescence Plate Reader after 1 hour. All treatment media was carefully removed from the wells and discard. The cells were washed 3 times gently with DPBS. Added 100 µL of medium to each well. Added 100 µL of the 2× Cell Lysis Buffer, mixed thoroughly and incubated for 5 minutes. Transferred 150 µL of the mixture to a fresh 24-well plate for fluorescence measurements at 530 nm.

Results

H2O2-Induced Cytotoxicity in a Dose-Dependent Manner

Figure 7:
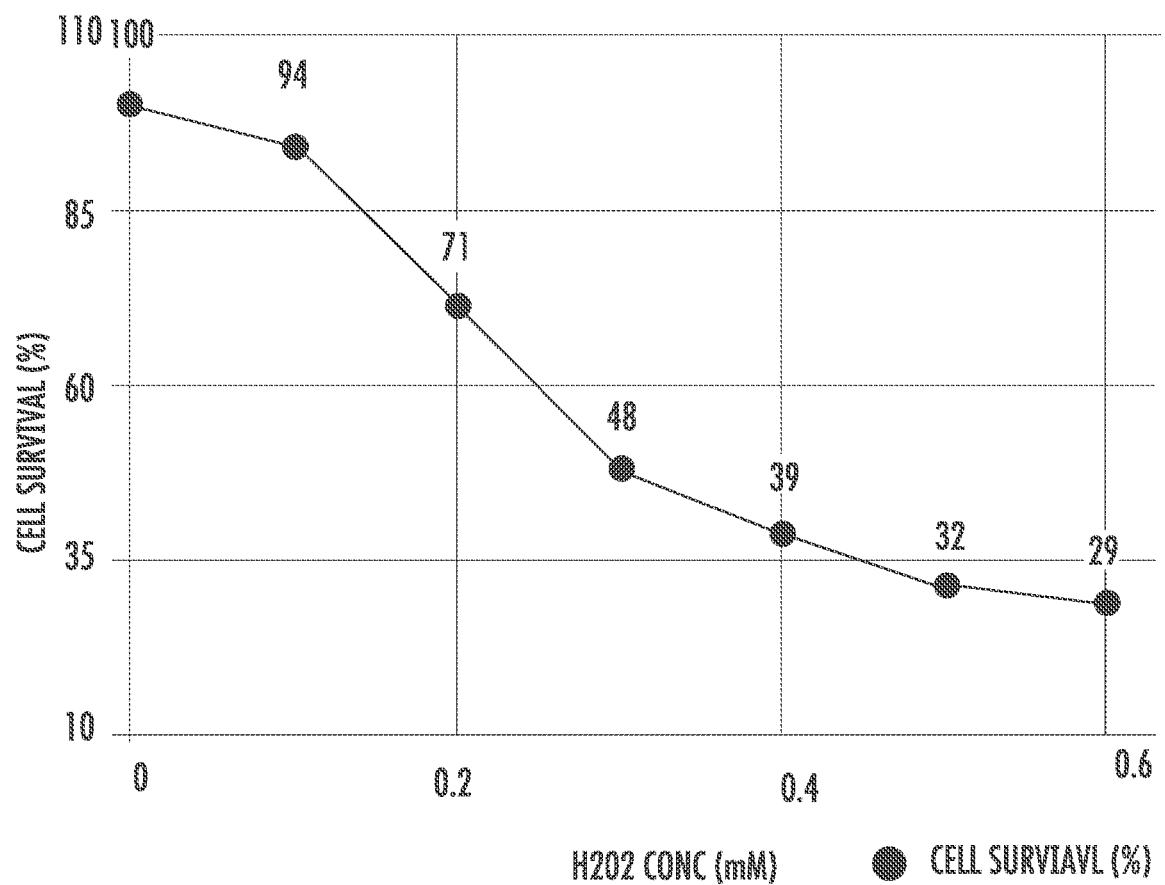
FIG. 7 is a graph showing the effect of hydrogen peroxide (H2O2) on the viability of primary human gingival epithelial cells (HGEPp).

HGEPp cells were exposed to different concentrations of H2O2 for 4 h to examine H2O2-induced oxidative stress. The cells were exposed to 0-0.6 mM H2O2 for 4 h and cell viability was evaluated using the TACS MTT Cell Proliferation Assay Kit. The percentage of cell survival was determined using the ratio of the optical density (OD) of the test sample to the OD of the control×100%. The results showed that H2O2 exposure led to oxidative stress in a concentration-dependent manner. There was 48% reduction in cell number when the cells were treated with 0.3 mM H2O2 (FIG. 7). Therefore, this concentration was taken to be IC50 of H2O2 in HGEPp cells and used in the follow-on experiments. The data is mean+/−SD of 3 experiments in 6 replicate wells.

Effect on H2O2-Induced Oxidative Stress in HGEPp

Figure 8:
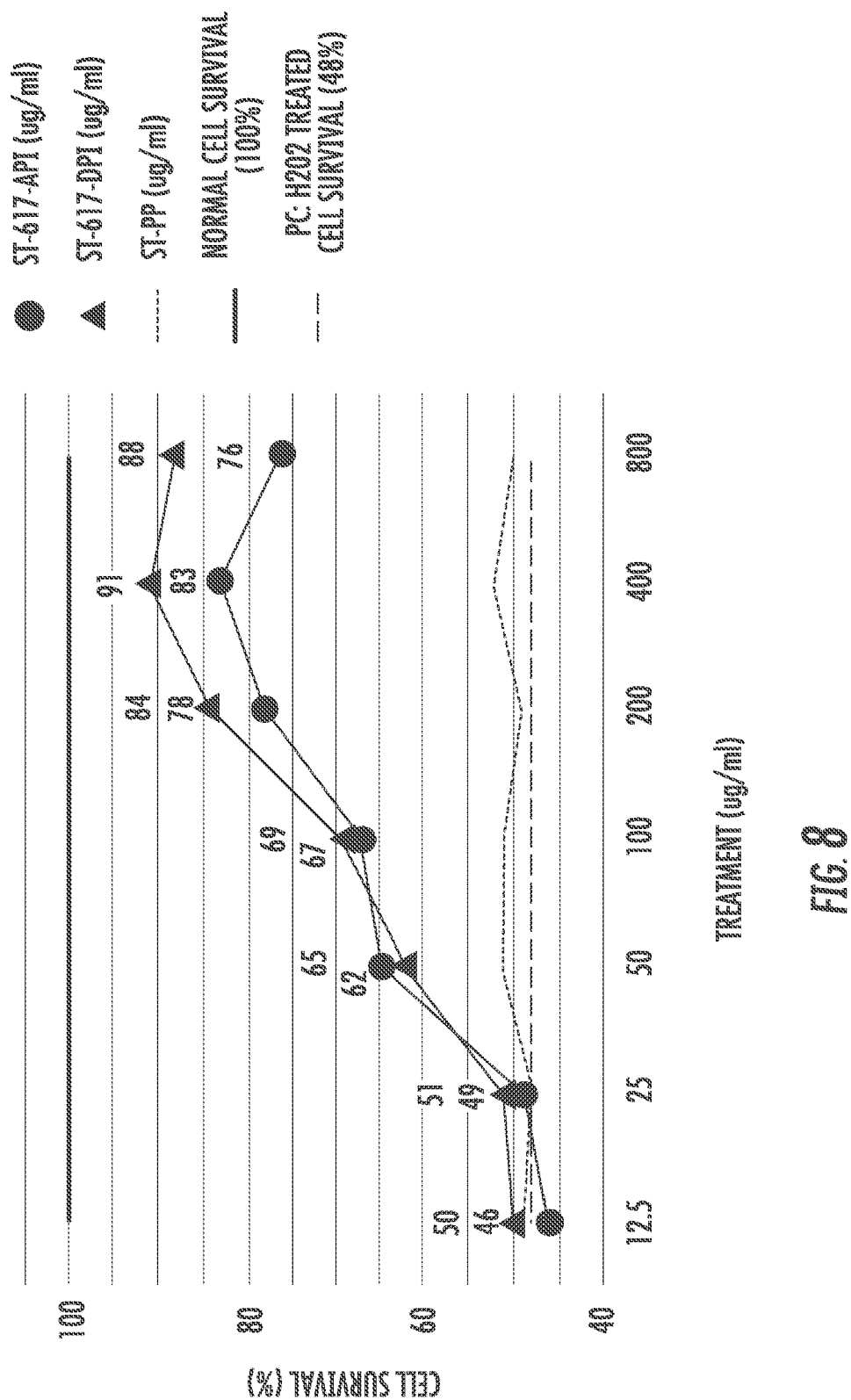
FIG. 8 is a graph showing the effect of recrystallized oltipraz, formulated oltipraz composition as described herein, and a control powder on H2O2-induced oxidative stress in HGEPp cells.

Incubation of HGEPp with H2O2 decreased cell viability significantly (FIG. 7). This viability was modulated by the recrystallized oltipraz and the formulated oltipraz composition, but not by the control powder (FIG. 8). The results indicate that recrystallized oltipraz and formulated oltipraz composition at the concentrations in the range from 50 to 800 □g/ml promoted cell proliferation and reduced H2O2-induced decrease in HGEPp survival.

Normal control cells were cultured in DPBS containing 0.3% DMSO. Positive Control (PC): oxidative stressed group cells after treatment with 0.3 mM H2O2 for 4 h. The remaining groups of cells were pretreated for 24 h with recrystallized oltipraz, formulated oltipraz composition, and the control powder at 12.5, 25, 50, 100, 200, 400, 800 µg/mL) prior to treatment with H2O2. The percentage of cell survival was determined by the ratio of the optical density (OD) of the test samples to the OD of the control×100%. The data are presented as the means+/−SD of measurements that were performed in triplicate in six replicate wells, *P<0.05 for recrystallized oltipraz and formulated oltipraz compositions between 50-800 ug/ml versus the PC. The data shows a numerical increase in the level of protective activity for the formulated oltipraz composition as compared to the recrystallized oltipraz.

Effect on ROS Production in HGEPp Cells

Figure 9:
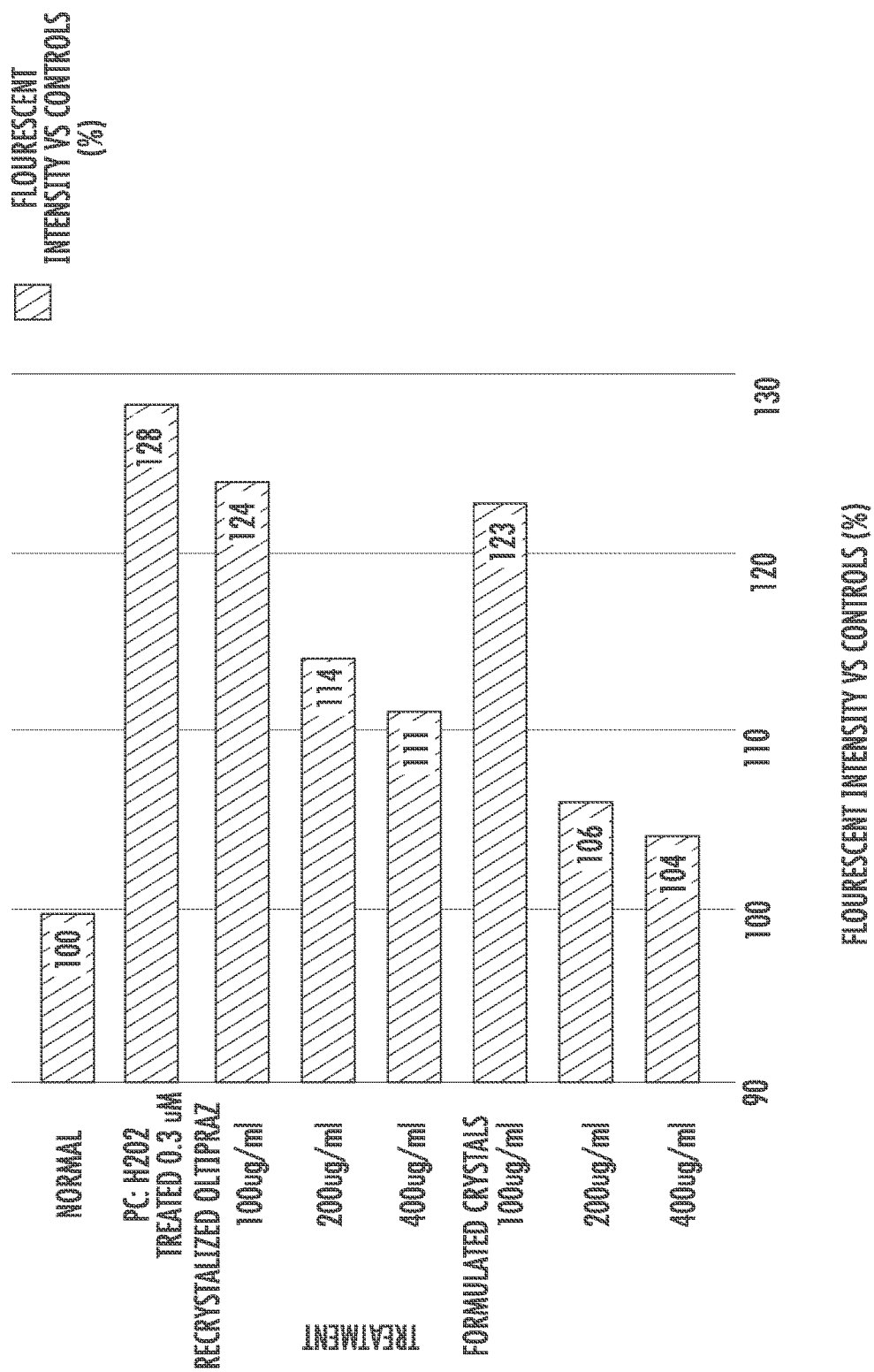
FIG. 9 is a graph showing the effect of recrystallized oltipraz and formulated oltipraz composition as described herein on the production of reactive oxygen species (ROS) in HGEPp cells.

The formation of reactive oxygen species (ROS) is indicative of oxidative stress. There were significantly higher ROS levels (128%) in H2O2-treated hGEP cells compared to normal control cells (100%). The results indicate that recrystallized oltipraz and the formulated oltipraz composition at 100 ug/ml and 200 ug/ml significantly reduced ROS levels in H2O2 treated HGEPp cells. (FIG. 9)

Normal: Normal control cells were cultured in DPBS containing 0.3% DMSO. Positive Control (PC): oxidative stressed group cells after treatment with 0.3 mM 11202 for 4 h. The remaining groups of cells were pretreated for 24 h with recrystallized oltipraz and formulated oltipraz composition, respectively, at 50, 100, 200 µg/mL prior to treatment with H2O2.

Intracellular ROS was measured using a Spectramax M3 microplate reader. The data are presented as the means+/− SD of measurements that were performed in triplicate in six replicate wells, *P<0.05 for recrystallized oltipraz and formulated oltipraz composition at 100 and 200 ug/ml versus the PC. The data also shows a statistically significant (80%) decrease in intracellular ROS (P<0.2) for the formulated oltipraz composition as compared to the recrystallized oltipraz. That is, the data shows a statistically significant (80% confidence level) superiority for the formulated oltipraz composition as compared to the recrystallized oltipraz.

The pharmaceutical compositions and methods of administering the pharmaceutical compositions of this disclosure thus may be used to treat any human or non-human animal patient to decrease intracellular reactive oxygen species (ROS) and/or decrease oxidative stress, including in patients undergoing treatments that provide oxidative stress such as chemotherapy or radiation therapy. The pharmaceutical compositions and methods of administering the pharmaceutical compositions of this disclosure may be used to treat any human or non-human animal patient to provide an antioxidant effect, including in patients undergoing treatments that provide oxidative stress such as chemotherapy or radiation therapy. The pharmaceutical compositions and methods of administering the pharmaceutical compositions of this disclosure also may be used to slow the onset, and/or reduce the severity, and/or reduce the duration of oxidative damage in patients (e.g., mucositis, including oral mucositis), including in patients undergoing treatments that provide oxidative damage such as chemotherapy or radiation therapy.

Example 8: Relative Expression of Stress Genes

The Nrf2 system is considered to be a major cellular defense mechanism against oxidative damage by activating genes that encode phase II detoxifying and antioxidant enzymes. The Human oxidative stress PCR array was used to evaluate the relative expression of 84 stress genes after pretreating with 100 uM of recrystallized oltipraz (prepared according to the process disclosed in WO2016207914), formulated oltipraz composition prepared generally in accordance with the process described in Example 1 (MHD less than about 350 nm) and negative control (formulated oltipraz composition without the oltipraz) within HGEPp cells. Total RNA was isolated from treated HGEPp cells, purified and reverse transcription was used to generate cDNA. This was combined with the Qiagen RT2 SYBR Green ROX 96-well array kit and after thermal cycling (BioRad), the gene expressions were recorded (MyiQ detection system) and converted to Fold Change using the Qiagen on-line data analysis tool.

The negative control showed no change in any gene regulation. The recrystallized oltipraz and formulated oltipraz composition both showed up-regulation at Fold Change >2 for ALOX12, GPX1, GCLC, GCLM, NQO1, SOD1 and GAPDH genes and down-regulation at Fold Change >2 for GTF2I, PTGS1 and UCP2 genes.

Only the formulated oltipraz composition additionally showed up-regulation of GPX4 (glutathione peroxidase 4—which is specific to cell membrane antioxidant activity) and MPO (myeloperoxidase) and down-regulation of PRDX2 (Peroxiredoxin 2) at a Fold Change >2.

The pharmaceutical compositions and methods of administering the pharmaceutical compositions of this disclosure thus may be used to treat any human or non-human animal patient to increase the gene expression of GPX4 and/or MPO. The pharmaceutical compositions and methods of administering the pharmaceutical compositions of this disclosure thus also may be used to treat any human or non-human animal patient to decrease the gene expression of PRDX2. The pharmaceutical compositions and methods of administering the pharmaceutical compositions of this disclosure thus also may be used to treat any human or non-human animal patient to increase the gene expression of GPX4 and/or MPO and decrease the gene expression of PRDX2.

Example 9: Oltipraz Composition with Taste-Improving Additives

Table 13 provides an example of an embodiment of a liquid oltipraz composition comprising a dry oltipraz composition similar to that described in Example 1 in combination with water and additives to improve the palatability of the liquid composition. The total volume of the composition is 10 mL:

TABLE 13

| Ingredient | Amount in 10 mL |
| --- | --- |
| Sucralose | 8 mg |
| Forest Fruit M60056 from Mane Inc. (density = 1.043 g/mL) | 0.024 mL |
| Mint M30862 from Mane Inc. (density = 0.900 g/mL) | 0.0001 mL |
| Physcool ® Synergy M0059829 from Mane Inc. (density = 1.032 g/mL) | 0.0025 mL |
| Potassium sorbate | 5 mg |
| Dry composition comprising oltipraz (50 g) and ~1% magnesium stearate (lubricant) | 300 mg |

The composition had an initial mint taste which was succeeded by a berry favor and then succeeded by a cooling sensation. The bitter taste of oltipraz was successfully masked.

Recitation of Embodiments

1. A composition comprising a quantity of crystals, wherein the quantity substantially comprises crystals of 4-methyl-5-(pyrazin-2-yl)-3H-1,2-dithiole-3-thione having an intensity averaged, mean hydrodynamic diameter (Z-average) ("MHD") of from 30 to 2000 nm,
   wherein the MHD is determined performing dynamic light scattering at 25° C. on a suspension of the crystals in water at a concentration of 0.01 to 0.1 mg of crystals per mL of water.
2. A composition according to embodiment 1, wherein the quantity substantially comprises crystals that have a MHD in the range of from 30 to 100 nm.
3. A composition according to embodiment 1, wherein the quantity substantially comprises crystals that have a MHD in the range of from 100 to 1200 nm.
4. A composition according to embodiment 1, wherein the quantity substantially comprises crystals that have a MHD in the range of from 150 to 600 nm.
5. A composition according to embodiment 1, wherein the quantity substantially comprises crystals that have a MHD in the range of from 150 to 450 nm.
6. A composition according to embodiment 2, wherein the composition comprises at least one stabilizing agent, and wherein the quantity substantially comprises crystals that will have a MHD in the range of from 30 to 100 nm if left in water at 25° C. for 1 hour.
7. A composition according to embodiment 2, wherein the composition comprises at least one stabilizing agent, and wherein the quantity substantially comprises crystals that will have a MHD in the range of from 30 to 100 nm if left in water at 25° C. for 1 hour.
8. A composition according to embodiment 3, wherein the composition comprises at least one stabilizing agent, and wherein the quantity substantially comprises crystals that will have a MHD in the range of from 100 to 1200 nm if left in water at 25° C. for 1 hour.
9. A composition according to embodiment 3, wherein the composition comprises at least one stabilizing agent, and wherein the quantity substantially comprises crystals that will have a MHD in the range of from 100 to 1200 nm if left in water at 25° C. for 24 hours.
10. A composition according to embodiment 4, wherein the composition comprises at least one stabilizing agent, and wherein the quantity substantially comprises crystals that will have a MHD in the range of from 150 to 600 nm if left in water at 25° C. for 1 hour.
11. A composition according to embodiment 4, wherein the composition comprises at least one stabilizing agent, and wherein the quantity substantially comprises crystals that will have a MHD in the range of from 150 to 600 nm if left in water at 25° C. for 24 hours.
12. A composition according to embodiment 5, wherein the composition comprises at least one stabilizing agent, and wherein the quantity substantially comprises crystals that will have a MHD in the range of from 150 to 450 nm if left in water at 25° C. for 1 hour.
13. A composition according to any of embodiments 1-12, wherein the composition comprises less than 1 percent of drug-degradent impurities relative to 4-methyl-5-(pyrazin-2-yl)-3H-1,2-dithiole-3-thione in the aqueous composition and less than 2 percent total impurities relative to the 4-methyl-5-(pyrazin-2-yl)-3H-1,2-dithiole-3-thione in the aqueous suspension.
14. A composition according to any of embodiments 1-12, wherein the composition comprises less than 0.1 percent of drug-degradent impurities relative to 4-methyl-5-(pyrazin-2-yl)-3H-1,2-dithiole-3-thione in the aqueous composition and less than 0.5 percent total impurities relative to the 4-methyl-5-(pyrazin-2-yl)-3H-1,2-dithiole-3-thione in the aqueous suspension.
15. A composition according to any of embodiments 1-14, wherein the polydispersity index (PdI) of the crystals in the quantity is less than 0.80, wherein $PdI=(\sigma/d)^2$, wherein $\sigma$ is the standard deviation and d is the mean hydrodynamic diameter (Z-average).
16. A composition comprising a quantity of crystals according to embodiment 15, wherein the polydispersity index (PdI) of the crystals in the quantity is less than 0.60.
17. A composition comprising a quantity of crystals according to embodiment 15, wherein the polydispersity index (PdI) of the crystals in the quantity is between 0.10 and 0.60.
18. A composition comprising a quantity of crystals according to embodiment 15, wherein the polydispersity index (PdI) of the crystals in the quantity is between 0.10 and 0.45.
19. An composition according to any of embodiments 1-18, wherein the quantity of crystals comprises substantially the entire quantity of 4-methyl-5-(pyrazin-2-yl)-3H-1,2-dithiole-3-thione present in the composition.
20. A composition according to any of embodiments 5-19, wherein the at least one stabilizing agent comprises a polymer.
21. A composition according to embodiment 20, wherein the polymer is a cationic or anionic polymer.
22. A composition according to embodiment 21, wherein the polymer is a cationic polymer.
23. A composition according to embodiment 22, wherein the cationic polymer comprises ammonium functionality.
24. A composition according to embodiment 22, wherein the cationic polymer comprises quaternary ammonium functionality.
25. A composition according to any of embodiments 21-24, wherein the cationic polymer is a polymer that is formed from polymerization of compounds comprising at least one acrylate-containing compound.
26. A composition according to any of embodiments 21-25, wherein the cationic polymer comprises Poly(ethyl acrylate-co-methyl methacrylate-co-trimethylammonioethyl methacrylate chloride) 1:2:0.2 (Eudragit RL).
27. A composition according to any of embodiments 1-19, wherein the at least one stabilizing agent comprises a surfactant.
28. A composition according to any of embodiments 20-26, wherein the composition comprises a surfactant.
29. A composition according to embodiment 27 or 28, wherein the surfactant is a nonionic surfactant.
30. A composition according to embodiment 27-29, wherein the surfactant is a sorbitan ester.
31. A composition according to any of embodiments 27-30, wherein the surfactant is polyethylene glycol sorbitan monooleate.
32. A composition according to embodiment 27 or 28, wherein the surfactant is selected from the group consisting of polyethylene glycol sorbitan monooleate surfactants, polyethylene glycol hydrogenated castor oil, block copolymers of poly(ethylene oxide) and poly(propylene oxide), sodium lauryl sulfate, benzalkonium chloride, and sodium docusate.

33. A composition according to any of embodiments 1-19, wherein the composition comprises a bulking agent.
34. A composition according to any of embodiments 20-26, wherein the composition comprises a bulking agent.
35. A composition according to embodiment 27, wherein the composition comprises a bulking agent.
36. A composition according to any of embodiments 28-32, wherein the composition comprises a bulking agent.
37. A composition according to any of embodiments 5-19, wherein the at least one stabilizing agent comprises a bulking agent.
38. A composition according to any of embodiments 33-37, wherein the bulking agent comprises a polyvinylpyrrolidone compound.
39. A composition according to embodiment 38, wherein the bulking agent comprises a copolymer of polyvinylpyrrolidone and poly(vinyl acetate) with a ratio of approximately 6:4 of vinylpyrrolidone and vinyl acetate monomers (PVP-VA64).
40. A composition according to any of embodiments 1-19, wherein the composition comprises water.
41. A composition according to any of embodiments 1-19, wherein the composition comprises a non-aqueous solvent.
42. A composition according to embodiment 40 or 41, wherein the quantity of crystals comprise from 4 to 15 percent by weight of the composition.
43. A composition according to embodiment 40 or 41, wherein the quantity of crystals comprise from 6 to 12 percent by weight of the composition.
44. A composition according to embodiments 20-26, wherein the composition comprises water.
45. A composition according to any of embodiments 20-26, wherein the composition comprises a non-aqueous solvent.
46. A composition according to embodiment 44 or 45, wherein the quantity of crystals comprise from 4 to 15 percent by weight of the composition and the polymer comprises from 7.5 percent to 25 percent by weight of the composition.
47. A composition according to any of embodiments 27-32, wherein the composition comprises water.
48. A composition according to any of embodiments 27-32, wherein the composition comprises a non-aqueous solvent.
49. A composition according to embodiment 47 or 48, wherein the quantity of crystals comprise from 4 to 15 percent by weight of the composition and the surfactant comprises less than 5 percent by weight of the composition.
50. A composition according to any of embodiments 28-32, wherein the composition further comprises water.
51. A composition according to any of embodiments 28-32, wherein the composition comprises a non-aqueous solvent.
52. A composition according to embodiment 50 or 51, wherein the quantity of crystals comprise from 4 to 15 percent by weight of the composition, the polymer comprises from 2 to 10 percent by weight of the composition, and the surfactant comprises less than 5 percent by weight of the composition.
53. A composition according to any of embodiments 33-39, wherein the composition comprises water.
54. A composition according to any of embodiments 33-39, wherein the composition comprises a non-aqueous solvent.
55. A composition according to embodiment 53 or 54, wherein the quantity of crystals comprise from 1 to 10 percent by weight of the composition and the bulking agent comprises from 10 to 30 percent by weight of the composition.
56. A composition according to any of embodiments 34-39, wherein the composition comprises water.
57. A composition according to any of embodiments 34-39, wherein the composition comprises a non-aqueous solvent.
58. A composition according to embodiment 56 or 57, wherein the quantity of crystals comprise from 1 to 10 percent by weight of the composition, the polymer comprises less than 5 percent by weight of the composition, and the bulking agent comprises from 10 to 30 percent by weight of the composition.
59. A composition according to any of embodiments 35-39, wherein the composition comprises water.
60. A composition according to any of embodiments 35-39, wherein the composition comprises a non-aqueous solvent.
61. A composition according to embodiment 60 or 61, wherein the quantity of crystals comprise from 1 to 10 percent by weight of the composition, the surfactant comprises less than 4 percent by weight of the composition, and the bulking agent comprises from 10 to 30 percent by weight of the composition.
62. A composition according to any of embodiments 36-39, wherein the composition comprises water.
63. A composition according to any of embodiments 36-39, wherein the composition comprises a non-aqueous solvent.
64. A composition according to embodiment 61, wherein the quantity of crystals comprise from 1 to 10 percent by weight of the composition, the polymer comprises less than 5 percent by weight of the composition, the surfactant comprises less than 4 percent by weight of the composition, and the bulking agent comprises from 10 to 30 percent by weight of the composition.
65. A composition according to any of embodiments 33-39, wherein the composition substantially excludes water and any non-aqueous solvent.
66. A composition according to embodiment 65, wherein the bulking agent comprises from 50 to 90 percent by weight of the composition.
67. A composition according to embodiment 65, wherein the bulking agent comprises from 60 to 85 percent by weight of the composition.
68. A composition according to any of embodiments 34-39, wherein the composition substantially excludes water and any non-aqueous solvent.
69. A composition according to embodiment 68, wherein the bulking agent comprises from 50 to 90 percent by weight of the composition, and the polymer comprises from 3 to 12 percent by weight of the composition.
70. A composition according to any of embodiments 35-39, wherein the composition substantially excludes water and any non-aqueous solvent.
71. A composition according to embodiment 70, wherein the bulking agent comprises from 50 to 90 percent by weight of the composition, and the surfactant comprises from 1 to 8 percent by weight of the composition.
72. A composition according to embodiment 70, wherein the bulking agent comprises from 60 to 85 percent by weight of the composition, and the surfactant comprises from 1 to 6 percent by weight of the composition.
73. A composition according to any of embodiments 36-39, wherein the composition substantially excludes water and any non-aqueous solvent.
74. A composition according to embodiment 73, wherein the bulking agent comprises from 50 to 90 percent by weight of the composition, the polymer comprises from 3 to 12 percent by weight of the composition, and the surfactant comprises from 1 to 8 percent by weight of the composition.
75. A composition according to embodiment 73, wherein the bulking agent comprises from 60 to 85 percent by weight of the composition, the polymer comprises from 5 to 10 percent by weight of the composition, and the surfactant comprises from 1 to 6 percent by weight of the composition.
76. A composition according to any of embodiments 64-75, wherein the quantity of crystals comprises from 5 to 25 percent by weight of the composition.
77. A composition according to any of embodiments 64-75, wherein the quantity of crystals comprises from 10 to 20 percent by weight of the composition.
78. A composition according to any of embodiments 64-75, wherein the quantity of crystals comprises from 12 to 17 percent by weight of the composition.
79. A composition according to any of embodiments 64-75, wherein the composition substantially excludes water, and wherein the composition is capable of forming a substantially complete aqueous suspension of a quantity of crystals.
80. A composition according to embodiment 79, wherein the composition will form a substantially complete aqueous suspension with vigorous shaking in less than 15 minutes if mixed with water at a weight:weight ratio of 1 part of the dry composition per 10 parts of water at 25° C.
81. A composition according to embodiment 79, wherein the composition will form a substantially complete aqueous suspension with vigorous shaking in less than 10 minutes if mixed with water at a weight:weight ratio of 1 part of the dry composition per 10 parts of water at 25° C.
82. A composition according to embodiment 79, wherein the composition will form a substantially complete aqueous suspension with vigorous shaking in less than 5 minutes if mixed with water at a weight:weight ratio of 1 part of the dry composition per 10 parts of water at 25° C.
83. A composition according to embodiment 79, wherein the composition will form a substantially complete aqueous suspension with vigorous shaking in less than 2 minutes if mixed with water at a weight:weight ratio of 1 part of the dry composition per 10 parts of water at 25° C.
84. A composition according to any of embodiment 79, wherein the composition will form a substantially complete aqueous suspension with vigorous shaking in less than 1 minute if mixed with water at a weight:weight ratio of 1 part of the dry composition per 10 parts of water at 25° C.
85. A composition according to any of embodiments 64-84 that substantially excludes water, wherein the composition has been made by a process comprising spray drying.
86. A composition that substantially excludes water made by a process comprising spray drying an aqueous formulation comprising water and a composition according to any of embodiments 1-63.
87. A composition according to any of embodiments 64-84 that substantially excludes water, wherein the composition has been made by a process comprising lyophilization.
88. A composition that substantially excludes water made by a process comprising lyophilizing an aqueous formulation comprising water and a composition according to any of embodiments 1-63.
89. A dry pharmaceutical composition comprising a composition according to any of embodiments 1-39 and 64-88 that substantially excludes water and any non-aqueous solvent.
90. A dry pharmaceutical composition according to embodiment 89, comprising at least one pharmaceutically acceptable additive.
91. A dry pharmaceutical composition according to embodiment 89 or 90, comprising a pharmaceutically acceptable additive that inhibits microbial growth.
92. A dry pharmaceutical composition according to any of embodiments 89-91, comprising a pharmaceutically acceptable lubricant.
93. A dry pharmaceutical composition according to embodiment 92, wherein the lubricant is magnesium stearate or silica oxide.
94. A dry pharmaceutical composition according to embodiment 92 or 93, wherein the lubricant is present in an amount of up to 2 percent by weight of the pharmaceutical composition.
95. A dry pharmaceutical composition comprising up to 2000 mg of a dry pharmaceutical composition according to any of embodiments 89-94.
96. A dry pharmaceutical composition comprising up to 1000 mg of a dry pharmaceutical composition according to any of embodiments 89-94.
97. A dry pharmaceutical composition comprising up to 500 mg of a dry pharmaceutical composition according to any of embodiments 89-94.
98. A pharmaceutical composition suitable for oral administration comprising a liquid and a composition according to any of embodiments 1-63.
99. A pharmaceutical composition suitable for oral administration comprising a non-aqueous liquid and a composition according to any of embodiments 1-63.
100. An aqueous pharmaceutical composition suitable for oral administration comprising water and a composition according to any of embodiments 1-63.
101. An aqueous pharmaceutical composition prepared by a process comprising the step of mixing a combination of ingredients comprising a liquid and a dry pharmaceutical composition according to any of embodiments 89-97.
102. A pharmaceutical composition according to 101, wherein the mixture comprises, in a weight:weight ratio, 1 part of dry pharmaceutical composition and up to 100 parts of liquid.
103. A pharmaceutical composition according to 101, wherein the mixture comprises, in a weight:weight ratio, 1 part of dry pharmaceutical composition and up to 60 parts of liquid.
104. A pharmaceutical composition according to 101, wherein the mixture comprises, in a weight:weight ratio, 1 part of dry pharmaceutical composition and up to 40 parts of liquid.
105. A pharmaceutical composition according to 101, wherein the mixture comprises, in a weight:weight ratio, 1 part of dry pharmaceutical composition and up to 20 parts of water.

106. A pharmaceutical composition according to any of embodiments 101-105, comprising at least one pharmaceutically acceptable taste-modifying additive.

107. A pharmaceutical composition according to any of embodiments 101-106, wherein the liquid comprises water.

108. A pharmaceutical composition according to any of embodiments 101-107, wherein the liquid comprises a non-aqueous solvent.

109. A pharmaceutical composition for topical administration to skin comprising a composition according to any of embodiments 1-78 and a pharmaceutically acceptable ingredient for topical administration.

110. A pharmaceutical composition for rectal administration comprising a composition according to any of embodiments 1-78 and a pharmaceutically acceptable ingredient for rectal administration.

111. A pharmaceutical composition for colonic administration comprising a composition according to any of embodiments 1-78 and a pharmaceutically acceptable ingredient for colonic administration.

112. A pharmaceutical composition for administration by inhalation comprising a composition according to any of embodiments 1-39 and 64-99.

113. A medical device comprising an inhaler and a pharmaceutical composition for administration by inhalation according to embodiment 112.

114. A process for making a medical device according to embodiment 113 comprising loading a dose of a pharmaceutical composition according to embodiment 112 into an inhaler.

115. A pharmaceutical dose for oral administration comprising a composition according to any of embodiments 1-39 and 64-99.

116. A pharmaceutical composition according to embodiment 115, wherein the dose is in the form of a pills, tablet or capsule that substantially excludes water.

117. A pharmaceutical composition according to embodiment 115, wherein the dose is in the form of a liquid.

118. A pharmaceutical composition according to embodiment 117, wherein the dose is in a soft gel capsule.

119. A pharmaceutically acceptable container for providing an aqueous pharmaceutical composition, comprising a cavity of sufficient size to hold both a dry pharmaceutical composition and a quantity of liquid comprising an amount of water sufficient to permit mixing of the dry pharmaceutical composition to form a liquid composition, wherein the dry pharmaceutical composition comprises a composition according to any of embodiments 1-39 and 64-97 that substantially excludes water and any non-aqueous solvents.

120. A pharmaceutically acceptable container according to embodiment 119, further comprising a releasable coupling for providing an opening in the container adapted to dispense a liquid composition from the container.

121. A pharmaceutically acceptable container according to embodiment 119, comprising a compartment separate from the cavity, said compartment comprising the dose of the dry pharmaceutical composition.

122. A pharmaceutically acceptable container according to embodiment 120, comprising a compartment separate from the cavity, said compartment comprising the dose of the dry pharmaceutical composition.

123. A pharmaceutically acceptable container according to embodiment 122, wherein the releasable coupling connects the portion of the container comprising the cavity to the portion of the container comprising the compartment.

124. A pharmaceutically acceptable container according to any of embodiments 120-123, further comprising a breakable seal between the compartment and the cavity.

125. A pharmaceutically acceptable container according to any of embodiments 119-124, further comprising a liquid comprising water.

126. A pharmaceutically acceptable container according to any of embodiments 119-125, further comprising a liquid comprising a non-aqueous solvent.

127. A pharmaceutically acceptable container according to embodiment 125 or 126, wherein the liquid also comprises at least one pharmaceutically acceptable taste-modifying additive.

128. A process comprising the step of wet milling a composition comprising a liquid and 4-methyl-5-(pyrazin-2-yl)-3H-1,2-dithiole-3-thione to form a liquid composition comprising crystals of 4-methyl-5-(pyrazin-2-yl)-3H-1,2-dithiole-3-thione, wherein wet milling yields a quantity of crystals that have an intensity averaged, mean hydrodynamic diameter (Z-average) ("MHD") of from 100 to 2000, wherein the MHD is determined by dynamic light scattering at 25° C., and a concentration of 0.01 to 0.1 mg of crystals per mL of water.

129. A process according to embodiment 128, wherein wet milling yields a quantity of crystals that have a MHD of from 100 to 1200 nm.

130. A process according to embodiment 128, wherein wet milling yields a quantity of crystals that have a MHD of from 150 to 600 nm.

131. A process according to embodiment 128, wherein wet milling yields a quantity of crystals that have a MHD of from 150 to 450 nm.

132. A process according to embodiments 128, wherein the composition comprises at least one stabilizing agent, and wherein the quantity of crystals will have a MHD of from 100 to 2000 nm if left in water at 25° C. for at least 1 hour.

133. A process according to embodiments 132, wherein the quantity of crystals will have a MHD in the range of from 100 to 2000 nm if left in water at 25° C. for 24 hours.

134. A process according to embodiments 129, wherein the composition comprises at least one stabilizing agent, and wherein the quantity of crystals will have a MHD of from 100 to 1200 nm if left in water at 25° C. for at least 1 hour.

135. A process according to embodiments 134, wherein the quantity of crystals will have a MHD of from 100 to 1200 nm if left in water at 25° C. for 24 hours.

136. A process according to embodiments 130, wherein the composition comprises at least one stabilizing agent, and wherein the quantity of crystals will have a MHD of from 150 to 600 nm if left in water at 25° C. for at least 1 hour.

137. A process according to embodiments 136, wherein the quantity of crystals will have a MHD of from 150 to 600 nm if left in water at 25° C. for 24 hours.

138. A process according to embodiments 131, wherein the composition comprises at least one stabilizing agent, and wherein the quantity of crystals will have a MHD of from 150 to 450 nm if left in water at 25° C. for at least 1 hour.

139. A process according to embodiments 138, wherein the quantity of crystals will have a MHD of from 150 to 4500 nm if left in water at 25° C. for 24 hours.

140. A process according to any of embodiments 132-140, wherein the stabilizing agent comprises a polymer.

141. A process according to embodiment 140, wherein the polymer comprises a cationic or anionic polymer.

142. A process according to embodiment 140, wherein the polymer is a cationic polymer.

143. A process according to embodiment 142, wherein the cationic polymer comprises ammonium functionality.

144. A process according to embodiment 143, wherein the cationic polymer comprises quaternary ammonium functionality.

145. A process according to any of embodiments 141-144, wherein the cationic polymer comprises a polymer that is formed from polymerization of compounds comprising at least one acrylate-containing compound.

146. A process according to any of embodiments 141-145, wherein the cationic polymer comprises Poly(ethyl acrylate-co-methyl methacrylate-co-trimethylammonioethyl methacrylate chloride) 1:2:0.2 (Eudragit RL).

147. A process according to any of embodiments 132-146, wherein the stabilizing agent comprises between 10 and 20 percent by weight of the liquid composition.

148. A process according to any of embodiments 132-146, wherein the stabilizing agent comprises between 12 and 17 percent by weight of the liquid composition.

149. A process according to any of embodiments 128-148, wherein the liquid composition comprises a surfactant.

150. A process according to embodiment 149, wherein the surfactant is selected from the group consisting of polyethylene glycol sorbitan monooleate surfactants, polyethylene glycol hydrogenated castor oil, block copolymers of poly(ethylene oxide) and poly(propylene oxide), sodium lauryl sulfate, benzalkonium chloride, and sodium docusate.

151. A process according to embodiment 149 or 150, wherein the surfactant comprises a nonionic surfactant.

152. A process according to any of embodiments 149-151, wherein the surfactant comprises a sorbitan ester.

153. A process according to any of embodiments 149-152, wherein the surfactant is polyethylene glycol sorbitan monooleate.

154. A process according to any of embodiments 149-153, wherein the surfactant comprises from 1 to 5 percent by weight of the composition.

155. A process according to any of embodiments 149-153, wherein the surfactant comprises from 1 to 3 percent by weight of the composition.

156. A process according to any of embodiments 128-155, wherein the quantity of crystals of 4-methyl-5-(pyrazin-2-yl)-3H-1,2-dithiole-3-thione comprise less than 20 percent by weight of the liquid composition.

157. A process according to any of embodiments 128-155, wherein the quantity of crystals of 4-methyl-5-(pyrazin-2-yl)-3H-1,2-dithiole-3-thione comprise less than 15 percent by weight of the liquid composition.

158. A process according to any of embodiments 128-155, wherein the quantity of crystals of 4-methyl-5-(pyrazin-2-yl)-3H-1,2-dithiole-3-thione comprise from 5 to 12 percent by weight of the liquid composition.

159. A process according to any of embodiments 128-155, wherein the quantity of crystals of 4-methyl-5-(pyrazin-2-yl)-3H-1,2-dithiole-3-thione comprise from 7 to 10 percent by weight of the liquid composition.

160. A process according to any of embodiments 128-159, further comprising the step of combining a bulking agent with at least a portion of said liquid composition to form a liquid composition comprising the bulking agent and crystals.

161. A process according to embodiment 160, wherein the step of combining a bulking agent comprises mixing the bulking agent and a liquid composition comprising the crystals to form an liquid composition comprising the bulking agent and crystals.

162. A process according to any of embodiments 160-161, wherein the bulking agent comprises a polyvinylpyrrolidone compound.

163. A process according to any of embodiments 160-162, wherein the bulking agent comprises a copolymer of polyvinylpyrrolidone and poly(vinyl acetate) with a ratio of approximately 6:4 of vinylpyrrolidone and vinyl acetate monomers (PVP-VA64).

164. A process according to any of embodiments 128-163, wherein the liquid composition comprises water.

165. A process according to any of embodiments 128-164, wherein the liquid composition comprises a non-aqueous solvent.

166. A process according to any of embodiments 160-165, comprising the step of adding a liquid comprising water to adjust the percent solids content of the liquid composition comprising the bulking agent and crystals.

167. A process according to any of embodiments 160-166, wherein the bulking agent comprises less than 30 percent by weight of the liquid composition comprising the bulking agent and crystals.

168. A process according to any of embodiments 160-166, wherein the bulking agent comprises between 15 and 25 percent by weight of the liquid composition comprising the bulking agent and crystals.

169. A process according to any of embodiments 160-168, wherein the liquid composition comprising the bulking agent and crystals comprises more than 35 percent total solids.

170. A process according to any of embodiments 160-168, wherein the liquid composition comprising the bulking agent and crystals comprises from 30 to 35 percent total solids.

171. A process according to any of embodiments 160-168, wherein the liquid composition comprising the bulking agent and crystals comprises from 25 to 30 percent total solids.

172. A process according to any of embodiments 160-168, wherein the liquid composition comprising the bulking agent and crystals comprises from 20 to 25 percent total solids.

173. A process according to any of embodiments 160-168, wherein the liquid composition comprising the bulking agent and crystals comprises from 15 to 20 percent total solids.

174. A process according to any of embodiments 160-168, wherein the liquid composition comprising the bulking agent and crystals comprises less than 15 percent total solids.

175. A process according to any of embodiments 160-168, wherein the liquid composition comprising the bulking agent and crystals comprises about 28 percent total solids.

176. A process according to any of embodiments 160-175 further comprising one or more steps to form a dry composition that substantially excludes liquid, wherein the one or more steps comprise the step of spray drying the liquid composition comprising the bulking agent and crystals.

177. A process according to any of embodiments 160-175 further comprising one or more steps to form a dry composition that substantially excludes liquid, wherein the one or more steps comprise the step of lyophilizing the liquid composition comprising the bulking agent and crystals.

178. A process according to any of embodiments 128-175, wherein the liquid composition comprises less than 1 percent of drug-degradent impurities relative to 4-methyl- 5-(pyrazin-2-yl)-3H-1,2-dithiole-3-thione in the liquid composition and less than 2 percent total impurities relative to the 4-methyl-5-(pyrazin-2-yl)-3H-1,2-dithiole-3-thione in the liquid composition.
179. A process according to any of embodiments 128-175, wherein the liquid composition comprising the bulking agent and crystals comprises less than 0.5 percent of drug-degradent impurities relative to 4-methyl-5-(pyrazin-2-yl)-3H-1,2-dithiole-3-thione in the liquid composition and less than 1 percent total impurities relative to the 4-methyl-5-(pyrazin-2-yl)-3H-1,2-dithiole-3-thione in the liquid composition.
180. A process according to any of embodiments 176 or 177, wherein the dry composition comprises less than 1 percent of drug-degradent impurities relative to 4-methyl-5-(pyrazin-2-yl)-3H-1,2-dithiole-3-thione in the liquid composition and less than 2 percent total impurities relative to the 4-methyl-5-(pyrazin-2-yl)-3H-1,2-dithiole-3-thione in the liquid composition.
181. A process according to any of embodiments 176 or 177, wherein the dry composition comprising the bulking agent and crystals comprises less than 0.5 percent of drug-degradent impurities relative to 4-methyl-5-(pyrazin-2-yl)-3H-1,2-dithiole-3-thione in the liquid composition and less than 1 percent total impurities relative to the 4-methyl-5-(pyrazin-2-yl)-3H-1,2-dithiole-3-thione in the liquid composition.
182. A process according to any of embodiments 128-181, wherein the polydispersity index (PdI) of the crystals in the quantity is less than 0.80, wherein PdI=$(\sigma/d)^2$, wherein a is the standard deviation and d is the mean hydrodynamic diameter (Z-average).
183. A process according to embodiment 182 wherein the polydispersity index (PdI) of the crystals in the quantity is less than 0.60.
184. A process according to embodiment 182, wherein the polydispersity index (PdI) of the crystals in the quantity is between 0.10 and 0.60.
185. A process according to embodiment 182, wherein the polydispersity index (PdI) of the crystals in the quantity is between 0.10 and 0.45.
186. A process according to any of embodiments 128-185, wherein the quantity of crystals comprises substantially the entire quantity of 4-methyl-5-(pyrazin-2-yl)-3H-1,2-dithiole-3-thione present in the liquid composition.
187. A process comprising the steps of providing a pharmaceutically acceptable container comprising a cavity, and adding to the container a dose of a dry pharmaceutical composition, wherein the dry pharmaceutical composition comprises a composition according to any of embodiments 1-39 and 64-99 that substantially excludes water, wherein the cavity is of sufficient size to hold both the dry pharmaceutical composition and an amount of a liquid sufficient to permit mixing of the dry pharmaceutical composition with a liquid to form a liquid pharmaceutical composition.
188. A process comprising the steps of
providing a pharmaceutically acceptable container comprising a cavity, and
adding to the container a dose of a dry pharmaceutical composition, wherein the dry pharmaceutical composition comprises a dry composition prepared according to embodiment 176 or 177,
wherein the cavity is of sufficient size to hold both the dry pharmaceutical composition and an amount of liquid sufficient to permit mixing of the dry pharmaceutical composition with a liquid to form a liquid pharmaceutical composition.
189. A process according to embodiment 187 or 188, wherein the container comprises a compartment separate from the cavity, and the dry pharmaceutical composition is added to the compartment.
190. A process according to any of embodiments 187-188, wherein the container comprises a releasable coupling for uncoupling a portion of the container to provide an opening for dispensing a liquid pharmaceutical composition from the container.
191. A process according to embodiment 189, wherein the container further comprises a releasable coupling for uncoupling a portion of the container to provide an opening for dispensing a liquid composition from the container, and wherein the releasable coupling connects the portion of the container comprising the cavity to the portion of the container comprising the compartment that contains the dose of a dry pharmaceutical composition.
192. A process according to any of embodiments 189-191, wherein the container further comprises a breakable seal between the compartment and the cavity, and wherein the dry pharmaceutical composition remains separate from the cavity when said seal is unbroken, and wherein the dry pharmaceutical composition can enter the cavity when the seal is broken.
193. A process according to any of embodiments 187-192, further comprises adding a liquid to the pharmaceutically acceptable container and mixing the liquid and dry pharmaceutical composition.
194. A process comprising the steps of adding a liquid to the cavity of a pharmaceutically acceptable container according to any of embodiments 119-124, and mixing the dose of dry pharmaceutical composition with the liquid.
195. A process comprising the steps of adding a liquid to the cavity of a pharmaceutically acceptable container according to embodiment 122-124, causing the dry pharmaceutical composition in the compartment to enter the cavity, and mixing the dose of dry pharmaceutical composition with the liquid.
196. A process comprising the steps of adding a liquid to the cavity of a pharmaceutically acceptable container according to embodiment 124, breaking the seal between the compartment and the cavity and causing the dry pharmaceutical composition in the compartment to enter the cavity, and mixing the dose of dry pharmaceutical composition with the liquid.
197. A process according to any of embodiments 193-196, wherein the liquid further comprises at least one pharmaceutically acceptable taste-modifying additive.
198. A process according to any of embodiments 193-197, wherein the step of mixing is carried out by shaking the container for ten minutes or less.
199. A process according to any of embodiments 193-197, wherein the step of mixing is carried out by shaking the container for five minutes or less.
200. A process according to any of embodiments 193-197, wherein the step of mixing is carried out by shaking the container for three minutes or less.
201. A process according to any of embodiments 193-197, wherein the step of mixing is carried out by shaking the container for two minutes or less.
202. A process according to any of embodiments 193-197, wherein the step of mixing is carried out by shaking the container for one minute or less.

203. A process according to any of embodiments 193-202, wherein the liquid comprises water.
204. A process according to any of embodiments 193-203, wherein the liquid comprises a non-aqueous solvent.
205. A process for treating a human or non-human animal patient in need comprising administering to the patient a composition prepared according to the process of any of embodiments 193-204.
206. A process for treating a human or non-human animal patient in need comprising administering to the patient a pharmaceutical composition according to any of embodiments 98-108.
207. A process according to embodiment 205 or 206, wherein the administration comprises an oral administration.
208. A process according to embodiment 207, wherein the administration comprises a buccal administration
209. A process according to embodiment 208, wherein the buccal administration comprises a swish and swallow administration.
210. A process according to embodiment 208, where the buccal administration comprises a swish and spit administration.
211. A process for treating a human or non-human animal patient in need comprising administering to the patient a pharmaceutical composition according to any of embodiments 109-112.
212. A process for preventing, treating, ameliorating, lessening the severity and/or shortening the duration of mucositis for a human or non-human animal patient in need comprising orally administering a pharmaceutical composition according to any of embodiments 115-118 to the patient.
213. A process for preventing, treating, ameliorating, lessening the severity and/or shortening the duration of mucositis for a human or non-human animal patient in need comprising orally administering an pharmaceutical composition prepared according to any of embodiments 193-204.
214. A process for preventing, treating, ameliorating, lessening the severity and/or shortening the duration of mucositis for a human or non-human animal patient in need comprising orally administering to the patient a pharmaceutical composition according to any of embodiments 98-108.
215. A process according to any of embodiments 212-214, wherein the mucositis in oral mucositis.
216. A process according to any of embodiments 212-214, wherein the mucositis in mucositis of the alimentary canal.
217. A process for preventing, treating, ameliorating, lessening the severity and/or shortening the duration of mucositis for a human or non-human animal patient in need comprising topically administering a composition according to embodiment 109.
218. A process for preventing, treating, ameliorating, lessening the severity and/or shortening the duration of mucositis for a human or non-human animal patient in need comprising rectally administering a composition according to embodiment 110 or 111.
219. A process for preventing, treating, ameliorating, lessening the severity and/or shortening the duration of mucositis for a human or non-human animal patient in need comprising administering by inhalation a composition according to embodiment 112.
220. A process according to any of embodiments 205-219, wherein the patient is undergoing radiation therapy.
221. A process according to embodiment 222, wherein the patient receives administration prior to the patient receiving his or her next radiation treatment.
222. A process according to embodiment 221, wherein administration is carried out one hour or less prior to the patient receiving a radiation treatment.
223. A process according to embodiment 221, wherein administration is carried out one day or less prior to the patient receiving a radiation treatment.
224. A process according to any of embodiments 220-223, wherein administration is carried out after the patient receives a radiation treatment.
225. A process according to embodiment 224, wherein administration is carried out within one hour after the patient receives a radiation treatment.
226. A process according to embodiment 224, wherein administration is carried out less within one day after the patient receives a radiation treatment.
227. A process according to any of embodiments 205-226, wherein the composition comprising oltipraz is co-administered with at least one pharmaceutically acceptable agent selected from the group consisting of antioxidants, agents that enhance glutathione synthesis, glutathione, Medihoney, NF-kappaB inhibitors, anti-inflammatory agents, and compounds prevent damage from reactive $O_2^-$ (superoxide).
228. A process according to any of embodiments 205-226, wherein the composition comprising oltipraz is co-administered with at least one pharmaceutically acceptable agent selected from the group consisting of N acetylcysteine, pantothenic acid (vitamin B5), glutathione, Medihoney, curcumin, Mesalamine, and superoxide dismutase.
229. A process according to any of embodiments 205-226, wherein the composition comprising oltipraz is co-administered separately as part of a dosing regimen with at least one pharmaceutically acceptable agent selected from the group consisting of antioxidants, agents that enhance glutathione synthesis, glutathione, Medihoney, NF-kappaB inhibitors, anti-inflammatory agents, and compounds prevent damage from reactive $O_2^-$ (superoxide).
230. A process according to any of embodiments 205-226, wherein the composition comprising oltipraz is co-administered separately as part of a dosing regimen with at least one pharmaceutically acceptable agent selected from the group consisting of N acetylcysteine, pantothenic acid (vitamin B5), glutathione, Medihoney, curcumin, Mesalamine, and superoxide dismutase.
231. A pharmaceutical composition comprising a quantity of 4-methyl-5-(pyrazin-2-yl)-3H-1,2-dithiole-3-thione, and at least one additive that provides a rapid onset of flavor and/or cooling sensation.
232. A pharmaceutical composition according to any of embodiments 40-108, further comprising at least one additive that provides a rapid onset of flavor and/or cooling sensation.
233. A pharmaceutical composition according to embodiment 231 or 232, wherein the at least one rapid onset additive comprises at least one mint flavoring additive.
234. A pharmaceutical composition according to embodiment 233, wherein the concentration of all mint flavoring additives present is from 0.00001 to 0.1 percent by weight.
235. A pharmaceutical composition according to embodiment 233, wherein the concentration of all mint flavoring additives present is from 0.0005 to 0.005 percent by weight.

236. A pharmaceutical composition according to any of embodiments 231-235, wherein the composition comprises menthol flavoring.
237. A pharmaceutical composition according to any of embodiments 231-236, wherein the composition comprises at least one berry flavor additive.
238. A pharmaceutical composition according to embodiment 237, wherein the at least one berry flavor additive comprises a flavor from a berry that comprises a red color.
239. A pharmaceutical composition according to embodiment 236 or 237, wherein the at least one berry flavor additive comprises at least one berry flavor selected from the group consisting of raspberry, blueberry and blackberry.
240. A pharmaceutical composition according to any of embodiments 237-239, wherein the concentration of all berry flavoring additives present is from 0.01 to 1 percent by weight.
241. A pharmaceutical composition according to any of embodiments 237-239, wherein the concentration of all berry flavoring additives present is from 0.1 to 0.5 percent by weight.
242. A pharmaceutical composition according to any of embodiments 237-239, wherein the concentration of all berry flavoring additives present is from 0.2 to 0.3 percent by weight.
243. A pharmaceutical composition according to any of embodiments 231-242, wherein the composition comprises at least one additive that provides a long-lasting flavor that reduces the perceived bitterness of the liquid composition.
244. A pharmaceutical composition according to embodiment 243, wherein the at least one long-lasting flavor additive comprises at least one additive that provides a sense of cooling.
245. A pharmaceutical composition according to any of embodiments 243 or 244, wherein the composition comprises at least one flavor of Physcool®.
246. A pharmaceutical composition according to embodiment 245, wherein the concentration of Physcool® flavoring is from 0.001 to 0.1 percent by weight.
247. A pharmaceutical composition according to embodiment 245, wherein the concentration of Physcool® flavoring is from 0.01 to 0.05 percent by weight.
248. A pharmaceutical composition according to embodiment 245, wherein the concentration of Physcool® flavoring is about 0.025 percent by weight.
249. A pharmaceutical composition according to any of embodiments 231-248, wherein the composition comprises at least one sweetening additive.
250. A pharmaceutical composition according to embodiment 249, wherein the at least one sweetening additive comprises a compound selected from the group consisting of monosaccharides, disaccharides, oligosaccharides, alcohols, and high-potency sweeteners.
251. A pharmaceutical composition according to embodiment 249, wherein the at least one sweetening additive is selected from the group consisting of aspartame, saccharin, neotame, acesulfame potassium, xylitol, sorbitol, mannitol, sucrose, fructose, glucose, maltose, lactose, xylose, and sucralose.
252. A pharmaceutical composition according to embodiment 251, wherein the at least one sweetening additive comprises sucralose.
253. A pharmaceutical composition according to embodiment 252, wherein the concentration of sucralose is from 0.1 to 1.5 mg/mL.
254. A pharmaceutical composition according to embodiment 252, wherein the concentration of sucralose is from 0.5 to 1.0 mg/mL.
255. A pharmaceutically acceptable container according to any of embodiments 119-127, wherein said container comprises at least one additive that provides a rapid onset of flavor and/or cooling sensation.
256. A pharmaceutically acceptable container according to embodiment 255, wherein the at least one rapid onset additive comprises at least one mint flavoring additive.
257. A pharmaceutically acceptable container according to embodiment 255, wherein the concentration of all mint flavoring additives present is from 0.00001 to 0.1 percent by weight.
258. A pharmaceutically acceptable container according to embodiment 255, wherein the concentration of all mint flavoring additives present is from 0.0005 to 0.005 percent by weight.
259. A pharmaceutically acceptable container according to any of embodiments 255-258, wherein the container comprises menthol flavoring.
260. A pharmaceutically acceptable container according to any of embodiments 255-259, wherein the container comprises at least one berry flavor additive.
261. A pharmaceutically acceptable container according to embodiment 260, wherein the at least one berry flavor additive comprises a flavor from a berry that comprises a red color.
262. A pharmaceutically acceptable container according to embodiment 259 or 260, wherein the at least one berry flavor additive comprises at least one berry flavor selected from the group consisting of raspberry, blueberry and blackberry.
263. A pharmaceutically acceptable container according to any of embodiments 260-262, wherein the concentration of all berry flavoring additives present is from 0.01 to 1 percent by weight.
264. A pharmaceutically acceptable container according to any of embodiments 260-262, wherein the concentration of all berry flavoring additives present is from 0.1 to 0.5 percent by weight.
265. A pharmaceutically acceptable container according to any of embodiments 260-262, wherein the concentration of all berry flavoring additives present is from 0.2 to 0.3 percent by weight.
266. A pharmaceutically acceptable container according to any of embodiments 255-265, wherein the container comprises at least one additive that provides a long-lasting flavor that reduces the perceived bitterness of the liquid composition.
267. A pharmaceutically acceptable container according to embodiment 266, wherein the at least one long-lasting flavor additive comprises at least one additive that provides a sense of cooling.
268. A pharmaceutically acceptable container according to any of embodiments 266 or 267, wherein the container comprises at least one flavor of Physcool®.
269. A pharmaceutically acceptable container according to embodiment 268, wherein the concentration of Physcool® flavoring is from 0.001 to 0.1 percent by weight.
270. A pharmaceutically acceptable container according to embodiment 268, wherein the concentration of Physcool® flavoring is from 0.01 to 0.05 percent by weight.
271. A pharmaceutically acceptable container according to embodiment 268, wherein the concentration of Physcool® flavoring is about 0.025 percent by weight.

272. A pharmaceutically acceptable container according to any of embodiments 255-271, wherein the container comprises at least one sweetening additive.
273. A pharmaceutically acceptable container according to embodiment 272, wherein the at least one sweetening additive comprises a compound selected from the group consisting of monosaccharides, disaccharides, oligosaccharides, alcohols, and high-potency sweeteners.
274. A pharmaceutically acceptable container according to any of embodiment 272, wherein the at least one sweetening additive is selected from the group consisting of aspartame, saccharin, neotame, acesulfame potassium, xylitol, sorbitol, mannitol, sucrose, fructose, glucose, maltose, lactose, xylose, and sucralose.
275. A pharmaceutically acceptable container according to embodiment 274, wherein the at least one sweetening additive comprises sucralose.
276. A pharmaceutically acceptable container according to embodiment 274, wherein the concentration of sucralose is from 0.1 to 1.5 mg/mL.
277. A pharmaceutically acceptable container according to embodiment 274, wherein the concentration of sucralose is from 0.5 to 1.0 mg/mL.
278. A pharmaceutically acceptable container according to embodiment 272, wherein the container comprises a liquid, and wherein the liquid comprises one or more ingredients selected from the group consisting of said at least one additive that provides a rapid onset of flavor and/or cooling sensation, said at least one berry flavor additive, said at least one additive that provides a long-lasting flavor that reduces the perceived bitterness of the liquid composition, and said at least one sweetening additive.
279. A pharmaceutically acceptable container according to embodiment 278, wherein the container comprises a liquid, and wherein the liquid comprises two or more ingredients selected from the group consisting of said at least one additive that provides a rapid onset of flavor and/or cooling sensation, said at least one berry flavor additive, said at least one additive that provides a long-lasting flavor that reduces the perceived bitterness of the liquid composition, and said at least one sweetening additive.
280. A pharmaceutically acceptable container according to embodiment 278, wherein the container comprises a liquid, and wherein the liquid comprises three or more ingredients selected from the group consisting of said at least one additive that provides a rapid onset of flavor and/or cooling sensation, said at least one berry flavor additive, said at least one additive that provides a long-lasting flavor that reduces the perceived bitterness of the liquid composition, and said at least one sweetening additive.
281. A pharmaceutically acceptable container according to embodiment 278, wherein the container comprises a liquid, and wherein the liquid comprises said at least one additive that provides a rapid onset of flavor and/or cooling sensation, said at least one berry flavor additive, said at least one additive that provides a long-lasting flavor that reduces the perceived bitterness of the liquid composition, and said at least one sweetening additive.
282. A pharmaceutically acceptable container according to embodiment 281, wherein the container comprises a liquid, and wherein the liquid comprises at least one mint flavoring additive, at least one berry flavor additive that comprises a flavor from a berry that comprises a red color, at least one Physcool® additive, and sucralose.
283. A pharmaceutically acceptable container according to any of embodiments 255-282, wherein the comprises a liquid, and wherein the liquid comprises at least one mint flavoring additive, and wherein the concentration of all mint flavoring additives present in the liquid is from 0.00001 to 0.1 percent by weight.
284. A pharmaceutically acceptable container according to embodiment 283, wherein the concentration of all mint flavoring additives present in the liquid is from 0.0005 to 0.005 percent by weight.
285. A pharmaceutically acceptable container according to any of embodiments 255-284, wherein the container comprises a liquid, and wherein the liquid comprises menthol flavoring.
286. A pharmaceutically acceptable container according to any of embodiments 260-285, wherein the container comprises a liquid, and wherein the liquid comprises at least one berry flavor additive, and wherein the concentration of all berry flavoring additives present in the liquid is from 0.01 to 1 percent by weight.
287. A pharmaceutically acceptable container according to embodiment 286, wherein the concentration of all berry flavoring additives present in the liquid is from 0.1 to 0.5 percent by weight.
288. A pharmaceutically acceptable container according to embodiment 286, wherein the concentration of all berry flavoring additives present in the liquid is from 0.2 to 0.3 percent by weight.
289. A pharmaceutically acceptable container according to any of embodiments 266-288, wherein the container comprises a liquid, and wherein the liquid comprises at least one additive that provides a long-lasting flavor that reduces the perceived bitterness of the liquid composition.
290. A pharmaceutically acceptable container according to embodiment 289, wherein the at least one long-lasting flavor additive in the liquid comprises at least one additive that provides a sense of cooling.
291. A pharmaceutically acceptable container according to any of embodiments 289 or 290, wherein the liquid comprises at least one flavor of Physcool®.
292. A pharmaceutically acceptable container according to embodiment 291, wherein the concentration of Physcool® flavoring in the liquid is from 0.001 to 0.1 percent by weight.
293. A pharmaceutically acceptable container according to embodiment 291, wherein the concentration of Physcool® flavoring in the liquid is from 0.01 to 0.05 percent by weight.
294. A pharmaceutically acceptable container according to embodiment 291, wherein the concentration of Physcool® flavoring in the liquid is about 0.025 percent by weight.
295. A pharmaceutically acceptable container according to any of embodiments 278-294, wherein the container comprises a liquid, and wherein the liquid comprises at least one sweetening additive.
296. A pharmaceutically acceptable container according to embodiment 295, wherein the at least one sweetening additive in the liquid comprises a compound selected from the group consisting of monosaccharides, disaccharides, oligosaccharides, alcohols, and high-potency sweeteners wherein the sweetener comprises a sugar or a high-potency sweetener.
297. A pharmaceutically acceptable container according to any of embodiment 295, wherein the at least one sweetening additive in the liquid is selected from the group consisting of aspartame, saccharin, neotame, acesulfame potassium, xylitol, sorbitol, mannitol, sucrose, fructose, glucose, maltose, lactose, xylose, and sucralose.

298. A pharmaceutically acceptable container according to embodiment 295, wherein the at least one sweetening additive in the liquid comprises sucralose.

299. A pharmaceutically acceptable container according to embodiment 298, wherein the concentration of sucralose in the liquid is from 0.1 to 1.5 mg/mL.

300. A pharmaceutically acceptable container according to embodiment 299, wherein the concentration of sucralose in the liquid is from 0.5 to 1.0 mg/mL.

301. A pharmaceutically acceptable container according to any of embodiments 278-300, wherein the liquid comprises water.

302. A pharmaceutically acceptable container according to any of embodiments 278-301, wherein the liquid comprises a non-aqueous solvent.

303. A process according to any of embodiments 193-202, wherein the liquid comprises one or more ingredients selected from the group consisting of said at least one additive that provides a rapid onset of flavor and/or cooling sensation, said at least one berry flavor additive, said at least one additive that provides a long-lasting flavor that reduces the perceived bitterness of the liquid composition, and said at least one sweetening additive.

304. A process according to any of embodiments 193-202, wherein the liquid comprises two or more ingredients selected from the group consisting of said at least one additive that provides a rapid onset of flavor and/or cooling sensation, said at least one berry flavor additive, said at least one additive that provides a long-lasting flavor that reduces the perceived bitterness of the liquid composition, and said at least one sweetening additive.

305. A process according to any of embodiments 193-202, wherein the liquid comprises three or more ingredients selected from the group consisting of said at least one additive that provides a rapid onset of flavor and/or cooling sensation, said at least one berry flavor additive, said at least one additive that provides a long-lasting flavor that reduces the perceived bitterness of the liquid composition, and said at least one sweetening additive.

306. A process according to any of embodiments 193-202, wherein the liquid comprises said at least one additive that provides a rapid onset of flavor and/or cooling sensation, said at least one berry flavor additive, said at least one additive that provides a long-lasting flavor that reduces the perceived bitterness of the liquid composition, and said at least one sweetening additive.

307. A process according to embodiment 306, wherein the liquid comprises at least one mint flavoring additive, at least one berry flavor additive that comprises a flavor from a berry that comprises a red color, at least one Physcool® additive, and sucralose.

308. A process according to any of embodiments 303-307, wherein the liquid comprises at least one mint flavoring additive, and wherein the concentration of all mint flavoring additives present in the liquid is from 0.00001 to 0.1 percent by weight.

309. A process according to embodiment 308, wherein the concentration of all mint flavoring additives present in the liquid is from 0.0005 to 0.005 percent by weight.

310. A process according to any of embodiments 303-309, wherein the liquid comprises menthol flavoring.

311. A process according to any of embodiments 303-310, wherein the liquid comprises at least one berry flavor additive, and wherein the concentration of all berry flavoring additives present in the liquid is from 0.01 to 1 percent by weight.

312. A process according to embodiment 311, wherein the concentration of all berry flavoring additives present in the liquid is from 0.1 to 0.5 percent by weight.

313. A process according to embodiment 311, wherein the concentration of all berry flavoring additives present in the liquid is from 0.2 to 0.3 percent by weight.

314. A process according to any of embodiments 303-313, wherein the liquid comprises at least one additive that provides a long-lasting flavor that reduces the perceived bitterness of the liquid composition.

315. A process according to embodiment 314, wherein the at least one long-lasting flavor additive in the liquid comprises at least one additive that provides a sense of cooling.

316. A process according to any of embodiments 314 or 315, wherein the liquid comprises at least one flavor of Physcool®.

317. A process according to embodiment 316, wherein the concentration of Physcool® flavoring in the liquid is from 0.001 to 0.1 percent by weight.

318. A process according to embodiment 316, wherein the concentration of Physcool® flavoring in the liquid is from 0.01 to 0.05 percent by weight.

319. A process according to embodiment 316, wherein the concentration of Physcool® flavoring in the liquid is about 0.025 percent by weight.

320. A process according to any of embodiments 303-319, wherein the liquid comprises at least one sweetening additive.

321. A process according to embodiment 320, wherein the at least one sweetening additive in the liquid comprises a compound selected from the group consisting of monosaccharides, disaccharides, oligosaccharides, alcohols, and high-potency sweeteners wherein the sweetener comprises a sugar or a high-potency sweetener.

322. A process according to embodiment 320, wherein the at least one sweetening additive in the liquid is selected from the group consisting of aspartame, saccharin, neotame, acesulfame potassium, xylitol, sorbitol, mannitol, sucrose, fructose, glucose, maltose, lactose, xylose, and sucralose.

323. A process according to embodiment 320, wherein the at least one sweetening additive in the liquid comprises sucralose.

324. A process according to embodiment 323, wherein the concentration of sucralose in the liquid is from 0.1 to 1.5 mg/mL.

325. A process according to embodiment 323, wherein the concentration of sucralose in the liquid is from 0.5 to 1.0 mg/mL.

326. A process according to any of embodiments 303-325, wherein the liquid comprises water.

327. A process according to any of embodiments 303-326, wherein the liquid comprises a non-aqueous solvent.

328. A process for treating a human patient in need comprising administering to the patient a composition according to any of embodiments 231-254.

329. A process for treating a human patient in need comprising administering to the patient a composition prepared according to the process of any of embodiments 303-327.

330. A process according to embodiment 328 or 329, wherein the administration comprises an oral administration.

331. A process according to embodiment 328 or 329, wherein the administration comprises a buccal administration 332. A process according to embodiment 331, wherein the buccal administration comprises a swish and swallow administration.

333. A process according to embodiment 331, where the buccal administration comprises a swish and spit administration.

334. A process for preventing, treating, ameliorating, lessening the severity and/or shortening the duration of mucositis for a human patient in need comprising orally administering a pharmaceutical composition according to any of embodiments 231-254 to the patient.

335. A process for preventing, treating, ameliorating, lessening the severity and/or shortening the duration of mucositis for a human patient in need comprising orally administering a pharmaceutical composition prepared according to the process of any of embodiments 303-327.

336. A process according to any of embodiments 328-335, wherein the mucositis in oral mucositis.

337. A process according to any of embodiments 328-335, wherein the mucositis in mucositis of the alimentary canal.

338. A process according to any of embodiments 328-338, wherein the patient is undergoing radiation therapy.

339. A process according to embodiment 338, wherein the patient receives administration prior to the patient receiving his or her next radiation treatment.

340. A process according to embodiment 338, wherein administration is carried out one hour or less prior to the patient receiving a radiation treatment.

341. A process according to embodiment 338, wherein administration is carried out one day or less prior to the patient receiving a radiation treatment.

342. A process according to any of embodiments 338-341, wherein administration is carried out after the patient receives a radiation treatment.

343. A process according to embodiment 242, wherein administration is carried out within one hour after the patient receives a radiation treatment.

344. A process according to embodiment 242, wherein administration is carried out less within one day after the patient receives a radiation treatment.

345. A process according to any of embodiments 338-344, wherein the composition comprising oltipraz is co-administered with at least one pharmaceutically acceptable agent selected from the group consisting of antioxidants, agents that enhance glutathione synthesis, glutathione, Medihoney, NF-kappaB inhibitors, anti-inflammatory agents, and compounds prevent damage from reactive O2- (superoxide).

346. A process according to any of embodiments 338-344, wherein the composition comprising oltipraz is co-administered with at least one pharmaceutically acceptable agent selected from the group consisting of N acetylcysteine, pantothenic acid (vitamin B5), glutathione, Medihoney, curcumin, Mesalamine, and superoxide dismutase.

347. A process according to any of embodiments 338-344, wherein the composition comprising oltipraz is co-administered separately as part of a dosing regimen with at least one pharmaceutically acceptable agent selected from the group consisting of antioxidants, agents that enhance glutathione synthesis, glutathione, Medihoney, NF-kappaB inhibitors, anti-inflammatory agents, and compounds prevent damage from reactive O2- (superoxide).

348. A process according to any of embodiments 338-334, wherein the composition comprising oltipraz is co-administered separately as part of a dosing regimen with at least one pharmaceutically acceptable agent selected from the group consisting of N acetylcysteine, pantothenic acid (vitamin B5), glutathione, Medihoney, curcumin, Mesalamine, and superoxide dismutase.

349. A composition according to any of embodiments 40-112 or 231-254, wherein the solubility of the crystals of 4-methyl-5-(pyrazin-2-yl)-3H-1,2-dithiole-3-thione in the composition is at least 5.0 µg/ml of water at 20° C.

350. A composition according to any of embodiments 40-108 or 231-254, wherein the solubility of the crystals of 4-methyl-5-(pyrazin-2-yl)-3H-1,2-dithiole-3-thione in the composition is at least 5.5 µg/ml of water at 20° C.

351. A composition according to any of embodiments 40-108 or 231-254, wherein the solubility of the crystals of 4-methyl-5-(pyrazin-2-yl)-3H-1,2-dithiole-3-thione in the composition is between 5.5 µg/ml of water and 6.0 µg/ml of water at 20° C.

352. A composition according to any of embodiments 40-108 or 231-254, wherein the solubility of the crystals of 4-methyl-5-(pyrazin-2-yl)-3H-1,2-dithiole-3-thione in the composition is between 6.0 µg/ml of water and 8.0 µg/ml of water at 20° C.

353. A pharmaceutically acceptable container according to any of embodiments 119-127 or 255-302, wherein the solubility of the crystals of 4-methyl-5-(pyrazin-2-yl)-3H-1,2-dithiole-3-thione in the composition is at least 5.0 µg/ml of water at 20° C.

354. A pharmaceutically acceptable container according to any of embodiments 119-127 or 255-302, wherein the solubility of the crystals of 4-methyl-5-(pyrazin-2-yl)-3H-1,2-dithiole-3-thione in the composition is at least 5.5 µg/ml of water at 20° C.

355. A pharmaceutically acceptable container according to any of embodiments 119-127 or 255-302, wherein the solubility of the crystals of 4-methyl-5-(pyrazin-2-yl)-3H-1,2-dithiole-3-thione in the composition is between 5.5 µg/ml of water and 6.0 µg/ml of water at 20° C.

356. A pharmaceutically acceptable container according to any of embodiments 119-127 or 255-302, wherein the solubility of the crystals of 4-methyl-5-(pyrazin-2-yl)-3H-1,2-dithiole-3-thione in the composition is between 6.0 µg/ml of water and 8.0 µg/ml of water at 20° C.

357. A process according to any of embodiments 128-230 or 303-348, wherein the solubility of the crystals of 4-methyl-5-(pyrazin-2-yl)-3H-1,2-dithiole-3-thione is at least 5.0 µg/ml of water at 20° C.

358. A process according to any of embodiments 128-230 or 303-348, wherein the solubility of the crystals of 4-methyl-5-(pyrazin-2-yl)-3H-1,2-dithiole-3-thione is at least 5.5 µg/ml of water at 20° C.

359. A process according to any of embodiments 128-230 or 303-348, wherein the solubility of the crystals of 4-methyl-5-(pyrazin-2-yl)-3H-1,2-dithiole-3-thione is between 5.5 µg/ml of water and 6.0 µg/ml of water at 20° C.

360. A process according to any of embodiments 128-230 or 303-348, wherein the solubility of the crystals of 4-methyl-5-(pyrazin-2-yl)-3H-1,2-dithiole-3-thione is between 6.0 and 8.0 µg/ml of water at 20° C.

361. A process for increasing the gene expression of glutathione peroxidase 4 (GPX4) and/or myeloperoxidase (MPO) in a human or non-human animal patient comprising administering a pharmaceutical composition according to any of the embodiments 89-112 or 187-204, 231-254 or 349-352 to the patient.
362. A process for decreasing the gene expression of Peroxiredoxin 2 (PRDX2) in a human or non-human animal patient comprising administering a pharmaceutical composition according to any of the embodiments 89-112, 187-204, 231-254 or 349-352 to the patient.
363. A process for increasing the gene expression of glutathione peroxidase 4 (GPX4) and/or myeloperoxidase (MPO) and decreasing the gene expression of Peroxiredoxin 2 (PRDX2) in a human or non-human animal patient comprising administering a pharmaceutical composition according to any of the embodiments 89-112, 187-204, 231-254 or 349-352 to the patient.
364. A process according to any of embodiments 361-363, wherein the patient is undergoing chemotherapy and/or radiation therapy.
365. A process according to any of embodiments 361-364, wherein the patient has mucositis.
366. A process according to embodiment 365, wherein the mucositis is oral mucositis.
367. A process for decreasing intracellular reactive oxygen species (ROS) and/or decreasing oxidative stress in a human or non-human animal patient comprising administering a pharmaceutical composition according to any of the embodiments 89-112, 187-204, 231-254 or 349-352 to the patient.
368. A process according to embodiment 367, wherein the patient is undergoing chemotherapy or radiation therapy.
369. A process according to any of embodiments 367 or 368, wherein patient has mucositis.
370. A process according to embodiment 370, wherein the mucositis is oral mucositis.
371. A process for providing an antioxidant effect in a human or non-human animal patient comprising administering a pharmaceutical composition according to any of the embodiments 89-112, 187-204, 231-254 or 349-352 to the patient.
372. A process according to embodiment 371, wherein the patient is undergoing chemotherapy or radiation therapy.
373. A process according to embodiment 371 or 372, wherein the patient has mucositis.
374. A process according to embodiment 373, wherein the mucositis is oral mucositis.
375. A process for providing one or more effects selected from the group consisting of slowing the onset of oxidative damage, reducing the severity of oxidative damage, and/or reducing the duration of oxidative damage in a human or non-human animal patient comprising administering a pharmaceutical composition according to any of the embodiments 89-112, 187-204, 231-254 or 349-352 to the patient.
376. A process according to embodiment 375, wherein the patient is undergoing chemotherapy and/or radiation therapy.
377. A process according to embodiment 376, wherein the patient has mucositis.
378. A process according to embodiment 377, wherein the mucositis is oral mucositis.

Definitions

For convenience, certain terms employed in the specification and appended claims are collected here. These definitions should be read in light of the entire disclosure and understood as by a person of skill in the art.

The articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, processes described herein and claimed below can include steps in addition to the steps recited, and the order of the steps or acts of the process is not necessarily limited to the order in which the steps or acts of the process are recited. In the context of this disclosure, the words "process" and "method" are synonymous.

In the claims, as well as in the specification, all transitional phrases such as "comprising," "comprised of," "including," "carrying," "having," "containing," "involving," "holding." "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Those skilled in the art will recognize, or be able to ascertain using no more than routine experimentation, many equivalents to the specific embodiments described herein. Such equivalents are intended to be encompassed by the following claims.

What is claimed is:

1. A composition comprising: (i) a quantity of crystals of 4-methyl-5-(pyrazin-2-yl)-3H-1,2-dithiole-3-thione having an intensity averaged, mean hydrodynamic diameter (Z-average) ("MHD") of from 100 to 800 nm, as measured by dynamic light scattering at 25° C. on a Malvern Zetasizer Nano-ZSP or equivalent instrument equipped with a 173° backscatter detector using a suspension of the crystals in water at a concentration of 0.01 to 0.1 mg of crystals per mL of water following a 90 second equilibration time prior to analysis; (ii) a copovidone; and (iii) a cationic polymer formed by polymerization of compounds comprising at least one acrylate-containing compound.

2. A composition comprising a quantity of crystals according to claim 1 wherein the MHD is from about 300 to 800 nm.

3. A composition comprising a quantity of crystals according to claim 2, wherein the polydispersity index (PdI) of the crystals, defined as PdI=$(\sigma/d)^2$, wherein $\sigma$ is the standard deviation and d is the mean hydrodynamic diameter (Z-average) of the crystals, is from about 0.10 to about 0.60.

4. A composition comprising a quantity of crystals according to claim 3, wherein the solubility of the crystals in water at 20° C. is from about 3.5 to about 8 µg/ml.

5. A composition comprising crystals according to claim 1,
wherein the cationic polymer is poly(ethyl acrylate-co-methyl methacrylate-co-trimethylammonioethyl methacrylate chloride) polymerized in a ratio of 1:2:0.2; and
wherein the composition further comprises a surfactant selected from the group consisting of sodium isostearate, cetyl alcohol, polysorbates, steareth-10 (Brij 76), sodium dodecyl sulfate, lauryl dimethyl amine oxide, cetyltrimethylammonium bromide, polyethoxylated alcohols, polyoxyethylene sorbitan, octoxynol, N,N-dimethyldodecylamine-N-oxide, hexadecyltrimethylammonium bromide, polyoxyl 10 lauryl ether, bile salts, polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dihexadecyl phosphate, ceteareth-10 phosphate, methylbenzethonium chloride, dicetyl phosphate, ceteth-10 phosphate, ceteth-20, polyethylene glycol octadecyl ether with an average $M_n$~711, PEG-20 phytosterol, poloxamers, polyoxyethylene glycol alkyl ethers, polyoxypropylene glycol alkyl ethers, glucoside alkyl ethers, polyoxyethylene glycol alkylphenol ethers, glycerol alkyl esters, polyoxyethylene glycol sorbitan alkyl esters, sorbitan alkyl esters, cocamides, and polyoxyethylene (20) sorbitan monooleate.

6. A composition according to claim 1, further comprising polyvinylpyrrolidone or cellulosic polymers.

7. A composition according to claim 5 which is in liquid form as a substantially homogeneous dispersion of 4-methyl-5-(pyrazin-2-yl)-3H-1,2-dithiole-3-thione crystals, wherein the composition comprises water and/or a non-aqueous solvent.

8. A composition according to claim 5 which is in dry form, wherein the composition substantially excludes water and any non-aqueous solvent.

9. A liquid composition according to claim 7, further comprising an anti-foaming agent.

10. A liquid composition according to claim 9, wherein the anti-foaming agent is simethicone.

11. An aqueous composition comprising a dry composition according to claim 5 and an aqueous solution, wherein the weight: weight ratio of the dry composition to liquid is from 1:10 to 1:200.

12. A composition according to claim 11 in the form of a suspension, wherein the weight ratio of the dry composition to liquid is from about 1:10 to about 1:200, the suspension comprising:
  i) from about 0.0005 to about 0.005 wt % of a mint or menthol flavor, based on the overall weight of the suspension; and/or
  ii) from about 0.05 to about 0.5 wt % of a fruit flavor based on the overall weight of the suspension; and/or
  iii) from about 0.1 to about 1.5 mg/mL of a sweetener; and/or
  iv) from about 0.01 to about 0.05 wt % of a cooling/freshening agent; and optionally
  v) from about 0.05 to about 5 mg/mL of a preservative.

13. A composition in the form of a suspension according to claim 12 wherein the weight ratio of the dry composition to liquid is from about 1:30 to about 1:100, the suspension comprising:
  i) from about 0.0007 to about 0.003 wt % of a mint or menthol flavor based on the overall weight of the suspension; and/or
  ii) from about 0.1 to about 0.4 wt % of a fruit flavor based on the overall weight of the suspension; and/or
  iii) from about 0.5 to about 1 mg/mL of a sweetener selected from aspartame, saccharin, neotame, acesulfame potassium, xylitol, sorbitol, mannitol, sucrose, fructose, glucose, maltose, lactose, xylose and sucralose; and/or
  iv) from about 0.01 to about 0.05 wt % of a cooling/freshening agent; and optionally
  v) from about 0.1 to about 1 mg/mL of a preservative.

14. A pharmaceutical composition comprising a suspension according to claim 12, wherein:
  i) the composition is in liquid dosage form and comprises at least one pharmaceutically acceptable diluent, adjuvant, suspending agent and/or carrier; or
  ii) the composition is in dry dosage form and comprises at least one pharmaceutically acceptable additive, lubricant, excipient or diluent.

15. The composition according to claim 1, wherein the quantity of crystals comprises substantially the entire quantity of 4-methyl-5-(pyrazin-2-yl)-3H-1,2-dithiole-3-thione present in the composition.

16. A composition comprising a quantity of crystals according to claim 1 wherein the MHD is from about 100 to about 600 nm.

17. A composition comprising: (i) a quantity of crystals of 4-methyl-5-(pyrazin-2-yl)-3H-1,2-dithiole-3-thione having an intensity averaged, mean hydrodynamic diameter (Z-average) ("MHD") of from 100 to 800 nm, as measured by dynamic light scattering at 25° C. on a Malvern Zetasizer Nano-ZSP or equivalent instrument equipped with a 173° backscatter detector using a suspension of the crystals in water at a concentration of 0.01 to 0.1 mg of crystals per mL of water following a 90 second equilibration time prior to analysis; (ii) a copovidone; and (iii) a cationic polymer formed by polymerization of compounds comprising at least one acrylate-containing compound; wherein the quantity of crystals comprises substantially the entire quantity of 4-methyl-5-(pyrazin-2-yl)-3H-1,2-dithiole-3-thione present in the composition.

18. The composition comprising a quantity of crystals according to claim 17, wherein the MHD is from about 300 to 800 nm.

19. The composition of claim 18, further comprising at least one additive that provides a sense of cooling.

20. The composition of claim 1, wherein the copovidone is a copolymer of 1-vinyl-2-pyrrolidone and vinyl acetate in a ratio of 6:4 by mass.

21. The composition of claim 20, wherein the cationic polymer is poly(ethyl acrylate-co-methyl methacrylate-co-trimethylammonioethyl methacrylate chloride) polymerized in a ratio of 1:2:0.2.

22. The composition of claim 3, wherein the copovidone is a copolymer of 1-vinyl-2-pyrrolidone and vinyl acetate in a ratio of 6:4 by mass.

23. The composition of claim 22, wherein the cationic polymer is poly(ethyl acrylate-co-methyl methacrylate-co-trimethylammonioethyl methacrylate chloride) polymerized in a ratio of 1:2:0.2.

* * * * *